(12) United States Patent
Breitenstein et al.

(10) Patent No.: US 7,138,432 B1
(45) Date of Patent: Nov. 21, 2006

(54) ARYLSULFONAMIDO-SUBSTITUTED HYDROXAMIC ACID DERIVATIVES

(75) Inventors: Werner Breitenstein, Basel (CH); Kenji Hayakawa, Takarazuka (JP); Genji Iwasaki, Tsukuba (JP); Takanori Kanazawa, Tsukuba (JP); Tatsuhiko Kasaoka, Tsukuba (JP); Shinichi Koizumi, Inashiki-gun (JP); Shinichiro Matsunaga, Tsukuba (JP); Motowo Nakajima, Ashiya (JP); Junichi Sakaki, Kawasaki (JP)

(73) Assignee: Novartis AG, Basel (CH)

( * ) Notice: Subject to any disclaimer, the term of this patent is extended or adjusted under 35 U.S.C. 154(b) by 262 days.

(21) Appl. No.: 10/048,932

(22) PCT Filed: Aug. 7, 2000

(86) PCT No.: PCT/EP00/07641

§ 371 (c)(1),
(2), (4) Date: Feb. 5, 2002

(87) PCT Pub. No.: WO01/40827

PCT Pub. Date: Feb. 15, 2001

(30) Foreign Application Priority Data

Aug. 9, 1999 (GB) ................................. 9918684.3

(51) Int. Cl.
*A61K 31/18* (2006.01)
*C07C 303/00* (2006.01)

(52) U.S. Cl. .................. 514/602; 514/604; 564/84; 564/90

(58) Field of Classification Search ............ 564/84, 564/90; 546/336, 337; 548/255, 250, 146; 514/602, 604, 381, 383
See application file for complete search history.

(56) References Cited

U.S. PATENT DOCUMENTS

| | | | |
|---|---|---|---|
| 2,513,826 A | 7/1950 | Sprung et al. | |
| 5,455,258 A * | 10/1995 | MacPherson et al. | 514/357 |
| 5,500,337 A | 3/1996 | Benard et al. | |
| 5,932,695 A | 8/1999 | Floyd et al. | |
| 5,985,900 A * | 11/1999 | Bender et al. | 514/336 |
| 6,150,394 A | 11/2000 | Watanabe et al. | |
| 6,159,995 A | 12/2000 | Thorwart et al. | |
| 6,451,824 B1 | 9/2002 | Thorwart et al. | |

FOREIGN PATENT DOCUMENTS

| | | |
|---|---|---|
| EP | 306453 | 3/1989 |
| EP | 308860 | 3/1989 |
| EP | 469984 | 2/1992 |
| EP | 0877018 | 11/1998 |
| EP | 0877019 | 11/1998 |
| EP | 915086 | 5/1999 |
| EP | 0930067 | 7/1999 |
| EP | 0 950 656 | 10/1999 |
| EP | 0949244 | 10/1999 |
| FR | 2686878 | 8/1993 |
| JP | 11-236369 | 9/1999 |
| WO | WO 96/00214 | 1/1996 |
| WO | 97/44315 | 11/1997 |
| WO | 98/18754 | 5/1998 |
| WO | 98/25597 | 6/1998 |
| WO | WO 98/33768 | 8/1998 |
| WO | 98/47494 | 10/1998 |
| WO | WO 99/06340 | 2/1999 |
| WO | 99/42443 | 8/1999 |
| WO | WO 00/44709 | 8/2000 |
| WO | WO 00/44713 | 8/2000 |
| WO | 01 10827 | 2/2001 |
| WO | 02 064552 | 8/2002 |

OTHER PUBLICATIONS

Y. Tamura et al., J. Med. Chem, vol. 41, No. 4, pp. 640-649, XP002151755 (1998).
J. H. Uhlenbroek et al., Recl. Trav. Chim. Pays-Bas, vol. 75, pp. 129-146, XP000953403 (1956).
Scozzafava et al., "Protease Inhibitors: Synthesis of Potent Bacterial Collagenase and Matrix Metalloproteinase Inhibitors Incorporating N-4-nitrobenzylsulphonyglycine Hydroxamate Moieties," J. Med. Chem., vol. 43, No. 9, pp. 1858-1865 (2000).

(Continued)

*Primary Examiner*—Kamel A. Saeed
*Assistant Examiner*—Robert Shiao
(74) *Attorney, Agent, or Firm*—Lydia T. McNally; Edward J. Wilusz, Jr.

(57) ABSTRACT

α-Amino hydroxamic acid derivative of formula (I), in which R is $C_2$–$C_7$-alkyl, which is mono-, di- or trisubstituted by halogen, nitro, lower acyloxy, trifluoromethoxy, cyano, $C_3$–$C_5$-cycloalkyl or unsubstituted or substituted $C_3$–$C_4$-heteroaryl comprising one or two heteroatoms selected from the group consisting of O, S and N; or $C_3$–$C_7$-alkenyl or $C_3$–$C_7$-alkynyl, which in each case is unsubstituted or mono-, di- or trisubstituted by halogen, nitro, lower acyloxy, trifluoromethoxy, cyano, $C_3$–$C_5$-cycloalkyl or unsubstituted or substituted $C_3$–$C_6$-heteroaryl comprising one or two heteroatoms selected from the group consisting of O, S and N; and the other symbols are as defined in claim 1, are described. These compounds are MMP and in particular MMP2 inhibitors and can be used for treatment of MMP dependent diseases, in particular inflammation conditions, rheumatoid arthritis, osteoarthritis, tumors (tumor growth, metastasis, progression or invasi n) and pulmonary disorders (e.g. emphysema, COPD).

20 Claims, No Drawings

OTHER PUBLICATIONS

MacPherson et al., "Discovery of CGS 27023A, Non-Peptidic, Potent and Orally Active Stromelysin Inhibitor That Blocks Cartilage Degradation in Rabbits," J. Med. Chem., vol. 40, pp. 2525-2532 (1997).

Casini et al., "Sulfonamides and sulfonylated derivatives as anti-cancer agents," Current Cancer Drug Targets, vol. 2, pp. 55-75, especially p. 58 (2002).

Tamura et al., "Highly selective and orally active inhibitors of type IV collagenase (MMP-9 and MMP-2): N-Sulfonylamino acid derivatives," vol. 41, pp. 640-649, especially p. 640. (1998).

Connell et al., "Patent focus on cancer chemotherapeutics. II Angiogenesis agents: Apr. 2000- Sep. 2000," vol. 11(1), pp. 77-114, especially p. 84 (2001).

* cited by examiner

```
                        SEQUENCE LISTING

<160> NUMBER OF SEQ ID NOS: 8

<210> SEQ ID NO 1
<211> LENGTH: 4
<212> TYPE: PRT
<213> ORGANISM: Artificial Sequence
<220> FEATURE:
<223> OTHER INFORMATION: Leucine bound to Dpa-Ala-Arg, where Dpa =
      N-3-(2,4-dinitrophenyl)-L-alpha,
      beta-diaminopropionyl

<400> SEQUENCE: 1

Pro Leu Gly Leu
 1

<210> SEQ ID NO 2
<211> LENGTH: 29
<212> TYPE: DNA
```

-continued

```
<213> ORGANISM: Artificial Sequence
<220> FEATURE:
<223> OTHER INFORMATION: Oligonucleotide Primer

<400> SEQUENCE: 2
ctccatatgt acgccatcca gggtctcaa                                      29

<210> SEQ ID NO 3
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 3
ctcggatcct cacccataaa gttgctggat gcc                                 33

<210> SEQ ID NO 4
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 4
aagaagctta aggccagtat gcacagcttt cct                                 33

<210> SEQ ID NO 5
<211> LENGTH: 34
<212> TYPE: DNA
<213> ORGANISM: Artificial Sequence
<220> FEATURE:
<223> OTHER INFORMATION: Oligonucleotide Primer

<400> SEQUENCE: 5
aaggcggccg cacaccttct ttggactcac acca                                34

<210> SEQ ID NO 6
<211> LENGTH: 28
<212> TYPE: DNA
<213> ORGANISM: Artificial Sequence
<220> FEATURE:
<223> OTHER INFORMATION: Oligonucleotide Primer

<400> SEQUENCE: 6
gaattcgatg gaggcgctaa tggcccgg                                       28

<210> SEQ ID NO 7
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 7
ctcgagtcag cagcctagcc agtcggattt gat                                 33

<210> SEQ ID NO 8
<211> LENGTH: 9
<212> TYPE: PRT
<213> ORGANISM: Artificial Sequence
<220> FEATURE:
<223> OTHER INFORMATION: Lysine modified at epsilon nitrogen by
      2,4-dinitrophenyl

<400> SEQUENCE: 8
```

```
Gly Pro Gln Gly Leu Ala Gly Gln Lys
 1           5
```

ARYLSULFONAMIDO-SUBSTITUTED HYDROXAMIC ACID DERIVATIVES

This application is 371 of PCT/EP00/07641 filed on Aug. 7, 2000, which claim benif of United Kingdom 9918684.3 filed on Aug. 9, 1999.

The invention relates to arylsulfonamido-substituted hydroxamic acid derivatives, to processes and novel intermediates for their preparation, pharmaceutical compositions comprising said derivatives, pharmaceutical compositions comprising selective MMP2 inhibitors, the use of the hydroxamic acid derivatives as medicaments, a method of treating MMP, in particular MMP2, dependent diseases, in particular hyperproliferative diseases, or conditions in mammals which are responsive to MMP, in particular MMP2, inhibition, using selective MMP2 inhibitors, in particular the hydroxamic acid derivatives of formula I, or pharmaceutical compositions comprising selective MMP2 inhibitors, in particular the hydroxamic acid derivatives of formula I.

The invention relates in particular to α-amino hydroxamic acid derivatives of the formula I,

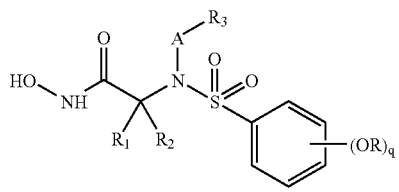

wherein
$R^1$ is hydrogen, substituted or unsubstituted aryl, lower alkyl, substituted or unsubstituted carbocyclic aryl-lower alkyl, substituted or unsubstituted heterocyclic-lower alkyl, substituted or unsubstituted $C_3$–$C_7$-cycloalkyl, substituted or unsubstituted $C_3$–$C_7$-cycloalkyl-lower alkyl, hydroxy-lower alkyl, lower alkoxy-lower alkyl, lower alkyl-(thio, sulfinyl or sulfonyl)-lower alkyl, amino-lower alkyl or mono- or di-lower alkylamino-lower alkyl;
$R^2$ is hydrogen or lower alkyl;
$R^3$ is substituted or unsubstituted $C_3$–$C_7$-cycloalkyl, substituted or unsubstituted carbocyclic aryl, substituted or unsubstituted heterocyclic aryl, substituted or unsubstituted heterocyclyl; or lower alkyl;
A is $C_1$–$C_3$ alkylen unsubstituted or substituted by lower alkyl;
q is 1–5;
R is $C_2$–$C_7$-alkyl, which is mono-, di- or trisubstituted by halogen, nitro, lower acyloxy, trifluoromethoxy, cyano, $C_3$–$C_5$-cycloalkyl or unsubstituted or substituted $C_3$–$C_6$-heteroaryl comprising one or two heteroatoms selected from the group consisting of O, S and N; or
  $C_3$–$C_7$-alkenyl or $C_3$–$C_7$-alkynyl, which in each case is unsubstituted or mono-, di- or trisubstituted by halogen, nitro, lower acyloxy, trifluoromethoxy, cyano, $C_3$–$C_5$-cycloalkyl or unsubstituted or substituted $C_3$–$C_6$-heteroaryl comprising one or two heteroatoms selected from the group consisting of O, S and N;
and to pharmaceutically acceptable prodrug derivatives; and pharmaceutically acceptable salts thereof.

Compounds of formula I are inhibitors of matrix-degrading metalloproteinases (MMP's) and are useful for the treatment of conditions related thereto.

q is preferably 1–3, as a rule 1 or 2, preferably 1. Only if it is possible for steric reasons, can q also be 4 or 5. If q is 1, OR is, for example, in the 3 position or, preferably, in the 4 position.

In a preferred embodiment of the invention, $R_1$ or $R_2$ represents hydrogen. In another preferred embodiment of the invention, $R_1$ and $R_2$ both represent hydrogen.

The general definitions used herein have the following meaning within the scope of the present invention, unless otherwise specified.

Halogen is, for example, fluorine, chlorine, bromine or iodine. Preferably it is fluorine or chlorine.

Unless stated otherwise, in the present disclosure organic radicals designated "lower" contain not more than 7, preferably not more than 4, carbon atoms.

Aryl represents carbocyclic or heterocyclic aryl.

A lower alkyl group is branched or unbranched and contains 1 to 7 carbon atoms, preferably 1–4 carbon atoms, and represents for example methyl, ethyl, propyl, butyl, isopropyl and isobutyl.

Carbocyclic aryl represents monocyclic or bicyclic aryl, preferably unsubstituted phenyl, or phenyl mono-, di- or trisubstituted by one, two or three radicals selected from lower alkyl, lower alkoxy, hydroxy, halogen, cyano, trifluoromethyl, lower alkyl amino, di-lower alkyl amino, phenoxy or phenyl, optionally substituted by lower alkoxy, lower alkyl, halogen, cyano, nitro or trifluoromethyl;

or phenyl disubstituted on adjacent carbon atoms by lower-alkylenedioxy, such as methylenedioxy;

or phenyl substituted by heterocyclic radicals as defined below, in particular pyrrolyl, imidazolyl, triazolyl, tetrazolyl, furyl, thienyl, morpholinyl, pyrrolidinyl, piperidinyl; or lower alkyl which is substituted by heterocyclic radicals as defined below, especially imidazolyl, triazolyl, chinolinyl or morpholinyl;

or 1- or 2-naphthyl.

Preferred is unsubstituted phenyl or phenyl monosubstituted by lower alkoxy, phenoxy, phenyl, halogen or trifluoromethyl. Particularly preferred is phenyl or phenyl monosubstituted by lower alkoxy, halogen or trifluoromethyl.

Carbocyclic aryl-lower alkyl represents preferably straight chain or branched aryl-$C_1$–$C_4$-alkyl in which carbocyclic aryl has meaning as defined above, e.g. benzyl or phenyl-(ethyl, propyl or butyl), each unsubstituted or substituted on the phenyl ring as defined under carbocyclic aryl above, advantageously optionally substituted benzyl.

Heterocyclic radicals are, in particular, mono- or bicyclic, aza-, thia-, oxa-, thiaza-, oxaza- or diaza radicals of aromatic character, and corresponding partly or, in particular, completely saturated heterocyclic radicals of this type, it being possible for such radicals to be mono-, di- or trisubstituted by functional groups. These radicals are linked to the rest of the molecule via a C—C bond and, in particular, monocyclic or bicyclic radicals with one nitrogen, oxygen or sulfur atom, and in particular aromatic radicals of this type, for example 2-pyrryl or 3-pyrryl, pyridyl, for example 2-, 3- or 4-pyridyl, and furthermore thienyl, for exampl 2- or 3-thienyl, or furyl, for example 2-furyl; analogous bicyclic radicals with one nitrogen, oxygen or sulfur atom are, for example, indolyl, such as 2- or 3-indolyl, quinolyl, such as 2- or 4-quinolyl, isoquinolyl, such as 3- or 5-isoquinolyl, benzofuranyl, such as 2-benzofuranyl, chromenyl, such as 3-chromenyl, or benzothienyl, such as 2- or 3-benzothienyl.

Suitable monocyclic and bicyclic radicals with more than one heteroatom are, for example, imidazolyl, such as 2-imidazolyl, pyrimidinyl, such as 2- or 4-pyrimidinyl, oxazolyl, such as 2-oxazolyl, isoxazolyl, such as 3-isoxazolyl, or thiazolyl, such as 2-thiazolyl, or benzimidazolyl, such as 2-benzimidazolyl, benzoxazolyl, such as 2-benzoxazolyl, or quinazolyl, such as 2-quinazolinyl. Corresponding partly, or, in particular, completely saturated analogous radicals are also suitable, such as 2-tetrahydrofuryl, 4-tetra hydrofuryl, 2- or 3-pyrrolidyl, 2-, 3- or 4-piperidyl and also 2- or 3-morpholinyl, 2- or 3-thiomorpholinyl, 2-piperazinyl and N,N'-bis-lower alkyl-2-piperazinyl radicals.

A heterocyclic radical can be substituted by one, two or more identical or different substituents (functional groups); the following substituents are particularly suitable: free, etherified and esterified hydroxyl groups; mercapto and lower alkylthio and substituted and unsubstituted phenylthio groups; halogen atoms; oxo groups, which are in the form of formyl (i.e. aldehydo) and keto groups, and also corresponding acetals or ketals; azido and nitro groups; primary, secondary and, preferably, tertiary amino groups, primary or secondary amino groups, acylamino groups and diacylamino groups protected by conventional protective groups, and unmodified or functionally modified sulfo groups, such as sulfamoyl groups or sulfo groups present in salt form. All these functional groups should not be on the C atom from which the free valency comes, and they are preferably separated from it by 2 or even more C atoms. The heterocyclic radical can also carry free and functionally modified carboxyl groups, such as carboxyl groups present in salt form or esterified carboxyl groups, carbamoyl, ureido or guanidino groups, which may or may not carrry one or two hydrocarbon radicals, and cyano groups.

Substituted carbocyclic aryl $R_3$ is preferably phenyl substituted by halogen, lower alkoxy, lower alkyl, di-lower alkyl amino, triazolyl, especially 1,2,4-triazolyl, 1,3,4-triazolyl, or 1,2,3-triazolyl, imidazolyl, e.g. 1-imidazolyl, morpholinyl, pyrrolidinyl, piperidinyl, tetrazolyl, pyrrolyl, furyl, in particular 3-furyl, thienyl, morpholinyl lower alkyl, quinolinyl lower alkyl, imidazolyl lower alkyl and triazolyl lower alkyl.

In a highly preferred embodiment of the invention $R_3$ represents substituted carbocyclic aryl, in which embodiment substituted carbocyclic aryl is phenyl which is preferably substituted in 4 position, preferably by triazolyl, in particular 1,2,4-triazol-1-yl.

Heterocyclic aryl $R_3$ represents monocyclic or bicyclic heteroaryl, for example pyridyl, quinolyl, isoquinolyl, benzothienyl, benzofuranyl, benzopyranyl, benzothiopyranyl, furanyl, pyrrolyl, thiazolyl, oxazolyl, isoxazolyl, triazolyl, tetrazolyl, pyrrazolyl, imidazolyl, thienyl, or any said radical substituted by lower alkyl or halogen. Pyridyl represents 2-, 3- or 4-pyridyl. Thienyl represents 2- or 3-thienyl, advantageously 2-thienyl. Quinolyl represents preferably 2-, 3- or 4-quinolyl, advantageously 2-quinolyl. Isoquinolyl represents preferably 1-, 3- or 4-isoquinolyl. Benzopyranyl, benzothiopyranyl represent preferably 3-benzopyranyl or 3-benzothiopyranyl, respectively. Thiazolyl represents preferably 2- or 4-thiazolyl, advantageously 4-thiazolyl. Triazolyl is preferably 2- or 5-(1,2,4-triazolyl). Tetrazolyl is preferably 5-tetrazolyl. Imidazolyl is preferably 4-imidazolyl. Preferably heterocyclic aryl represents pyridyl. It can be substituted by one, two or more identical or different substituents as defined for the heterocyclic radicals above.

Heterocyclic $R_3$ represents saturated or partly unsaturated, monocyclic or bicyclic heterocyclic radicals, comprising between 3 and 10 carbon atoms and one or two heteroatoms selected from the group consisting of O, S and N. Preferably, heterocyclic $R_3$ is selected from the group consisting of piperidinyl, morpholinyl, pyrrolidinyl, pyrrolinyl, piperazinyl and tetrahydropyranyl. It can be substituted by one, two or more identical or different substituents as defined for the heterocyclic radicals above. Preferably, it is unsubstituted or substituted by lower alkyl.

Heterocyclic-lower alkyl represents preferably straight chain or branched heterocyclic-$C_1$–$C_4$-alkyl in which heterocyclic has the meaning as defined above, e.g. 2-, 3- or 4-piperidyl methyl or (2-, or 3-morpholinyl)-(ethyl, propyl or butyl).

$C_3$–$C_7$-Cycloalkyl represents a saturated cyclic hydrocarbon unsubstituted or substituted by lower alkyl which contains 3 to 7 ring carbons and is advantageously cyclopentyl or cyclohexyl unsubstituted or substituted by lower alkyl.

Cycloalkyl-lower alkyl represents preferably (cyclopentyl- or cyclohexyl)-(methyl or ethyl).

A lower alkoxy (or alkyloxy) group preferably contains 1–4 carbon atoms, advantageously 13 carbon atoms, and represents for example, ethoxy, propoxy, isopropoxy, or most advantageously methoxy.

A lower alkylthio-group preferably contains 1–4 carbon atoms, advantageously 1–3 carbon atoms, and represents for example, ethylthio, propylthio, isopropylthio, or most advantageously methylthio.

A lower alkylsulfinyl-group preferably contains 1–4 carbon atoms, advantageously 1–3 carbon atoms, and represents for example, ethylsulfinyl, propylsulfinyl, isopropylsulfinyl, or most advantageously methylsulfinyl.

A lower alkylsulfonyl-group preferably contains 1–4 carbon atoms, advantageously 1–3 carbon atoms, and represents for example, ethylsulfonyl, propylsulfonyl, isopropylsulfonyl, or most advantageously methylsulfonyl.

A lower acyloxy group contains preferably 1–4 carbon atoms, and represents for example, acetoxy, propanoyloxy or butanoyloxy.

Prodrug acyl derivatives are preferably those derived from an organic carbonic acid, an organic carboxylic acid or a carbamic acid.

An acyl derivative which is derived from an organic carboxylic acid is, for example, lower alkanoyl, phenyl-lower alkanoyl or unsubstituted or substituted aroyl, such as benzoyl.

An acyl derivative which is derived from an organic carbonic acid is, for example, alkoxycarbonyl which is unsubstituted or substituted by an aromatic radical or is cycloalkoxy-carbonyl which is unsubstituted or substituted by lower alkyl.

An acyl derivativ which is derived from a carbamic acid is, for example, amino-carbonyl which is substituted by lower alkyl, aryl-lower alkyl, aryl, lower alkylene or lower alkylene interrupted by O or S.

Acylamino represents preferably lower alkanoylamino or lower alkoxycarbonylamino.

$C_1$–$C_3$ alkylen can be for example methylen, ethylen, 1,2-dimethylethylen, 1,1-dimethylethylen, propylen, 1,2-dimethylpropylen, 2,2-diethylpropylen or 1-methyl-2-ethylpropylen. $C_1$–$C_3$ alkylen is preferably unsubstituted. Most preferably it represents methylen or ethylen.

$C_2$–$C_7$-alkyl radical R is branched or unbranched, contains 2 to 7 carbon atoms and is preferably mono- or disubstituted by halogen, nitro, lower acyloxy, trifluoromethoxy, cyano, $C_3$–$C_5$-cycloalkyl or $C_3$–$C_6$-heteroaryl comprising one or two heteroatoms selected from the group consisting of O, S and N which is unsubstituted or substituted by lower alkyl. More preferably it is monosubstituted by halogen, most preferably by chloro or fluoro, $C_3$–$C_5$-cycloalkyl, most preferably cyclopropyl, or unsubstituted $C_3$–$C_6$-heteroaryl comprising one or two heteroatoms, in particular one heteroatom, selected from the group consisting of O, S and N, for example furyl, thienyl, pyrrolyl, imidazolyl, oxazolyl, thiazolyl or pyridinyl. $C_2$–$C_7$-alkyl radical R represents for example 7-fluoroheptyl, 7-chloroheptyl, 6-fluorohexyl, 6-chlorohexyl, 5-chloropentyl, 5-nitropentyl, 5-cyanopentyl, 5-fluoropentyl, 4-fluoropentyl, 5,5,5-trifluoropentyl, 5-acetoxypentyl, 4-chlorobutyl, 4-fluorobutyl, 3-fluorobutyl, 4,4,4-trifluorobutyl, 3,4-dichlorobutyl, 4,4-difluorobutyl, 4-acetoxybutyl, 4-propionyloxybutyl, 4-nitrobutyl, 4-cyanobutyl, 4-trifluoromethoxybutyl, 3,4-dicyanobutyl, 4,4-dicyanobutyl, 4-acetyloxy-2,2-dimethylbutyl, 4-fluoro-1-methylbutyl, 1-ethyl-4-fluorobutyl, 3-chloropropyl, 3-fluoropropyl, 2-fluoropropyl, 3-cyanopropyl, 3-trifluoromethoxypropyl, 2,3-dichloropropyl, 3-chloro-1,2-dimethylpropyl, 2-chloro-3-fluoropropyl, 3-cyano-1,2-dimethylpropyl, 2-cyano-3-fluoropropyl, 2-nitro-3-fluoropropyl, 2-cyano-3-chloropropyl, 3,3,3-trifluoropropyl, 2-chloroethyl, 2-fluoroethyl, 2-cyanoethyl, 2-cyclopropylethyl, 3-cyclopropylbutyl, 2-cyclobutylethyl, cyclopropylmethyl, cyclobutylmethyl, 3-furylmethyl or 2-(3-furyl)ethyl. Preferably $C_2$–$C_7$-alkyl radical R contains 3–5 carbon atoms and is unbranched. Preferably the substituents are located in terminal position. Most preferably $C_2$-alkyl radical R represents 4-chlorobutyl, 4-fluorobutyl, 3-chloropropyl or 3-fluoropropyl.

$C_3$–$C_7$-alkenyl radical R can be branched or unbranched and contains 3 to 7 carbon atoms. $C_3$–$C_7$-alkenyl radical R represents for example 2-propenyl, 2-chloromethyl-2-propenyl, 3-butenyl, 2-butenyl, 4-chloro-2-butenyl, 4-fluoro-2-butenyl, 4-acetoxy-2-butenyl, 2-isobutenyl, 2-pentenyl, 3-pentenyl, 5-chloro-2-pentenyl, 5-fluoro-3-pentenyl, 5-nitro-3-pent nyl, 4-pentenyl, 5-hexenyl, 3-chloro-5-hexenyl, 4-hexenyl or 6-heptenyl. Preferably $C_3$–$C_7$-alkenyl radical R contains 3–5 carbon atoms and is unsubstituted. The double bond is preferably located in terminal position. Preferably $C_3$–$C_7$-alkenyl radical R represents 4-pentenyl, 3-butenyl or 2-propenyl, most preferably 3-butenyl.

$C_3$–$C_7$-alkynyl radical R can be branched or unbranched and contains 3 to 7 carbon atoms. Preferably $C_3$–$C_7$-alkynyl radical R contains 3–5 carbon atoms and is unsubstituted. $C_3$–$C_7$-alkynyl radical R represents for example 2-propynyl, 2-butynyl, 4-cyano-2-butynyl, 4-nitro-2-butynyl, 3-butynyl, 5-chloro-2-pentynyl, 2-pentynyl, 5-fluoro-3-pentynyl, 5-chloro-3-pentynyl, 3-pentynyl, 4-hexynyl or 4-heptynyl, preferably it represents 2-propynyl, 2-butynyl, 2-pentynyl or 3-pentynyl. Preferably the triple bond is located in terminal position. In particular, good results can be obtained with compounds in which R is 2-propynyl.

Pharmaceutically acceptable salts of the acidic compounds of the invention are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris-(hydroxymethyl)-methylammonium salts.

Similarly acid addition salts, such as of mineral acids, organic carboxylic and organic sulfonic acids e.g. hydrochloric acid, methanesulfonic acid, maleic acid, are also possible provided a basic group, such as pyridyl, constitutes part of the structure.

The compounds of formula I have valuable pharmacologically useful properties. In particular, they display specific inhibitory actions which are of pharmacological interest.

The members of the enzyme family of matrix-degrading metalloproteinases (MMP's), such as gelatinase, stromelysin and collagenase, are implicated in various biological processes, e.g. tissue matrix degradation (e.g. collagen collapse) and in many pathological conditions involving abnormal connective tissue and basement membrane matrix metabolism, such as arthritis (e.g. osteoarthritis and rheumatoid arthritis), tissue ulceration (e.g. corneal, epidermal and gastric ulceration), abnormal wound healing, periodontal disease, bone disease (e.g. Paget's dis ase and osteoporosis), tumor metastasis or invasion, psoriasis, as well as HIV-infection (J. Leuk. Biol. 52 (2): 244–248, 1992), artherosclerosis, ventricular dilatation and restenosis in angioplasty.

Macrophage metalloelastase is a further matrix-degrading metalloproteinase which is involved in the degradation of elastin and has been implicated in pathological conditions, e.g. pulmonary disorders such as emphysema and COPD (chronic obstructive pulmonary disease).

Selectivity is generally an advantageous feature of pharmacologically active compounds, because the side-effects of drugs comprising selective compounds are smaller compared with drugs comprising less selective compounds. Since the family of MMP's consists of several different enzymes which are involved in different biological processes, it is desirable to have selective inhibitors of singular MMP's or subgroups of the MMP enzyme family.

The compounds of formula I and their pharmaceutically acceptable salts inhibit matrix degrading metalloproteinase such as gelatinase, stromelysin, and macrophage metalloelastase, and membrane type matrix metalloproteinases, such as MT1-MMP and MT2-MMP. They are particularly useful as MT1-MMP and MMP2 (gelatinase A) inhibitors.

A number of peptides are reported to interact with biological matter like enzymes, cells or receptors implicated in pathological processes or diseases. Peptides have the disadvantage to get easily hydrolyzed under physiological conditions, especially those physiological conditions to be found in the blood or stomach of warm-blooded animals. The compounds of formula I have the advantage to be no peptides. The compounds of formula I are non-peptide MMP2 inhibitors.

Beneficial effects are evaluated in pharmacological tests generally known in the art, and as illustrated herein.

The above-cited properties are demonstrable in in vitro and in vivo tests, using advantageously mammals, e.g. rats, guinea pigs, dogs, rabbits, or isolated organs and tissues, as well as mammalian enzyme preparations. Said compounds can be applied in vitro in the form of solutions, e.g. preferably aqueous solutions, and in vivo either enterally or parenterally, advantageously orally, e.g. as a suspension or in aqueous solution. Th dosage in vitro may range between about $10^{-5}$ molar and $10^{-10}$ molar concentrations. The dosage in vivo may range, depending on the route of administration, between about 0.1 and 100 mg/kg.

Antiinflammatory activity can be determined in standard inflammation and arthritic animal models well-known in the art, e.g. the adjuvant arthritis model in rats and the collagen II induced arthritis model in mice (Mediators of Inflam. 1, 273–279 (1992)).

One test to determine the inhibition of stromelysin activity is based on its hydrolysis of Substance P using a modified procedure of Harrison et al (Harrison, R. A., Teahan J., and Stein R., Anal. Biochem. 180, 110–113 (1989)). In this assay, Substance P is hydrolyzed by recombinant human stromelysin to generate a fragment, Substance P 7-11, which can be quantitated by HPLC. In a typical assay, a 10 mM stock solution of a compound to be tested is diluted in the assay buffer to 50 mM, mixed 1:1 with 8 mg recombinant human stromelysin (mol. wt. 45–47 kDa, 2 Units; where 1 Unit produces 20 mmoles of Substance P 7-11 in 30 minutes) and incubated along with 0.5 mM Substance P in a final volume of 0.125 mL for 30 minutes at 37° C. The reaction is stopped by adding 10 mM EDTA and Substance P 7-11 is quantified on RP-8 HPLC. The $IC_{50}$ for inhibition of stromelysin activity and Ki are calculated from control reaction without the inhibitor.

The effect of compounds of the invention in-vivo can be determined in rabbits. Typically, four rabbits are dosed orally with a compound up to four hours before being injected intra-articularly in both knees (N=8) with 40 Units of recombinant human stromelysin dissolved in 20 mM Tris, 10 mM $CaCl_2$, and 0.15 M NaCl at pH 7.5. Two hours later the rabbits are sacrificed, synovial lavage is collected, and keratan sulfate (KS) and sulfated glycosaminoglycan (S-GAG) fragments released into the joint are quantitated. Keratan sulfate is measured by an inhibition ELISA using the method of Thonar (Thonar, E. J.-M. A., Lenz, M. E., Klinsworth, G. K., Caterson, B., Pachman, L. M., Glickman, P., Katz, R., Huff, J., Keuttner, K. E., Arthr. Rheum. 28, 1367–1376 (1985)). Sulfated glycosaminoglycans are measured by first digesting the synovial lavage with *streptomyces* hyaluronidase and then measuring DMB dye binding using the method of Goldberg (Goldberg, R. L. and Kolibas, L, Connect. Tiss. Res. 24, 265–275 (1990)). For an i.v. study, a compound is solubilized in 1 mL of PEG-400, and for a p.o. study, a compound is administered in 5 mL of fortified corn starch per kilogram of body w ight.

Macrophage metalloelastase (MME) inhibitory activity can be determined by measuring the inhibition of the degradation of [$^3$H]-elastin by truncated recombinant mouse macrophage metalloelastase as follows:

About 2 ng of recombinant truncated mouse macrophage metalloelastase (FASEB Journal Vol. 8, A151, 1994), purified by Q-Sepharose column chromatography is incubated with test compounds at the desired concentrations in the presence of 5 nM $CaCl_2$, 400 nM NaCl, [$^3$H]elastin (60,000 cpm/tube), and 20 mM Tris, pH 8.0, at 37° C. overnight. The samples are spun in a microfuge centrifuge at 12,000 rpm for 15 minutes. An aliquot of the supernatant is counted in a scintillation counter to quantitate degraded [$^3$H]elastin. $IC_{50}$'s are determined from a range of concentrations of the test compounds and the percent inhibition of enzyme activity obtained.

The inhibitory activities of compounds of formula I on MT1-MMP, MMP1 (collagenase 1) and MMP2 (gelatinase A) can be determined as follows:

Stock solutions of substrate (MCA-Pro-Leu-Gly-Leu-Dpa-Ala-Arg-$NH_2$, Knight, C. G., Willenbrock, F., Murphy, G., A novel coumarin-labelled peptide for sensitive continous assays of the matrix metalloproteinases, FEBS lett., 296, 263–266, (1992)), are prepared in 100% DMSO at a concentration 1.0 mM. Stock solutions of inhibitors are prepared in 100% DMSO. The inhibitor is diluted into the assays from a solution in 100% DMSO, and controls substitute an equal volume of DMSO so that the final DMSO concentration from inhibitor and substrate dilutions in all assays is 6.0%. Assays are performed in assay buffer (150 mM NaCl, 10 mM $CaCl_2$, 50 mM Tris-Cl pH 7.5, 0.05% Brij-35) containing 6.0% DMSO once th substrate and inhibitor are diluted into it. The substrate concentration used in the assays is 10 µM. The test is carried out at 37° C. The fluorescence changes are monitored using an excitation wavelength of 320 nm and an emission wavelength of 340 nm. The reaction mixture is added in duplicate to appropriate wells of a 96 well microfluor plate. The reaction mixture is preincubated with the inhibitor for 30 min, the reaction is started by the addition of MMP enzyme and the fluorescence intensity is measured for 10 min. A time point that is on a linear part of the curve is chosen to determine the activity. The inhibition results are expressed as the inhibitor concentrations that produced 50% inhibition ($IC_{50}$) of the activity in the control (non-inhibited) reaction. In this test, the compounds of the formula I and their pharmacologically acceptable salts have an inhibiting concentration $IC_{50}$ [µmol/liter] of 0.0001 and 0.030, usually of 0.0002 to 0.0010, for MMP2 and an inhibiting concentration $IC_{50}$ [µmol/liter] of 0.0005 and 0.125, usually of 0.001 to 0.05, for MT1-MMP. Compounds of formula I exhibit an inhibiting concentration $IC_{50}$ for MMP1 (collagenase 1) that is up to 1000-fold higher than the $IC_{50}$ for MT1-MMP, generally it is about 40-fold to 200-fold higher. Compounds of formula I exhibit an inhibiting concentration $IC_{50}$ for MMP1 that is up to 5000-fold higher than the $IC_{50}$ for MMP2, for most compounds of formula I it is about 100-fold to 2000-fold higher.

The enzyme used in the above test are prepared as follows:

MT1-MMP:

Plasmid: The catalytic domain of the cDNA fragment encoding a full length of human MT1-MMP gene [from Prof. Motoharu Seiki, Institute of Medical Science, The University of Tokyo; Sato, H., Takino, T., Okada, Y., Cao, J., Shinagawa, A., Yamamoto, E. and Seiki, M. Nature (London), 370:61–65, 1994] is amplified by polymerase chain reaction (PCR). The primers used are follows: CTCCATAT-GTACGCCATCCAGGGTCTCAA for the sense primer including an NdeI site at the 5'-end for an ATG start codon, and CTCGGATCCTCACCCAT AAAGTTGCTGGAT-GCC for the antisense primer possessing a BamHI site with one TGA stop codon (1). The resulting PCR product of a 519-bp fragment is subcloned between the NdeI and BamHI unique sites of pET11a (Stratagene). The sequence of catalytic domain of MT1-MMP (CD-MT1-MMP) is verified by the ABI PRISM™ dye terminator cycle sequencing kit with the ABI PRISM™ 377 DNA sequencer (Perkin Elmer).

Expression and Purification: The subcloned CD-MT1-MMP is used to transfect *E. coli* strain BL21[DE3] (Hanahan, D. J. Mol. Biol. 1983;166(4):557–80) and expressed as insoluble inclusion body materials. Transfectants are grown at 37° C. in 50 ml Luria-Bertani (LB) medium in the presence of 50 g/ml ampicillin to a cell density of OD600=0.6–1.0, and CD-MT1-MMP production is induced with 1 mM isopropyl-1-D-galactopyranoside (IPTG). After treatments with 5 mg/ml lysozyme and 10 µg/ml DNase I, the inclusion bodies are prepared from the harvested cells by using the detergent buffer containing 0.2 M NaCl, 1% w/v deoxycholic acid, and 1% v/v Nonidet P-40. The solubilization is achieved by resuspending the inclusion bodies in the solubilization buffer composed of 6 M urea, 100 mM 2-mercaptoethanol, and 20 mM Tris-Cl, pH8.5. The enzyme is purified and r naturated using 10 ml of a Q-Sepharose (Amersham Pharmacia Biotech) column equilibrated with 5 mM $CaCl_2$, 0.02% v/v $NaN_3$, in 20 mM Tris-Cl pH7.5. After washing with three volumes of the same buffer, the bound proteins are eluted with two volumes of a linear gradient of 0.5–1.0 M NaCl. The collected fractions (1 ml each) are dialyzed for 6 h in equilibrated buffer. Superdex G200 column (1×15 cm) (Amersham Pharmacia) is equilibarated in 20 mM Tris-Cl, pH 7.5, 5 mM $CaCl_2$, 0.02% $NaN_3$. The desalted sample is applied to Superdex G200 column and chromatographed at 0.5 ml/min. Fractions of 1 ml are collected and 30 ml aliquots are analyzed by immunoblotting. Fractions showing the highest purity are pooled, concentrated in an Amicon stirred cell with a YM2 membrane and stored at −80° C. The eluted protein is dialyzed twice against 5 L buffer of 5 mM $CaCl_2$, 0.5 mM $ZnSO_4$, 20 mM Tris-Cl pH7.5, then concentrated in an Amicon stirred cell with a YM2 membrane. Under these conditions, the recombinant proteins remain soluble and are correctly folded.

MMP1 (Collagenase 1)

Plasmid: The cDNA for human collagenase is generated by PCR of cDNA derived from RNA isolated from human U937 cells (ATCC# CRL-2367). The primers, used to generate this cDNA, are AAGAAGCTTAAGGCCAGTATG-CACAGCTTTCCT and AAGGCGGCCGCA CACCT-TCTTTGGACTCACACCA, corresponding to nucleotides 58 to 1526 of the reported cDNA sequence, GenBank accession number X05231. The resulting cDNA fragment is subcloned into Not I site of a mammalian expression vector pBPV-MMT (Matthias, P. et al., J. Mol. Biol. 1986, 187(4): 557–68).

C127 cells (ATCC-mouse mammary tumor cell line) are grown in Dulbecco's Modified Essential Medium supplemented with 10% heat inactivated fetal bovine serum and 1× antibiotic-antimycotic solution at 37° C. in a humidified $CO_2$ incubator. Cells seeded at $8 \times 10^5$ in 100 mm dishes are transfected using a calcium phosphate precipitation method. 5 h prior to transfection, medium is replaced with fresh medium. Each dish is transfected with 15 µg of the expression vector. Cells ire washed twice with PBS 16–18 h after transfection and are incubated in growth medium for an additional 48 h. Clones are then selected by incubation with the Neomycin related antibiotic G418 at a concentration of 400 µg/ml. Media from selected clones are analyzed for collagenase expression by an enzymatic assay. Expression and Purification: 16 liters of culture medium are concentrated to 1.6 liters and the enzyme is isolated by the procedures described by Wilhelm et al. (Proc. Natl. Acad. Sci. (USA). 1987; 84: 6725–29). The final product is further purified on a Superos G-75 (Pharmacia/LKB, Piscataway, N.J.) gel filtration column equilibrated in the assay buffer containing 0.15 M NaCl. Enzyme is pooled and stored in aliquots at −70° C. Recombinant procollagenase (43–45 kDa) is activated with 1 mM APMA (Aminophenylmercuric acetate, ICN Pharmaceuticals) for 2 h at 37° C., and the APMA is removed by extensive dialysis against the assay buffer containing 0.15M NaCl. The activated enzyme (~36-kDa) is stored frozen at −70° C. until use.

MMP2 (Gelatinase A)

Plasmid: The cDNA for human proMMP2 is supplied by Prof. Motoharu Seiki, Institute of Medical Science, The University of Tokyo. The cDNA encoding a full length on human proMMP2 is generated by PCR of cDNA derived from RNA isolated from human HT1080 cells (ATCC# CCL121). The primers to generate this cDNA are GAAT-TCGATGGAGGCG CTAATGGCCCGG and CTCGAGT-CAGCAGCCTAGCCAGTCGGATTTGAT corresponding to full length human pro-MMP2 of the reported cDNA sequence, GenBank accession number J03210. The resulting 2.0 Kb PCR fragment is cloned into EcoR1/Xho 1 site of pFAST BAC 1 vector (pBAC-MMP2) (Collier, I. E., Wilhelm, S. M., Eisen, A. Z., Marmer, B. L., Grant, G. A., Seltzer, J. L., Kronberger, A., He, C., Bauer, E. A. and Goldberg, G. I. J. Biol. Chem., 263:6579–6587, 1988).

Expression and Purification: For baculovirus expression of r-proMMP2, pBAC-MMP2 is transformed into DH10BAC competent cells to produce a r-proMMP2 bacmid DNA. The recombinant bacmid DNA is transfected into cultured insect cells (Tn cells) with Cellfectin reagent (Gibco BRL). Recombinant baculovirus are plaque purified to homogeneity and are used to generate high titer stocks of the recombinant baculovirus. Expression of r-proMMP2 is confirmed by gelatin zymography.

Culture fluids of Tn cells infected with baculovirus are centrifuged and filtrated through a 0.22 mm pore size filter to remove cell debris. The recombinant proMMP2 as absorbed to gelatin Sepharose 4B (Pharmacia Biotech) in equilibration buffer of in 25 mM Tris-HCl (pH 7.5), 1 M NaCl, 10 mM $CaCl_2$, 0.05% Briji 35 at 4° C. After washing the beads with equilibration buffer, r-proMMP2 as eluted with equilibration buffer containing 10% DMSO. The enzyme are stored at 4° C. until activation. For assay, the purified proMMP2 is activated with 1 mM APMA for 1 hr at 37° C.

MMP9

MMP9 is prepared form the culture medium of THP1 human monocytic leukemia c lls treated with TPA. THP1 cells are maintained in a culture of DMEM/F-12 with 10% FCS and stimulated to produce pro-MMP9 with TPA (1 nM) in serum-free medium for 48 h. All purification procedures are carried out at 4° C. The 1 liters of culture medium is concentrated to 100 ml by Centricon (Amicon) and applied to a column (1×8 cm) of gelatin-sepharose (Pharmacia) equilibrated with 50 mM Tris-Cl (pH=8.0), 300 mM NaCl. The fraction containing pro-MMP-9 is eluted with 10% DMSO in 50 mM Tris-Cl (pH=8.0), 300 mM NaCl, then dialyzed against 50 mM Tris-Cl (pH 7.5), 150 mM NaCl. The fraction is concentrated by Centricon and subjected to column chromatography of Sephadex G200 (2×20 cm) equilibrated with 50 mM Tris-Cl (pH=7.5) containing 150 mM NaCl. The purified Pro-MMP9 is stored at −80° C. as a stock and the necessary amount of pro-form is used for activation. Pro-MMP9 is activated with 1 mM aminophenyl mercury acetate (APMA, ICN Pharmaceuticals) in 50 mM Tris-Cl (pH=7.5) containing 150 mM NaCl, 10 mM $CaCl_2$ and 0.05% Brij-35 (MMP Assay Buffer) for 18 h at 37° C., and the APMA is removed by extensive dialysis against MMP Assay Buffer. The activated MMP9 is stored frozen at −80° C. until use.

Assay of MMP9

The activated MMP-9 (82 kDa) is then used to screen compounds. A fluorogenic peptide, 2-N-methylaminobenzoic acid (Nma)-Gly-Pro-Gln-Gly-Leu-Ala-Gly-Gln-Lys-Nε-(2,4-dinitrophenyl)(Dnp)-$NH_2$ (Peptide Institute, Osaka, Japan) is used as the only substrate in all MMPs assay in this study at 25 µM. Stock solutions of the substrate are prepared in 100% DMSO at a concentration 1.0 mM. Assays are performed in MMP Assay Buffer. The reaction mixture is added in duplicate to appropriate wells of a 96 well microfluor plate and preincubated at 37° for 30 min. The reaction is started by the addition of 0.5 nM of activated MMP9. Stock solutions of each inhibitor are prepared by dissolving in 100% DMSO. Inhibitors are added into the assay mixture from the diluted solution with 100% DMSO prepared from the stock solutions. An equal volume of DMSO is added to controls. The final concentration of DMSO from inhibitor and substrate solutions is 5.0%. The increase of fluorescence is monitored at 460 nm with excitation at 355 nm. A time point on a linear part of the curve is chosen to determine the activity. The inhibition results are expressed as the inhibitor concentration that produce 50% inhibition ($IC_{50}$) of the activity in the control reaction.

The anti-tumor effect of compounds of formula I can also be demonstrated .g. in vivo in metastasis models using EGFP transfected HT1080 cells measuring the fluorescence intensity of tumor cells metastasized into the lung of nude mice with intravenously injected tumor cells or using B16-F10 melanoma cells measuring lung tumor nodules after i.v. injection of tumor cells into BDF1 mice.

EGFP transfected HT1080: Nude mice were injected in the tail vein a suspension of tumor cells [$2 \times 10^6$ cells/0.1 ml of PBS (phosphate buffered saline)]. Animals were dosed with compounds p.o. at −1 hr and +5 hrs relative to the time of the cell injection at the first day (day 0). After that the animals were dosed twice a day, firstly at 9–10:30 a.m. and secondly at 5:30–7:00 p.m. Compounds were administered as a suspension in 1% carboxymethyl cellulose (Wako, Japan) at a dose of 60 mg/kg twice a day. The vehicle alone was administered to the control group. On day 17, the lungs were removed from mice after sacrificing the animals. The removed lung tissues were divided into pieces of approximately 2–3 mm in diameter and then ca. 100 mg of tissues were suspended in 0.2 ml PBS in the microcentrifuge tubes followed by gentle homogenization and centrifugation. The cells were washed 3 times with 1 ml of lysing reagent (150 mM $NH_4Cl$, 0.1 mM EDTA-4 Na, 10 mM $KHCO_3$ pH7.4) to lysis red blood cells and 2 times with 1 ml of PBS at room temperature. After the final wash, the cells were lysed with 0.5 ml of 1% Triton in PBS. After centrifugation at 15000 rpm for 5 min, 0.23 ml of each supernatants w transferred into the well of a 96-well multi plate. The fluorescence intensity w determined by using fluorescence plate reader (Cytoflour II) at the excitation and emission wavelength of 485 and 530 nm, respectively. The obtained fluorescence was normalized per lung using the wet lung weight. In this test a decrease in the fluorescence of 74% compared to the vehicle alone was determined for the compound of Example 68.

The B16-F10 melanoma experimental metastasis model was studied following the method of Fidler. Cells were harvested by trypsinization and washed once with serum-containing medium and three times with cold PBS and then kept on ice. Mice were injected in the tail vein with a suspension of tumor cells ($2 \times 10^5$ cells/0.1 ml of PBS). Animals were dosed with compounds p.o. at −1 hr, +5 hrs, 23 hrs and 29 hrs relative to the time of the cell injection at the first two days (day 0, 1). After that the animals were dosed once a day in the morning. Compounds were administered as a suspension in 1% carboxymethyl cellulose (Wako, Japan) at a dose of 120 mg/kg/dosing. Vehicle alone was administered to the control group. On day 14, the lung of the mice were removed after sacrificing the animals and the numbers of th tumor nodules were counted manually aft r fixing with Bouin's solution (2% picric acid in destilled water: 10% formaldehyde neutral buffer solution: acetic acid=15:5:1). In this test a decrease in the number of tumor nodules of 47% compared to the vehicle alone was determined for the compound of Example 68.

The antitumor effect of the compounds of the invention can be determined e.g. by measuring the growth of human tumors implanted subcutaneously in Balb/c nude treated mice according to methodology well-known in the art in comparison to placebo treated mice. Illustrative tumors are e.g. estrogen dependent human breast carcinoma BT20 and MCF7, human bladder carcinoma T24, human colon carcinoma Colo 205, human lung adenocarcinoma A549 and human ovarian carcinoma NIH-OVCAR3.

The effect on tumor angiogenesis can be determined e.g. in rats implanted with Walker 256 carcinoma in pellets to stimulate angiogenesis from vessels of the limbus, as described by Galardy et al, Cancer Res. 54, 4715 (1994).

The compounds of the formula I inhibit matrix degradation and are therefore very highly suitable for the treatment of diseases which respond to inhibition of the activity of the enzymes MT1-MMP and MMP2. Osteoporosis, in particular, can be mentioned here, and also other diseases in whose course bone resorption by osteoclasts play a part, e.g. tumor-induced hypercalcaemia, Paget's Disease or the treatment of bone metastases, and also inflammatory processes in joints and bones and degeneratives processes in cartilaginous tissue. In particular, the compounds of formula I are useful for the treatment of benign or malignant tumours which respond to inhibition of the enzymes MT1-MMP and MMP2, e.g breast, lung, bladder, colon, ovarian, brain, and skin cancer by inhibiting tumor growth, tumor metastasis, tumor progression or invasion and/or tumor angiogenesis. They are able to cause tumour regression and to prevent the growth of micrometastases.

Other conditions to be treated with the compounds of the invention include rheumatoid arthritis, osteoarthritis, bronchial disorders (such as asthma by inhibiting the degradation of elastin), atherosclerotic conditions (by e.g. inhibiting rupture of atherosclerotic plaques), as well as acute coronary syndrome, heart attacks (cardiac ischemia), strokes (cerebral ischemia), restenosis after angioplasty, and also vascular ulcerations, ectasia and aneurysms. Furth r conditions to b treated with the compounds of the invention are inflammatory demyelinating disorders of the nervous system in which myelin destruction or loss is involved (such as multiple sclerosis), optic neuritis, neuromyelitis optica (Devic's disease), diffuse and transitional sclerosis (Schilder's disease) and acute disseminated encephalomyelitis, also demyelinating peripheral neuropathies such as Landry-Guillain-Barre-Strohl syndrome for motor defects; also tissue ulceration (e.g. epidermal and gastric ulceration), abnormal wound healing and periodental disease. Also endometriosis, septic shock, inflammatory bowel disease, Crohn's disease and the like can be treated by the compounds of formula I.

Ocular applications of the compounds of the invention include the treatment of ocular inflammation, corneal ulcerations, pterygium, keratitis, keratoconus, open angle glaucoma, retinopathies, and also their use in conjunction with refractive surgery (laser or incisional) to minimize adverse effects.

Certain metalloproteinase inhibitors have been reported to also inhibit the production and release of tumor necrosis factor (TNF), e.g. TNF-α which is an important mediator of inflammation. Thus, compounds of the invention are potential anti-inflammatory agents in mammals.

The effect of the compounds of the invention on atherosclerotic conditions can be evaluated using atherosclerotic plaques from cholesterol-fed rabbits which contain activated matrix metalloproteinases as described by Sukhova et al, Circulation 90, 1404 (1994). The inhibitory effect on matrix metalloproteinase enzyme activity in rabbit atherosclerotic plaques can be determined by in situ zymography, as described by Galis et al, J. Clin. Invest. 94, 2493 (1994), and is indicative of plaque rupture.

The effect on vascular aneurysms, e.g. the inhibition of aneurysm formation, can be determined in experimental models such as Apo-E transgenic mice and/or LDL receptor knockout mice. Abdominal aortic aneurysms represent a chronic degenerative condition associated with a life-threatening risk of rupture. Aneurysm development can be suppressed by the compounds of formula I.

The effect on restenosis and vascular remodeling can be evaluated in the rat ballooned carotid artery model.

The effect on demyelinating disorders of the nervous system, such as multiple sclerosis, can be evaluated by measuring the reversal of experimental autoimmune encephalomyelitis in mice, e.g. as described by Gijbels et al, J. Clin. Invest. 94, 2177 (1994).

The invention relates especially to compounds of formula I, wherein $R^1$ is hydrogen, lower alkyl;

monocyclic or bicyclic carbocyclic aryl which is unsubstituted or mono-, di- or trisubstituted by lower alkyl, lower alkoxy, hydroxy, halogen, cyano, trifluoromethyl, phenoxy or phenyl which is unsubstituted or substituted by lower alkoxy, lower alkyl, halogen, cyano, nitro, trifluoromethyl or lower-alkylenedioxy;

mono- or bicyclic heterocyclic aryl which is unsubstituted or substituted by one, two or more identical or different substituents selected from the group consisting of free, etherified and esterified hydroxyl groups; mercapto, lower alkylthio, substituted and unsubstituted phenylthio groups, halogen, oxo groups, which are in the form of formyl and keto groups and corresponding acetals or ketals, azido, nitro, primary, secondary and tertiary amino, acylamino, diacylamino and unmodified or functionally modified sulfo groups; free and functionally modified carboxyl groups, carbamoyl, ureido, guanidino and cyano;

carbocyclic aryl-lower alkyl which is unsubstituted or mono-, di- or trisubstituted by lower alkyl, lower alkoxy, hydroxy, halogen, cyano, trifluoromethyl, phenoxy or phenyl which is unsubstituted or substituted by lower alkoxy, lower alkyl, halogen, cyano, nitro, trifluoromethyl or lower-alkylenedioxy in the carbocyclic moiety;

substituted or unsubstituted heterocyclic-lower alkyl which is unsubstituted or substituted by one, two or more identical or different substi tuents selected from the group consisting of free, etherified and esterified hydroxyl groups; mercapto, lower alkylthio, substituted and unsubstituted phenylthio groups, halogen, oxo groups, which are in the form of formyl and keto groups and corresponding acetals or ketals, azido, nitro, primary, secondary and tertiary amino, acylamino, diacylamino and unmodified or functionally modified sulfo groups; free and functionally modified carboxyl groups, carbamoyl, ureido, guanidino and cyano, in the heterocyclic moiety;

$C_3$–$C_7$-cycloalkyl, which is unsubstituted or substituted by lower alkyl;

$C_3$–$C_7$-cycloalkyl-lower alkyl, which is unsubstituted or substituted by lower alkyl; hydroxy-lower alkyl, lower alkoxy-lower alkyl, low r alkyl-(thio, sulfinyl or sulfonyl)-lower alkyl, amino-lower alkyl or mono- or di-lower alkylamino-lower alkyl;

$R^2$ is hydrogen or lower alkyl;

$R^3$ is $C_3$–$C_7$-cycloalkyl, which is unsubstituted or substituted by lower alkyl;

carbocyclic aryl, which is unsubstituted or mono-, di- or trisubstituted by lower alkyl, lower alkoxy, hydroxy, halogen, cyano, trifluoromethyl, phenoxy or phenyl which is unsubstituted or substituted by lower alkoxy, lower alkyl, halogen, cyano, nitro, trifluoromethyl or lower-alkylenedioxy;

heterocyclic aryl, which is unsubstituted or substituted by one, two or more identical or different substituents selected from the group consisting of free, etherified and esterified hydroxyl groups; mercapto, lower alkylthio, substituted and unsubstituted phenylthio groups, halogen, oxo groups, which are in the form of formyl and keto groups and corresponding acetals or ketals, azido, nitro, primary, secondary and tertiary amino, acylamino, diacylamino and unmodified or functionally modified sulfo groups; free and functionally modified carboxyl groups, carbamoyl, ureido, guanidino and cyano;

heterocyclyl, which is unsubstituted or substituted by one, two or more identical or different substituents selected from the group consisting of free, etherified and esterified hydroxyl groups; mercapto, lower alkylthio, substituted and unsubstituted phenylthio groups, halogen, oxo groups, which are in the form of formyl and keto groups and corresponding acetals or ketals, azido, nitro, primary, secondary and tertiary amino, acylamino, diacylamino and unmodified or functionally modified sulfo groups; free and functionally modified carboxyl groups, carbamoyl, ureido, guanidino and cyano;

or lower alkyl;

A is $C_1$–$C_3$ alkylen unsubstituted or substituted by lower alkyl;

q is 1–5; and

R is $C_2$–$C_7$-alkyl, which is mono-, di- or trisubstituted by halogen, nitro, lower acyloxy, trifluoromethoxy, cyano, $C_3$–$C_5$-cycloalkyl or $C_3$–$C_6$-heteroaryl comprising one or two heteroatoms selected from the group consisting of O, S and N, which is unsubstituted or substituted by lower alkyl; or $C_3$–$C_7$-alkenyl or $C_3$–$C_7$-alkynyl, which in each case is unsubstituted or mono-, di- or trisubstituted by halogen, nitro, lower acyloxy, trifluoromethoxy, cyano, $C_3$–$C_5$-Cycloalkyl or $C_3$–$C_6$-heteroaryl comprising one or two heteroatoms selected from the group consisting of O, S and N, which is unsubstituted or substituted by lower alkyl;

and their pharmaceutically acceptable prodrug derivatives; and pharmaceutically acceptable salts.

Preferred is a compound of formula I, wherein $R^1$ is hydrogen, substituted or unsubstituted aryl, lower alkyl, substituted or unsubstituted carbocyclic aryl-lower alkyl, substituted or unsubstituted heterocyclic-lower alkyl, substituted or unsubstituted $C_3$–$C_7$-cycloalkyl, substituted or unsubstituted $C_3$–$C_7$-cycloalkyl-lower alkyl, hydroxy-lower alkyl, lower alkoxy-lower alkyl, lower alkyl-(thio, sulfinyl or sulfonyl)-lower alkyl, amino-lower alkyl or mono- or di-lower alkylamino-lower alkyl;

$R^2$ is hydrogen or lower alkyl;

$R^3$ is substituted or unsubstituted $C_3$–$C_7$-cycloalkyl, substituted or unsubstituted carbocyclic aryl, substituted or unsubstituted heterocyclic aryl, or lower alkyl;

A is $C_1$–$C_3$ alkylen unsubstituted or substituted by lower alkyl;

q is 1–5;

R is $C_2$–$C_7$-alkyl, which is mono-, di- or trisubstituted by halogen, nitro, lower acyloxy, trifluoromethoxy or cyano; $C_3$–$C_7$-alkenyl or $C_3$–$C_7$-alkynyl, which in each case is unsubstituted or mono-, di- or trisubstituted by halogen, nitro, lower acyloxy, trifluoromethoxy or cyano;

and pharmaceutically acceptable prodrug derivatives; and pharmaceutically acceptable salts thereof.

Furthermore, a compound of formula I is preferred, wherein $R_1$ is hydrogen, lower alkyl, or carbocyclic aryl-lower alkyl which is unsubstituted or mono-, di- or trisubstituted by lower alkyl, lower alkoxy, hydroxy, halogen, cyano, trifluoromethyl, phenoxy or phenyl which is unsubstituted or substituted by lower alkoxy, lower alkyl, halogen, cyano, nitro, trifluoromethyl or lower-alkylenedioxy in the carbocyclic moiety;

$R_2$ is hydrogen or lower alkyl;

$R_3$ is $C_3$–$C_7$-cycloalkyl, which is unsubstituted or substituted by lower alkyl, carbocyclic aryl, which is unsubstituted or mono-, di- or trisubstituted by lower alkyl, lower alkoxy, hydroxy, di-lower alkyl amino, halogen, cyano, trifluoromethyl, phenoxy triazolyl, imidazolyl, morpholinyl, pyrrolidinyl, piperidinyl, tetrazolyl, pyrrolyl, furyl, thienyl, morpholinyl lower alkyl, quinolinyl lower alkyl, imidazolyl lower alkyl and triazolyl lower alkyl or phenyl which is unsubstituted or substituted by lower alkoxy, lower alkyl, halogen, cyano, nitro, trifluoromethyl or lower-alkylenedioxy;

heterocyclic aryl, which is unsubstituted or substituted by one, two or more identical or different substituents selected from the group consisting of free, etherified and esterified hydroxyl groups; mercapto, lower alkylthio, substituted and unsubstituted phenylthio groups, halogen, oxo groups, which are in the form of formyl and keto groups and corresponding acetals or ketals, azido, nitro, primary, secondary and tertiary amino, acylamino, diacylamino and unmodified or functionally modified sulfo groups; free and functionally modified carboxyl groups, carbamoyl, ureido, guanidino and cyano;

heterocyclyl, which is unsubstituted or substituted by one, two or more identical or different substituents selected from the group consisting of free, etherified and esterified hydroxyl groups; mercapto, lower alkylthio, substituted and unsubstituted phenylthio groups, halogen, oxo groups, which are in the form of formyl and keto groups and corresponding acetals or ketals, azido, nitro, primary, secondary and tertiary amino, acylamino, diacylamino and unmodified or functionally modified sulfo groups; free and functionally modified carboxyl groups, carbamoyl, ureido, guanidino and cyano; or lower alkyl;

A is $C_1$–$C_3$ alkylen unsubstituted or substituted by lower alkyl;

q is 1 or 2;

R is $C_2$–$C_7$-alkyl, which is mono-, di- or trisubstituted by halogen, nitro, lower acyloxy, trifluoromethoxy, cyano, $C_3$–$C_5$-cycloalkyl or $C_3$–$C_6$-heteroaryl comprising one or two heteroatoms selected from the group consisting of O, S and N, which is unsubstituted or substituted by lower alkyl; or $C_3$–$C_7$-alkenyl or $C_3$–$C_7$-alkynyl, which in each case is unsubstituted or mono-, di- or trisubstituted by halogen, nitro, lower acyloxy, trifluoromethoxy, cyano, $C_3$–$C_5$-cycloalkyl or $C_3$–$C_6$-heteroaryl comprising one or two heteroatoms selected from the group consisting of O, S and N, which is unsubstituted or substituted by lower alkyl;

and pharmaceutically acceptable prodrug derivatives; and pharmaceutically acceptable salts thereof.

The invention relates in particular to compounds of formula I, wherein $R_1$ is hydrogen, lower alkyl, or substituted or unsubstituted carbocyclic aryl-lower alkyl;

$R_2$ is hydrogen or lower alkyl;

$R_3$ is substituted or unsubstituted $C_3$–$C_7$-cycloalkyl, substituted or unsubstituted carbocyclic aryl, substituted or unsubstituted heterocyclic aryl, or lower alkyl;

A is $C_1$–$C_3$ alkylen unsubstituted or substituted by lower alkyl;

q is 1 or 2; and

R is $C_2$–$C_7$-alkyl, which is mono-, di- or trisubstituted by halogen, nitro, lower acyloxy, trifluoromethoxy or cyano; $C_3$–$C_7$-alkenyl or $C_3$–$C_7$-alkynyl, which in each case is unsubstituted or mono-, di- or trisubstituted by halogen, nitro, lower acyloxy, trifluoromethoxy or cyano.

Compounds of formula I which are preferred are those in which $R_1$ is hydrogen, lower alkyl, or substituted or unsubstituted carbocyclic aryl-lower alkyl;

$R_2$ is hydrogen or lower alkyl;

$R_3$ is substituted or unsubstituted $C_3$–$C_7$-cycloalkyl; phenyl which is unsubstituted or mono-or disubstituted by lower alkyl, lower alkoxy, hydroxy, nitro, amino, lower-alkyl amino, carbamoyl, trifluoromethyl, trifluoromethoxy, lower alkylthio, lower acyloxy or halogen; pyridyl, pyrimidyl, pyrryl, imidazolyl, indolyl, thienyl, benzothienyl, furyl, benzofuranyl, oxazolyl, thiazolyl; or lower alkyl;

A is $C_1$–$C_3$ alkylen unsubstituted or substituted by lower alkyl;

q is 1 or 2;

R is $C_2$–$C_7$-alkyl, which is mono-, di- or trisubstituted by halogen, nitro, lower acyloxy, trifluoromethoxy or cyano; $C_3$–$C_7$-alkenyl or $C_3$–$C_7$-alkynyl, which in each case is unsubstituted or mono-, di- or trisubstituted by halogen, nitro, lower acyloxy, trifluoromethoxy or cyano;

and their pharmaceutically acceptable prodrug derivatives and their pharmaceutically acceptable salts.

The invention relates in particular to compounds of formula I, wherein $R_1$ is hydrogen, lower alkyl, or phenyl lower alkyl;

$R_2$ is hydrogen or lower alkyl;

$R_3$ is phenyl which is unsubstituted or monosubstituted by lower alkyl, lower alkoxy, hydroxy, nitro, amino, lower-alkyl amino, carbamoyl, trifluoromethyl, lower alkylthio, or halogen; pyridyl, or lower alkyl;

A is $C_1$–$C_3$ alkylen unsubstituted or substituted by lower alkyl;

q is 1 or 2;

R is $C_2$–$C_7$-alkyl, which is mono-, di- or trisubstituted by halogen, nitro, lower acyloxy, trifluoromethoxy or cyano; unsubstituted $C_3$alkenyl or unsubstituted $C_3$–$C_7$-alkynyl; and their pharmaceutically acceptable prodrug derivatives and their pharmaceutically acceptable salts.

In particular, compounds of formula I are preferred, in which $R_1$ is hydrogen, lower alkyl, or phenyl lower alkyl;

$R_2$ is hydrogen;

$R_3$ is phenyl monosubstituted by lower alkoxy or halogen; or lower alkyl;

A is $C_1$–$C_3$ alkylen;

q is 1;

R is $C_2$–$C_7$-alkyl, which is mono- or trisubstituted by halogen; unsubstituted $C_3$–$C_7$-alkenyl or unsubstituted $C_3$–$C_7$-alkynyl;

and their pharmaceutically acceptable prodrug derivatives and their pharmaceutically acceptable salts.

One preferred embodiment of the invention relates to compounds of formula I, wherein $R_1$ is hydrogen;

$R_2$ is hydrogen;

$R_3$ is phenyl monosubstituted by lower alkoxy or halogen;

A is $C_1$–$C_3$ alkylen;

q is 1;

R is unsubstituted $C_3$–$C_5$-alkenyl, in which the double bond is terminally located; or unsubstituted $C_3$–$C_7$-alkynyl, in which the triple bond is terminally located; and to their pharmaceutically acceptable prodrug derivatives and their pharmaceutically acceptable salts.

Another preferred embodiment of the invention relates to compounds of formula I, wherein $R_1$ is hydrogen;

$R_2$ is hydrogen;

$R_3$ is phenyl monosubstituted by lower alkoxy or halogen;

A is methylen or ethylen;

q is 1;

R is unbranched $C_3$–$C_5$-alkyl, which is terminally monosubstituted by halogen; and to their pharmaceutically acceptable prodrug derivatives and their pharmaceutically acceptable salts.

Very preferred are compounds of formula I, wherein $R_1$ is hydrogen, lower alkyl, or phenyl lower alkyl;

$R_2$ is hydrogen;

$R_3$ is $C_3$–$C_7$-cycloalkyl, which is unsubstituted or substituted by lower alkyl; phenyl which is unsubstituted or mono- or disubstituted by lower alkyl, lower alkoxy, hydroxy, nitro, amino, lower alkyl amino, di-lower alkyl amino, carbamoyl, trifluoromethyl, trifluoromethoxy, lower alkylthio, lower acyloxy, halogen, triazolyl, imidazolyl, morpholinyl, pyrrolidinyl, piperidinyl, tetrazolyl, pyrrolyl, furyl, thienyl, morpholinyl lower alkyl, quinolinyl lower alkyl, imidazolyl lower alkyl, triazolyl lower alkyl;

pyridyl, pyrimidyl, pyrryl, imidazolyl, indolyl, thienyl, benzothienyl, furyl, benzofuranyl, oxazolyl, thiazolyl, which in each case are unsubstituted or substituted by lower alkyl or halogen;

heterocyclyl, which is unsubstituted or substituted by lower alkyl and which is selected from the group consisting of piperidinyl, morpholinyl, pyrrolidinyl, pyrrolinyl, piperazinyl and tetrahydropyranyl;

A is methylen or ethylen;

q is 1;

R is $C_2$–$C_7$-alkyl, which is mono-, di- or trisubstituted by halogen, nitro, lower acyloxy, trifluoromethoxy, cyano, $C_3$–$C_5$-cycloalkyl or $C_3$–$C_6$-heteroaryl comprising one or two heteroatoms selected from the group consisting of O, S, and N which is unsubstituted or substituted by lower alkyl; $C_3$–$C_7$-alkenyl or $C_3$–$C_7$-alkynyl, which in each case is unsubstituted or mono-, di- or trisubstituted by halogen, nitro, lower acyloxy, trifluoromethoxy, cyano; $C_3$–$C_5$-cycloalkyl or $C_3$–$C_6$-heteroaryl comprising one or two heteroatoms selected from the group consisting of O, S, and N, which is unsubstituted or substituted by lower alkyl and their pharmaceutically acceptable prodrug derivatives and pharmaceutically acceptable salts.

A more preferred embodiment of the invention relates to compounds of formula I, wherein $R_1$ is hydrogen, lower alkyl, or phenyl lower alkyl;

$R_2$ is hydrogen;

$R_3$ is phenyl which is unsubstituted or mono- or disubstituted by lower alkyl, lower alkoxy, di-lower alkyl amino, halogen, triazolyl, imidazolyl, morpholinyl, pyrrolidinyl, piperidinyl, tetrazolyl, pyrrolyl, furyl, thienyl, morpholinyl lower alkyl, quinolinyl lower alkyl, imidazolyl lower alkyl, triazolyl lower alkyl;

pyridyl, which is unsubstituted or substituted by haolgen;

heterocyclyl, which is unsubstituted and which is selected from the group consisting of piperidinyl, morpholinyl, pyrrolidinyl, pyrrolinyl, piperazinyl and tetrahydropyranyl;

A is methylen;

q is 1;

R is unsubstituted $C_3$–$C_5$-alkenyl, in which the double bond is terminally located;

unsubstituted $C_3$–$C_5$-alkynyl, in which the triple bond is terminally located; or unbranched $C_3$–$C_5$-alkyl, which is terminally monosubstituted or trisubstituted by halogen, or terminally monosubstituted by furyl or cyclopropyl;

and to pharmaceutically acceptable prodrug derivatives; and pharmaceutically acceptable salts thereof.

The compounds of the formula I and their pharmaceutically acceptable prodrug derivatives and pharmaceutically acceptable salts are prepared by processes known per se, for example a) by reacting a compound of the formula II

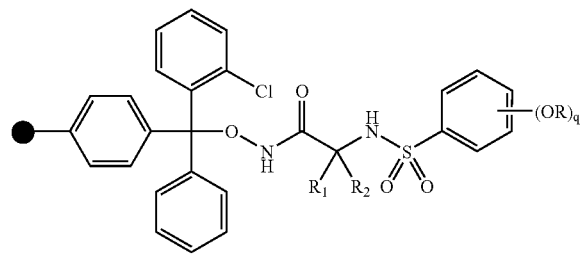

(II)

in which R, q, $R_1$ and $R_2$ are as defined above for compounds of the formula I and the black circular plane indicates that the compound is bound to a polymer resin, free functional groups present in the compound, if necessary, being protected by easily detachable protective groups, in a suitable solvent, e.g. tetrahydrofuran, first with triphenylphosphine, an alcohol of the structure III,

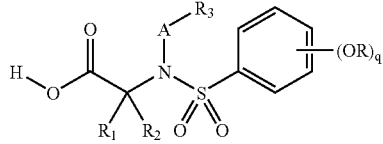

(III)

in which A and $R_3$ are as defined above for compounds of formula I, and diethyl azodicarboxylate, free functional groups present in this compound, if necessary, being protected by easily detachable protective groups or, in accordance with the principle of latent functionality, being in a form which can be converted into the functional groups and then to cleave the product of the reaction from the polymer resin by a further reaction with trifluoroacetic acid in a suitable solvent, e.g. dichloromethane, or b) by reacting a compound of the formula IV (IV)

in which R, q, A, $R_1$, $R_2$ and $R_3$ are as defined above for compounds of the formula I, free functional groups present in the compound, if necessary, being protected by easily detachable protective groups, in a suitable solvent, e.g. dichloromethane, first with oxalylchloride in dimethylformamide and then with hydroxylamine in a mixture of water and tetrahydrofuran, or c) by reacting a compound of the formula V (V)

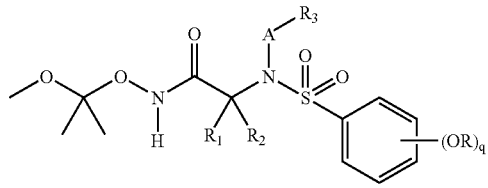

in which R, q, A, $R_1$, $R_2$ and $R_3$ are as defined above for compounds of the formula I, free functional groups present in the compound, if necessary, being protected by easily detachable protective groups, in a suitable solvent, .g. acetic acid ethyl ester, with aqueous hydrogenchloride and, after carrying out process a), b) or c) and detaching the protective groups present and, if necessary, converting functional groups into the final form according to formula I, if necessary for the preparation of a salt, converting a resulting free compound of the formula I into a salt or, if necessary for preparation of a free compound, converting a resulting salt of a compound of the formula I into the free compound.

Processes b) and c) are preferred for compounds of formula I in which $R_1$ and $R_2$ are both hydrogen at the same time.

The above processes are described in more detail below:

The end substances of the formula I can contain substituents which can also be used as protective groups in starting substances for the preparation of other end substances of the formula I. Unless otherwise evident from the context, "protective groups" in this text, are therefore only those easily detachable groups which are not a constituent of the particular desired end substance of the formula I.

Protective groups, their introduction and their detachment are described, for example, in "Protective Groups in Organic Chemistry", Plenum Press, London, New York 1973, and in "Methoden der organischen Chemie" [Methods of Organic Chemistry], Houben-Weyl, 4th Edition, Volume 15/1, Georg-Thieme-Verlag, Stuttgart 1974 and in T. W. Greene, "Protective Groups in Organic Synthesis", John Wiley & Sons, New York 1981. It is characteristic of protective groups that they can be detached easily, i.e. without undesirable side reactions taking place, for example by solvolysis, reduction, photolysis or also under physiological conditions.

Protection of free functional groups in the starting material of the formula II is as a rule not necessary. If desired, free carboxyl or amino groups in the radicals R, $R_1$, $R_2$ or $R_3$ of a compound of formula II, III, IV or V can be present in protected form. Functional groups, such as, in particular, leaving groups, for example halogen or toluenesulfonate, however, can also be present, in accordance with the principle of latent functionality, in a form which can be converted into one of the functional groups according to formula I. Thus, a protected amino group, e.g. incorporated in radical R, can first be set free by detaching the amino-protective group and the free amino group can then be converted into halogen via an azide in a manner known per se.

A protected amino group can be, for example, in the form of an easily detachable acylamino, arylmethylamino, etherified mercaptoamino or 2-acyl-lower alk-1-en-yl-amino group.

In a corresponding acylamino group, acyl is, for example, the acyl radical of an organic carboxylic acid having, for example, not more than 18 C atoms, in particular an alkanecarboxylic acid which is unsubstituted or substituted, for example by halogen or aryl, or of a benzoic acid which is unsubstituted or substituted, for example by halogen, lower alkoxy or nitro, or of a carbonic acid half-ester. Such acyl groups are, for example, lower alkanoyl, such as formyl, acetyl or propionyl, halo-lower alkanoyl, such as 2-haloacetyl, in particular 2-chloro-, 2-bromo-, 2-iodo-, 2,2,2-trifluoro- or 2,2,2-trichloroacetyl, benzoyl which is unsubstituted or substituted, for example by halogen, lower alkoxy or nitro, for example benzoyl, 4-chlorobenzoyl, 4-methoxybenzoyl or 4-nitrobenzoyl, or lower alkoxycarbonyl which is branched in the 1 position of the lower alkyl radical or suitably substituted in the 1 or 2 position, in particular tert-lower alkoxycarbonyl, for example tert-butyloxycarbonyl, arylmethoxycarbonyl with one or two aryl radicals, which are preferably phenyl which is unsubstituted or mono- or polysubstituted, for example by lower alkyl, in particular tert-lower alkyl, such as tert-butyl, lower alkoxy, such as methoxy, hydroxyl, halogen, for example chlorine, and/or nitro, such as unsubstituted or substituted benzyloxycarbonyl, for example 4-nitro-benzyloxycarbonyl, or unsubstituted or substituted diphenylmethoxycarbonyl, for example benzhydryloxycarbonyl or di-(4-methoxyphenyl)-methoxycarbonyl, aroylmethoxycarbonyl, in which the aroyl group is preferably benzoyl which is unsubstituted or substituted, for example by halogen, such as bromine, for example phenacyloxycarbonyl, 2-halo-lower alkoxycarbonyl, for example 2,2,2-trichloroethoxycarbonyl, 2-bromoethoxy-carbonyl or 2-iodoethoxycarbonyl, or 2-(trisubstituted silyl)-ethoxycarbonyl, in which the substituents independently of one another are each an aliphatic, araliphatic, cycloaliphatic or aromatic hydrocarbon radical which has not more than 15 C atoms and is unsubstituted or substituted, for example substituted by lower alkyl, lower alkoxy, aryl, halogen or nitro, such as corresponding unsubstituted or substituted lower alkyl, phenyl-lower alkyl, cycloalkyl or phenyl, for example 2-tri-lower alkylsilylethoxycarbonyl, such as 2-trimethylsilyl-ethoxycarbonyl or 2-(di-n-butyl-methyl-silyl)-ethoxycarbonyl, or 2-triarylsilylethoxycarbonyl, such as 2-triphenylsilylethoxycarbonyl.

In an arylmethylamino group which is a mono-, di- or, in particular, triarylmethylamino group, the aryl radicals are, in particular, substituted or unsubstituted phenyl radicals. Such groups are, for example, benzyl-, diphenylmethyl- and, in particular, tritylamino.

An etherified mercapto group in an amino group protected with such a radical is, in particular, arylthio or aryl-lower alkylthio, in which aryl is, in particular, phenyl which is unsubstituted or substituted, for example by lower alkyl, such as methyl or tert-butyl, lower alkoxy, such as methoxy, halogen, such as chlorine, and/or nitro. A corresponding amino-protective group is, for example, 4-nitrophenylthio.

In a 2-acyl-lower alk-1-en-1-yl radical which can be used as an amino-protective group, acyl is, for example, the corresponding radical of a lower alkanecarboxylic acid, of a benzoic acid which is unsubstituted or substituted, for example by lower alkyl, such as methyl or tert-butyl, lower alkoxy, such as methoxy, halogen, such as chlorine, and/or nitro, or, in particular, of a carbonic acid half-ester, such as a carbonic acid lower alkyl half-ester. Corresponding protective groups are, in particular, 1-lower alkanoyl-prop-1-en-2-yl, for example 1-acetyl-prop-1-en-2-yl, or 1-lower alkoxycarbonyl-prop-1-en-2-yl, for example 1-ethoxycarbonyl-prop-1-en-2-yl.

Preferred amino-protective groups are acyl radicals of carbonic acid half-esters, in particular tert-butyloxycarbonyl, benzyloxycarbonyl which is unsubstituted or substituted, for example as defined, for example 4-nitro-benzyloxycarbonyl, or diphenylmethoxycarbonyl, or 2-halo-lower alkoxycarbonyl, such as 2,2,2-trichlorethoxycarbonyl, and furthermore trityl or formyl.

Preferred protected carboxyl groups are, for example, tert-butoxycarbonyl, benzyloxycarbonyl or diphenylmethoxycarbonyl which are unsubstituted or substituted, or 2-trimethylsilyl-ethoxycarbonyl.

The reaction between the derivative of the formula II and the alcohol of the formula III can be carried out in suitable inert solvents. If possible, on the basis of the physical nature of the alcohol of the formula III, however, the reaction can also be carried out without a foreign solvent, and the alcohol of the formula III is employed in a large excess, for example a hundred times the equivalent amount, both as the reagent and as the solvent The reaction is carried out under shaking or stirring and under an argon or nitrogen atmosphere. Depending on the nature of the specific reactants the reaction is carried out at a temperature between 0° C. and 90° C., preferably between +20° C. and +60° C., for example at room temperature or 50° C. Optionally it is carried out in a high pressure tube. After a period of for example between 12 and 24 hours, further triphenylphosphine, diethyl azodicarboxylate and also alcohol of formula III can be added. The product of the first reaction stage is filtered of and washed with tetrahydrofuran, an alcohol, e.g. 2-propanol, and dichloromethane. Cleavage of the product from the polymer resin is accomplished by treatment of the reaction product with trifluoroacetic acid in dichloromethane for 15 to 30 minutes at a temperature between 20° C. and 50° C., e.g. room temperature or 30° C.

The cleavage reaction of the compound of the formula V can be carried out in suitable inert solvents, like acetic acid ethyl ester or tetrahydrofuran. The solvent can also be pure water or a mixture of water with another solvent, depending on the solubility of the compound of formula V in which case the solvent water would also be the reagent. The reaction is usually carried out at room temperature, but it can also be carried out at temperatures between 0° C. and 100° C. depending of the reactivity of the compound of formula V. Normally, the cleavage reaction is carried out with aqueous hydrogen chloride, but other Bronsted acids and Lewis acids can also be employed instead, like e.g. hydrogen bromide, diluted sulfuric acid, p-toluene sulfonic acid, boron trifluoride or metall cations.

The protective groups which are not a constituent of the desired end product of the formula I are detached in a manner known per se, for example by means of solvolysis, in particular hydrolysis, alcoholysis or acidolysis, or by means of reduction, in particular hydrogenolysis or chemical reduction, if necessary in stages or simultaneously. The detachment of the protective groups can be carried out before, after or simultaneously with the cleavage of the product from the polymer resin.

A protected amino group is set free in a manner known per se and, depending on the nature of the protective groups, in diverse manners, preferably by means of solvolysis or reduction. 2-Halo-lower alkoxycarbonylamino (if appropriate after conversion of a 2-bromo-lower alkoxycarbonylamino group into a 2-iodo-lower alkoxycarbonylamino group), aroyl-methoxycarbonylamino or 4-nitrobenzyloxycarbonylamino can be split, for example, by treatment with a suitable chemical reducing agent, such as zinc in the presence of a suitable carboxylic acid, such as aqueous acetic acid. Aroylmethoxycarbonylamino can also be split by treatment with a nucleophilic, preferably salt-forming reagent, such as sodium thiophenolate, and 4-nitro-benzyloxycarbonylamino can also be split by treatment with an alkali metal dithionite, for example sodium dithionite. Substituted or unsubstituted diphenylmethoxycarbonylamino, tert-lower alkoxycarbonylamino or 2-trisubstituted silylethoxycarbonylamino can be split by treatment with a suitable acid, for example formic or trifluoroacetic acid, substituted or unsubstituted benzyloxycarbonylamino can be split, for example, by means of hydrogenolysis, i.e. by treatment with hydrogen in the presence of a suitable hydrogenation catalyst, such as a palladium catalyst, and triarylmethylamino or formylamino can be split, for example, by treatment with an acid, such as a mineral acid, for example hydrochloric acid, or an organic acid, for example formic, acetic or trifluoroacetic acid, if appropriate in the presence of water, and an amino group protected by an organic silyl group can be set free, for example, by means of hydrolysis or alcoholysis. An amino group protected by 2-haloacetyl, for example 2-chloroacetyl, can be set free by treatment with thiourea in the presence of a base or with a thiolate salt, such as an alkali metal thiolate, of urea and subsequent solvolysis, such as alcoholysis or hydrolysis, of the condensation product formed. An amino group protected by 2-substituted silylethoxycarbonyl can also be converted into the free amino group by treatment with a hydrofluoric acid salt which supplies fluoride anions.

The starting material of the formula II is obtained as follows:

In the first stage, a compound of formula VI

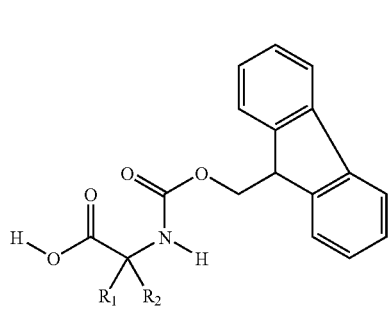

(VI)

in which $R_1$ and $R_2$ are as defined above for compounds of the formula I is reacted first with a coupling reagent like O-(1,2-dihydro-2-oxo-1-pyridyl)-N,N,N',N'-tetramethyluronium-tetrafluoroborat (TPTU), O-(3,4-dihydro-4-oxo-1,2,3-benzotriazin-3-yl)-N,N,N',N'-tetramethyluronium-tetrafluoroborat (TDBTU) or O-(1,2-dihydro-2-oxo-1-pyridyl)-N,N,N',N'-bis-(tetramethylen)-uronium-hexafluorophosphat in the presence of dimethylacetamide and a suitable amine, e.g. N-ethyldiisopropyl amine, in a suitable solvent, such like dichloromethane, and then at room temperature with aminooxy-2-chlortrityl polystyrene resin. The resin is isolated and shaken twice or three times for a period of 15 to 60 minutes, e.g. 30 minutes, with a freshly prepared dichloromethane/piperidine solution to provide a compound of formula VII

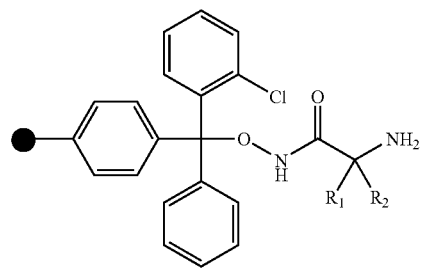

(VII)

in which the black circular plane indicates that the compound is bound to a polymer resin and in which $R_1$ and $R_2$ are as defined above for compounds of the formula I.

If $R_1$ and $R_2$ are both hydrogen preferably the first stage is carried out as follows: the aminooxy-2-chlortrityl polystyrene resin is mixed in a suitable solvent, such like dichloromethane, with a compound of formula VI, in which $R_1$ and $R_2$ are both hydrogen, in the presence of 1-hydroxybenzotriazole hydrate and 1,3-diisopropylcarbodiimide and the resulting mixture then treated with N-ethyl-diisopropylamine at room temperature. The obtained resin is isolated and shaken twice for a period of 15 to 45 minutes, e.g. 20 minutes, with a freshly prepared dichloromethane/piperidine solution to provide a compound of formula VII, in which the black circular plane indicates that the compound is bound to a polymer resin and in which $R_1$ and $R_2$ are both hydrogen.

In the second stage, the compound of formula VII is reacted with a compound of formula VIII

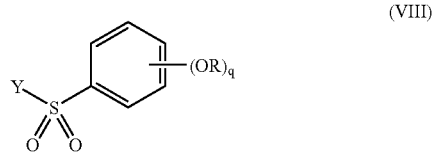

(VIII)

in which R and q are as defined above for compounds of the formula I and Y is a suitable leaving group, preferably halogen, such as chlorine, bromine or iodine, optionally in the presence of 4-dimethylaminopyridine and a suitable amine, e.g. N-ethyldiisopropylamine, in a suitable solvent, e.g. dichloromethane.

The starting material of the formula V is obtained as follows:

In the first stage, a compound of formula IX

(IX)

in which $R_3$ is as defined above for compounds of the formula I, $R_4$ is hydrogen or lower alkyl and D is $C_1$–$C_2$ alkylen, unsubstituted or substituted by lower alkyl, is reacted in a suitable solvent, e.g. methylen-chloride, at a temperature between −10° C. and +15° C., preferably between 0° C. and +5° C., with a compound of formula X

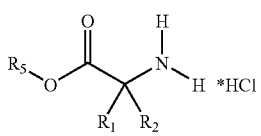

(X)

in which $R_1$ and $R_2$ are as defined above for compounds of the formula I and $R_5$ is methyl or ethyl in the presence of triethylamine or another suitable amine and MgSO$_4$ to afford a compound of formula XI

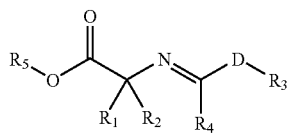

(XI)

in which $R_1$, $R_2$ and $R_3$ are as defined above for compounds of the formula I, $R_4$ is hydrogen or lower alkyl, $R_5$ is methyl or ethyl and D is $C_1$–$C_2$ alkylen.

In the second stage, the compound of formula XI is reacted with sodium borohydride in a suitable solvent, e.g. in a mixture of tetrahydrofuran and methanol at a temperature between −15° C. and 5° C., preferably −10° C. and 0° C., or another hydrogen donating agent to afford a compound of formula XII

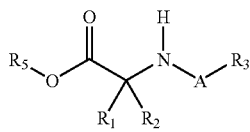

(XII)

in which A, $R_1$, $R_2$ and $R_3$ are as defined above for compounds of the formula I and $R_5$ is methyl or ethyl.

In the third stage the compound of formula XII is reacted with a compound of formula VIII'

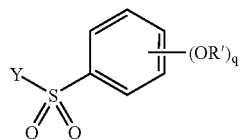

(VIII')

in which R' is hydrogen, q is as defined above for compounds of the formula I and Y is a suitable leaving group, preferably halogen, such as chlorine, bromine or iodine, in a suitabl solvent, e.g. dichloromethane, in the presence of a suitable amine, e.g. triethylamine, to give a compound of formula XIII

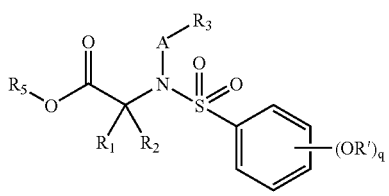

(XIII)

in which R' is hydrogen and q, A, $R_1$, $R_2$ and $R_3$ are as defined above for compounds of the formula I and $R_5$ is methyl or ethyl. A compound of formula VIII' in which R' is hydrogen can be prepared by reacting hydroxybenzenesulfonic acid sodium salt with thionyl chloride in dimethylformamide or another suitable solvent at a temperature of 60° C. to 70° C., preferably 65° C.

In the fourth stage the compound of formula XIII is reacted with a compound of formula XIV

Y—R   (XIV)

in which R is as defined above for compounds of formula I and Y is a suitable leaving group, preferably halogen, such as chlorine, bromine or iodine, in the presence of $K_2CO_3$ at room temperature in a suitable solvent, e.g. dimethylformamide, to afford a compound of formula XV,

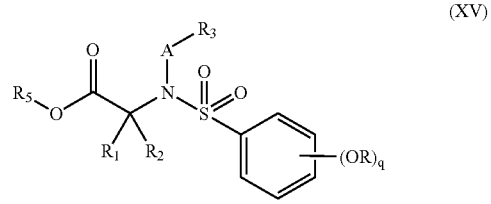

(XV)

in which R, q, A, $R_1$, $R_2$ and $R_3$ are as defined above for compounds of the formula I and $R_5$ is methyl or ethyl.

In the fifth stage the compound of formula XV is further reacted with an alkali metal hydroxide, e.g. LiOH, in a suitable solvent or mixture of solvents, e.g. a mixture of tetrahydrofuran, an alcohol and water, to give a compound of formula IV in which R, q, A, $R_1$, $R_2$ and $R_3$ ar as defined above for compounds of the formula I.

In the sixth stage the compound of formula IV is reacted with a compound of formula XVI

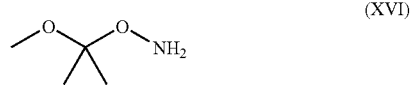

(XVI)

and a carbodiimide, like 1-ethyl-3-(3-dimethylaminopropyl)-carbodiimide, in the presence of 1-hydroxybenzotriazole, in a suitable solvent, like dimethylformamide, at a temperature between −5° C. and +10° C., preferably 0° C. and 5° C., to give a compound of formula V in which R, q, A, $R_1$, $R_2$ and $R_3$ are as defined above for compounds of the formula I.

A compound of formula VIII' can also be reacted with a compound of formula XIV before the reaction with a compound of formula XII as described above.

GENERAL PROCESS CONDITIONS

Free compounds of the formula I which are obtainable by the process and have salt-forming properties can be converted into their salts in a manner known per se, for example by treatment with acids or suitable derivatives thereof, for example by addition of the acid in question to the compound of the formula I dissolved in a suitable solvent, for example an ether, such as a cyclic ether, in particular dioxane, and especially tetrahydrofuran. Compounds of the formula I with acid groups, for example free carboxyl groups, are treated, for example, with a suitable base, for example a hydroxide, carbonate or bicarbonate, for salt formation.

Isomer mixtures obtainable according to the invention can be separated into the individual isomers in a manner known per se, for example racemates can be separated by formation of salts with optically pure salt-forming reagents and preparation of the diastereomer mixture thus obtained, for example by means of fractional crystallization.

The abovementioned reactions can be carried out under reaction conditions known per se, in the absenc or, usually, presence of solv nts or diluents, preferably those which are inert towards the reagents used and dissolve these, in the absence or presence of catalysts, condensation agents (for example phosphorus pentoxide) or neutralizing agents, for example bases, in particular nitrogen bases, such as triethylamine hydrochloride, depending on the nature of the reaction and/or of the reaction participants, at a reduced, normal or elevated temperature, for example in the temperature range from about −80° C. to about 200° C., preferably from about −20° C. to about 150° C., for example at the boiling point of the solvent used or at room temperature, under atmospheric pressure or in a closed vessel, if appropriate under pressure, and/or in an inert atmosphere, for example under a nitrogen atmosphere.

The reaction conditions stated specifically in each case are preferred.

Solvents and diluents are, for example, water, alcohols, for example lower alkylhydroxides, such as methanol, ethanol, propanol or, in particular, butanol, diols, such as ethylene glycol, triols, such as glycerol, or aryl alcohols, such as phenol, acid amides, for example carboxylic acid amides, such as dimethylformamide, dimethylacetamide or 1,3-dimethyl-3,4,5,6-tetrahydro-2(1H)-pyrimidinone (DMPU), carboxylic acids, in particular formic acid or acetic acid, amides of inorganic acids, such as hexamethylphosphoric acid triamide, ethers, for example cyclicethers, such as tetrahydrofuran or dioxane, or acyclic ethers, such as diethyl ether or ethylene glycol dimethyl ether, halogenated hydrocarbons, such as halo-lower alkanes, for example methylene chloride or chloroform, ketones, such as acetone, nitriles, such as acetonitrile, acid anhydrides, such as acetic anhydride, esters, such as ethyl acetate, bisalkanesulfines, such as dimethyl sulfoxide, nitrogen-containing heterocyclic compounds, such as pyridine, hydrocarbons, for example lower alkanes, such as heptane, or aromatics, such as benzene, toluene or xylene(s), or mixtures of these solvents, it being possible for the suitable solvents to be chosen in each case for the abovementioned reactions.

The customary processes are used for working up the compounds of the formula I which can be obtained or their salts, for example solvolysis of excess reagents; recrystallization; chromatography, for example partition, ion or gel chromatography, in particular preparative high pressure liquid chromatography; partition between an inorganic and organic solvent phase; one or several extractions, in particular after acidification or increasing the basicity or the salt content; drying over hygroscopic salts; digestion; filtration; washing; dissolving; evaporation (if necessary in vacuo or under a high vacuum); distillation; crystallization, for example of the resulting compounds in the form of an oil or from the mother liquor, it also being possible for the product to be seeded with a crystal of the end product; or a combination of two or more of the working up steps mentioned, which can also be employed repeatedly.

Starting materials and intermediates can be used in the pure form for example after working up, as mentioned last, in partly purified form or else, for example, directly as a crude product.

As a result of the close relationship between the compounds of the formula I in the free form and in the form of salts, the free compounds and their salts above and below are to be understood appropriately and expediently, where appropriate, as also meaning the corresponding salts or free compounds if the compounds contain salt-forming groups.

The compounds, including their salts, can also be obtained in the form of hydrates, or their crystals can include, for example, the solvent used for the crystallization.

Those starting substances which lead to the novel compounds of the formula I described above as particularly valuable are preferably employed in the process of the present invention.

The invention also relates to those embodiment forms of the process in which a compound obtainable as an intermediate at any process stage is used as the starting substance and the missing process steps are carried out, or in which a starting substance is formed under the reaction conditions or is used in the form of a derivative, for example a salt thereof.

The invention also relates to the compounds of the formula II

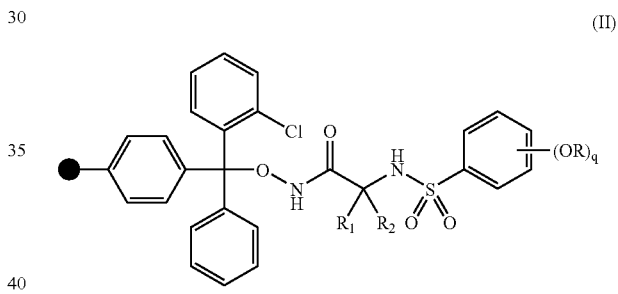

in which R, q, $R_1$ and $R_2$ are as defined above for compounds of the formula I and the black circular plane indicates that the compound is bound to a polymer resin, free functional groups therein being protected, if necessary, by easily detachable protective groups, which can be used as starting material for the preparation of the compounds of the formula I.

The invention also relates to the compounds of the formula IV

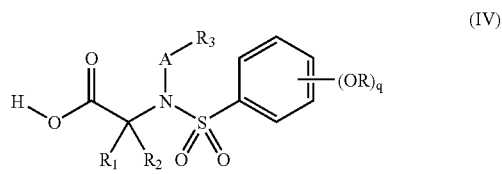

in which R, q, A, $R_1$, $R_2$ and $R_3$ are as defined above for compounds of the formula I, free functional groups present in the compound, if necessary, being protected by easily detachable protective groups, which can be used as starting material for the preparation of the compounds of the formula I.

The invention also relates to the compounds of the formula V

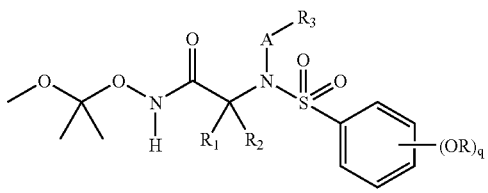

(V)

in which R, q, A, $R_1$, $R_2$ and $R_3$ are as defined above for compounds of the formula I, free functional groups present in the compound, if necessary, being protected by easily detachable protective groups, which can be used as starting material for the preparation of the compounds of the formula I.

The invention also relates to the compounds of the formula VIII

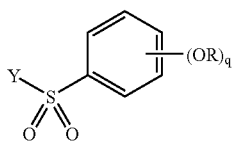

(VIII)

in which R is as defined above for compounds of the formula I or hydrogen, q is as defined above for compounds of the formula I and Y is halogen, free functional groups present in the compound, if necessary, being protected by easily detachable protective groups, which can be used as starting material for the preparation of the compounds of the formula I.

The present invention also relates to methods of using the compounds of the invention and their pharmaceutically acceptable salts, or pharmaceutical compositions thereof, in mammals for inhibiting the matrix-degrading metalloproteinases, e.g. stromelysin, gelatinase and macrophage metalloelastase, for inhibiting tissue matrix degradation, and for the treatment of matrix-degrading metalloproteinase dependent conditions as described herein, e.g. inflammation, rheumatoid arthritis, osteoarthritis, also tumors (tumor growth, metastasis, progression or invasion), pulmonary disorders (e.g. emphysema), and the like described herein. Tumors (carcinomas) include mammalian breast, lung, bladder, colon, prostate and ovarian cancer, and skin cancer, including melanoma and Kaposi's sarcoma.

Furthermore, the invention relates to a method for treatment of conditions or diseases, especially those described herein, associated with MMP2 comprising administering to warm-blooded animals, including humans, in need thereof a therapeutically effective amount of a selective MMP2 inhibitor or of a pharmaceutically acceptable salt or a pharmaceutically acceptable prodrug derivative of such a selective MMP2 inhibitor.

In particular, the invention relates to a method for treatment of hyperproliferative diseases, especially those described herein and more especially a tumor disease, associated with MMP2 comprising administering to warm-blooded animals, including humans, in need thereof an antihyperproliferatively effective amount of a selective MMP2 inhibitor or of a pharmaceutically acceptable salt or a pharmaceutically acceptable prodrug derivative of such a selective MMP2 inhibitor.

The term "selective MMP2 inhibitor" as used herein means a compound exhibiting an inhibiting concentration $IC_{50}$ for the enzyme MMP1 that is at least 100-fold higher than the inhibiting concentration $IC_{50}$ for the enzyme MMP2 as determined by the methods described herein. Preferably, the selective MMP2 inhibitor exhibit an inhibiting concentration $IC_{50}$ for the enzyme MMP1 that is at least 1000-fold higher than the $IC_{50}$ for the enzyme MMP2. More preferably, the selective MMP2 inhibitor exhibit an inhibiting concentration $IC_{50}$ for the enzyme MMP1 that is at least 2000-fold higher than the $IC_{50}$ for the enzyme MMP2. The term "non-peptide" as used herein means a compound without a substructure comprising a chemical bond between an aliphatic amine and a carboxylic acid.

Furthermore, the invention relates to a method for treatment of conditions or diseases, especially those described herein, associated with MMP's comprising administering to warm-blooded animals, including humans, in need thereof a therapeutically effective amount of a compound of formula I or of a pharmaceutically acceptable salt or a pharmaceutically acceptable prodrug derivative of such a compound.

The invention relates in particular to a method of treating warm-blooded animals, including humans, suffering from a hyperproliferative disease, especially a tumor disease, and in particular a hyperproliferative disease which responds to inhibition of MMP2 or MT1-MMP, which method comprises administering an antihyperproliferatively effective amount of a compound of the formula I or of a pharmaceutically acceptable salt or a pharmaceutically acceptable prodrug derivative thereof, or the use of a compound of the formula I for such treatment.

The invention relates also to the use of a compound of formula I or of a pharmaceutically acceptable salt thereof in the inhibition of MMP2 or MT1-MMP or both enzymes in warm-blooded animals, including humans, or in the preparation of pharmaceutical compositions for use in the therapeutic treatment of the human or animal body, in particular for the chemotherapy of tumours.

Depending on the species, age, individual condition, mode of administration and the particular clinical picture, effective doses, for example daily dos s of approximately 0.1 to about 5 g, preferably about 0.5 to about 2 g, of a compound of the pr s nt invention are administered to a warm-blooded animal of approximately 70 kg body weight.

The invention relates also to pharmaceutical compositions comprising an effective amount, especially an amount effective in the treatment of one of the above-mentio ned disorders, of the active ingredient together with pharmaceutically acceptable carriers that are suitable for topical, enteral, for example oral or rectal, or parenteral administration and that may be inorganic or organic, solid or liquid. There are used for oral administration especially tablets or gelatin capsules that comprise the active ingredient together with dilu ents, for example lactose, dextrose, sucrose, mannitol, sorbitol, cellulose and/or glycerol, and/or lubricants, for example silica, talc, stearic acid or salts thereof, such as magnesium or calcium stearate, and/or polyethylene glycol. Tablets may also comprise binders, for example magnesium aluminum silicate, starches, such as corn, wheat or rice starch, gela tin, methylcellulose, sodium carboxymethylcellulose and/or polyvinylpyrrolidone, and, if de sired, disintegrators, for example starches, agar, alginic acid or a salt thereof, such as so dium alginate, and/or effervescent mixtures, or adsorbents, dyes, flavorings and sweete ners. It is also possible to use the pharmacologically active compounds of the present invention in the form of parenterally administrable compositions or in the form of infusion so lutions. Such solutions are preferably isotonic aqueous solutions or suspen sions which, for example in the case of lyophilized compositions that comprise the active ingredient alone or together with a carrier, for example mannitol, can be made up prior to use. The pharmaceut ical compositions may be sterilized and/or may comprise excipients, for example preserva tives, stabilisers, wetting agents and/or emulsifiers, solubilisers, salts for regulating the os motic pressure and/or buffers. The present pharmaceutical compositions, which may, if de sired, comprise other pharmacologically active substances, such as antibiotics, are prepa red in a manner known per se, for example by means of conventional mixing, granulating, confectioning, dissolving or lyophilising processes, and comprise approximately from 1% to 95%, especially from approximately 1% to approximately 20%, active ingredient (s).

The following Examples serve to illustrate the invention without limiting the scope thereof. Temperatures are given in degrees Centigrade. If not mentioned otherwise, all evaporations are performed under reduced pressure, preferably between about 15 and 100 mmHg (=20–133 mbar). The structure of final products, intermediates and starting materials is confirmed by standard analytical methods, e.g. microanalysis and spectroscopic characteristics (e.g. MS, IR, NMR). Abbreviations used are those conv ntional in the art.

The short names and abbreviations used have the following meanings:

| Abbreviations: | |
|---|---|
| AcOEt | acetic acid ethyl ester |
| DMA | N,N-dimethylacetamide |
| DMF | dimethylformamide |
| DMSO | dimethylsulfoxide |
| ES | electrospray |
| h | hour(s) |
| HOBT | 1-hydroxybenzotriazole |
| HPLC | high pressure liquid chromatography |
| Me | methyl |
| min | minutes |
| MS | mass spectrometry |
| NMR | nuclear magnetic resonance |
| r.t. | room temperature |
| TFA | trifluoroacetic acid |
| THF | tetrahydrofurane |
| TPTU | O-(1,2-dihydro-2-oxo-1-pyridyl)-N,N,N',N'-tetramethyluronium tetrafluoroborate |
| WSCD | 1-ethyl-3-(3-dimethylaminopropyl)-carbodiimide |

| Abbreviations for the NMR spectra data | |
|---|---|
| b | broad |
| d | doublet |
| J | coupling constant |
| m | multiplet |
| q | quartet |
| s | singlet |
| t | triplet |
| ppm | parts per million |
| TMS | tetramethylsilan |

Reference Example 1:

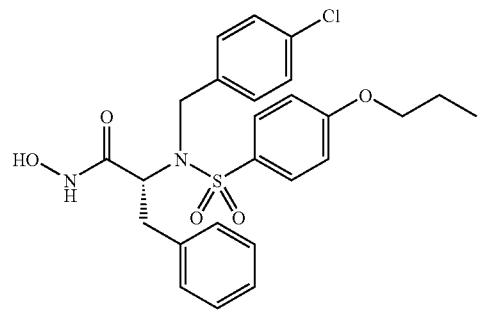

To the resin of stage 1.2 (90 mg, ~0.06 mmol) are added successively under an argon atmosphere triphenylphosphine (238 mg, 0.91 mmol) in dry THF (0.5 ml) and 4-chlorobenzyl alcohol (129 mg, 0.91 mmol). Finally, neat diethyl azodicarboxylate (0.141 ml, 0.91 mmol), is slowly added. After shaking for 15 h at 50° C. the suspension is filtered and the resin washed with THF (2×). The reaction is repeated twice with fresh reagents. The slurry is filtered and the resin rinsed with THF (2×), alternating with 2-propanol and THF (3×) and dichloromethane (3×). The product is cleaved from the support by treating the resin with a solution of TFA (95%)/dichloromethane 5:95 (v/v) for 20 min at 30° C. After filtration, a second analogous cleavage is carried out. The residue obtained after filtration and removal of the solvent is purified by preparative HPLC to yield (R)-2-[(4-Chlorobenzyl)-(4-propoxy-benzenesulfonyl)-amino]-N-hydroxy-3-phenyl-propionamide; MS (ES+): 503 (M+H)$^+$.

Stage 1.1: Polymer-bound (R)-2-Amino-N-hydroxy-3-phenyl-propionamide

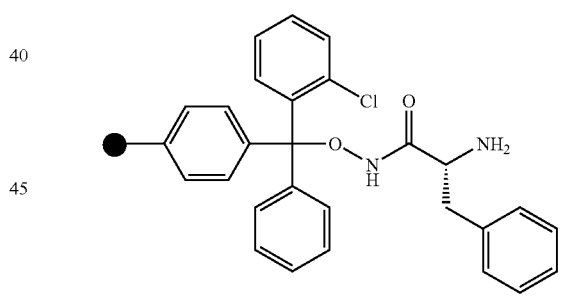

To a solution of N-(9-fluorenylmethoxycarbonyl)-D-phenylalanine (2.09 g, 5.4 mmol) in dry dichloromethane/DMA 1:1 (20 ml) are added TPTU (1.76 g, 5.94 mmol) and N-ethyldiiso-propylamine (1.02 ml, 5.94 mmol). After stirring for 5 min the mixture is added to aminooxy-2-chlorotrityl polystyrene resin (2.8 g, 2.7 mmol; Tetrahedron Lett. 1997, 38, 3311–3314) and the resulting suspension shaken at r.t. for 16 h. The mixture is filtered and the resin washed alternating with DMA and dichloromethane (3×). The described coupling procedure is repeated with a freshly prepared mixture of N-(9-fluorenylmethoxycarbonyl)-D-phenylalanine (2.09 g, 5.4 mmol), TPTU (1.76 g, 5.94 mmol) and N-ethyldiisopropylamine (1.02 ml, 5.94 mmol) in dichloromethane/DMA 1:1 (20 ml). After 16 h the suspension is filtered and the resin washed with DMA (2×), alternating with H$_2$O and DMA (2×), alternating with 2-propanol and THF (3×), THF (2×) and dichloromethane (3×).

The resin thus obtained is shaken for 30 min with a freshly prepared solution of dichloromethane/piperidine 8:2 (25 ml). After filtration, this process is repeated twice with fresh dichloromethane/piperidine solutions. The suspension is filtered, the resin washed with dichloromethane (2×), alternating with 2-propanol and dichloromethane (2×), dichloromethane (3×) and dried in vacuo, thus providing polymer-bound (R)-2-amino-N-hydroxy-3-phenyl-propionamide.

Stage 1.2: Polymer-bound (R)—N-Hydroxy-3-phenyl-2-(4-propoxy-benzenesulfonylamino)-propionamide

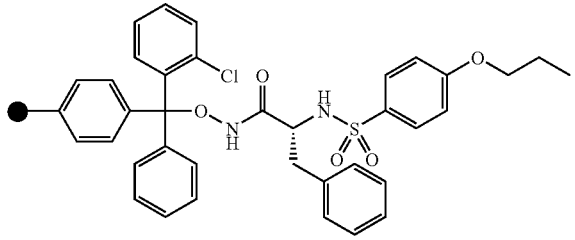

To 400 mg (~0.33 mmol) resin from stage 1.1 are added successively dry dichloromethane (2 ml), 4-dimethylaminopyridine (4 mg, 0.033 mmol), 4-propoxy-benzenesulfonyl chloride (309.8 mg, 1.32 mmol) dissolved in dry dichloromethane (1 ml), and N-ethyl-diisopropylamine (0.28 ml, 1.64 mmol). After shaking for 15 h at r.t. the suspension is filtered and the resin washed with dichloromethane (3×), alternating with DMA and H$_2$O (2×), 0.2M aequous citric acid, alternating with DMA and H$_2$O (2×), alternating with 2-propanol and THF (3×), and with dichloromethane (4×). The resin is dried under reduced pressur to provid polymer-bound (R)-N-hydroxy-3-phenyl-2-(4-propoxy-benzenesulfonylamino)-propionamide.

EXAMPLES 2 TO 57

Analogously to Example 1 the following hydroxamic acids of Examples 2 to 57 are obtained.

| Example | Compound | MS (ES+) (M + H)+ |
|---|---|---|
| 2 | (R)-2-{[4-(3-chloro-propoxy)-benzenesulfonyl]-(4-fluoro-benzyl)-amino}-N-hydroxy-3-methyl-butyramide | 473 |
| 3 | (R)-2-{[4-(3-chloro-propoxy)-benzenesulfonyl]-(3-methoxy-benzyl)-amino}-N-hydroxy-3-methyl-butyramide | 485 |
| 4 | (R)-2-{[4-(3-chloro-propoxy)-benzenesulfonyl]-(4-methoxy-benzyl)-amino}-N-hydroxy-3-methyl-butyramide | 485 |
| 5 | (R)-2-{(4-chloro-benzyl)-[4-(3-fluoro-propoxy)-benzenesulfonyl]-amino}-N-hydroxy-3-methyl-butyramide | 473 |
| 6 | (R)-2-{(4-fluoro-benzyl)-[4-(3-fluoro-propoxy)-benzenesulfonyl]-amino}-N-hydroxy-3-methyl-butyramide | 457 |
| 7 | (R)-2-{(4-(3-fluoro-propoxy)-benzenesulfonyl]-(3-methoxy-benzyl)-amino}-N-hydroxy-3-methyl-butyramide | 469 |
| 8 | (R)-2-{(4-chloro-benzyl)-[4-(4-fluoro-butoxy)-benzenesulfonyl]-amino}-N-hydroxy-3-methyl-butyramide | 487 |
| 9 | (R)-2-{(4-fluoro-benzyl)-[4-(4-fluoro-butoxy)-benzenesulfonyl]-amino}-N-hydroxy-3-methyl-butyramide | 471 |
| 10 | (R)-2-{[4-(4-fluoro-butoxy)-benzenesulfonyl]-(3-methoxy-benzyl)-amino]-N-hydroxy-3-methyl-butyramide | 483 |
| 11 | (R)-2-[(4-but-3-enyloxy-benzenesulfonyl)-(4-chloro-benzyl)-amino]-N-hydroxy-3-methyl-butyramide | 467 |
| 12 | (R)-2-[(4-but-3-enyloxy-benzenesulfonyl)-(4-fluoro-benzyl)-amino]-N-hydroxy-3-methyl-butyramide | 451 |
| 13 | (R)-2-[(4-but-3-enyloxy-benzenesulfonyl)-(3-methoxy-benzyl)-amino]-N-hydroxy-3-methyl-butyramide | 463 |
| 14 | (R)-2-[(4-but-3-enyloxy-benzenesulfonyl)-(4-methoxy-benzyl)-amino]-N-hydroxy-3-methyl-butyramide | 463 |
| 15 | (R)-2-{[4-(3-chloro-propoxy)-benzenesulfonyl]-(3-methoxy-benzyl)-amino}-N-hydroxy-propionamide | 457 |
| 16 | (R)-2-{[4-(3-chloro-propoxy)-benzenesulfonyl]-(4-methoxy-benzyl)-amino}-N-hydroxy-propionamide | 457 |
| 17 | (R)-2-{(4-chloro-benzyl)-[4-(3-fluoro-propoxy)-benzenesulfonyl]-amino}-N-hydroxy-propionamide | 445 |
| 18 | (R)-2-{(4-fluoro-benzyl)-[4-(3-fluoro-propoxy)-benzenesulfonyl]-amino}-N-hydroxy-propionamide | 429 |
| 19 | (R)-2-{[4-(3-fluoro-propoxy)-benzenesulfonyl]-(3-methoxy-benzyl)-amino}-N-hydroxy-propionamide | 441 |
| 20 | (R)-2-{(4-fluoro-benzyl)-[4-(4-fluoro-butoxy)-benzenesulfonyl]-amino}-N-hydroxy-propionamide | 443 |
| 21 | (R)-2-{[4-(4-fluoro-butoxy)-benzenesulfonyl]-(3-methoxy-benzyl)-amino}-N-hydroxy-propionamide | 455 |
| 22 | (R)-2-{[4-(4-fluoro-butoxy)-benzenesulfonyl]-(4-methoxy-benzyl)-amino}-N-hydroxy-propionamide | 455 |
| 23 | (R)-2-[(4-but-3-enyloxy-benzenesulfonyl)-(4-chloro-benzyl)-amino]-N-hydroxy-propionamide | 439 |
| 24 | (R)-2-[(4-but-3-enyloxy-benzenesulfonyl)-(3-methoxy-benzyl)-amino]-N-hydroxy-propionamide | 435 |
| 25 | (R)-2-[(4-but-3-enyloxy-benzenesulfonyl)-(4-methoxy-benzyl)-amino]-N-hydroxy-propionamide | 435 |
| 26 | (R)-2-{(4-chloro-benzyl)-[4-(3-chloro-propoxy)-benzenesulfonyl]-amino}-N-hydroxy-3-phenyl-propionamide | 537 |
| 27 | (R)-2-{[4-(3-chloro-propoxy)-benzenesulfonyl]-(4-fluoro-benzyl)-amino}-N-hydroxy-3-phenyl-propionamide | 521 |
| 28 | (R)-2-{[4-(3-chloro-propoxy)-benzenesulfonyl]-(3-methoxy-benzyl)-amino}-N-hydroxy-3-phenyl-propionamide | 533 |
| 29 | (R)-2-{[4-(3-chloro-propoxy)-benzenesulfonyl]-(4-methoxy-benzyl)-amino}-N-hydroxy-3-phenyl-propionamide | 533 |
| 30 | (R)-2-{(4-chloro-benzyl)-[4-(3-fluoro-propoxy)-benzenesulfonyl]-amino}-N-hydroxy-3-phenyl-propionamide | 521 |
| 31 | (R)-2-{(4-fluoro-benzyl)-[4-(3-fluoro-propoxy)-benzenesulfonyl]-amino}-N-hydroxy-3-phenyl-propionamide | 505 |
| 32 | (R)-2-{[4-(3-fluoro-propoxy)-benzenesulfonyl]-(3-methoxy-benzyl)-amino}-N-hydroxy-3-phenyl-propionamide | 517 |
| 33 | (R)-2-{[4-(3-fluoro-propoxy)-benzenesulfonyl]-(4-methoxy-benzyl)-amino}-N-hydroxy-3-phenyl-propionamide | 517 |
| 34 | (R)-2-{(4-chloro-benzyl)-[4-(4-fluoro-butoxy)-benzenesulfonyl]-amino}-N-hydroxy-3-phenyl-propionamide | 535 |
| 35 | (R)-2-{(4-fluoro-benzyl)-[4-(4-fluoro-butoxy)-benzenesulfonyl]-amino}-N-hydroxy-3-phenyl-propionamide | 519 |
| 36 | (R)-2-{[4-(4-fluoro-butoxy)-benzenesutfonyl]-(3-methoxy-benzyl)-amino}-N-hydroxy-3-phenyl-propionamide | 531 |
| 37 | (R)-2-{[4-(4-fluoro-butoxy)-benzenesulfonyl]-(4-methoxy-benzyl)-amino}-N-hydroxy-3-phenyl-propionamide | 531 |
| 38 | (R)-2-[(4-but-3-enyloxy-benzenesulfonyl)-(4-chloro-benzyl)-amino]-N-hydroxy-3-phenyl-propionamide | 515 |
| 39 | (R)-2-[(4-but-3-enyloxy-benzenesulfonyl)-(4-fluoro-benzyl)-amino]-N-hydroxy-3-phenyl-propionamide | 499 |
| 40 | (R)-2-[(4-but-3-enyloxy-benzenesulfonyl)-(3- | 511 |

-continued

| Example | Compound | MS (ES+) (M + H)+ |
|---|---|---|
| | methoxy-benzyl)-amino]-N-hydroxy-3-phenyl-propionamide | |
| 41 | (R)-2-[(4-but-3-enyloxy-benzenesulfonyl)-(4-methoxy-benzyl)-amino]-N-hydroxy-3-phenyl-propionamide | 511 |
| 42 | (R)-2-{(4-chloro-benzyl)-[4-(3-chloro-propoxy)-benzenesulfonyl]-amino}-N-hydroxy-4-methyl-valeramide | 503 |
| 43 | (R)-2-{[4-(3-chloro-propoxy)-benzenesulfonyl]-(4-fluoro-benzyl)-amino}-N-hydroxy-4-methyl-valeramide | 487 |
| 44 | (R)-2-{[4-(3-chloro-propoxy)-benzenesulfonyl]-(3-methoxy-benzyl)-amino}-N-hydroxy-4-methyl-valeramide | 499 |
| 45 | (R)-2-{[4-(3-chloro-propoxy)-benzenesulfonyl]-(4-methoxy-benzyl)-amino}-N-hydroxy-4-methyl-valeramide | 499 |
| 46 | (R)-2-{(4-chloro-benzyl)-[4-(3-fluoro-propoxy)-benzenesulfonyl]-amino}-N-hydroxy-4-methyl-valeramide | 487 |
| 47 | (R)-2-{(4-fluoro-benzyl)-[4-(3-fluoro-propoxy)-benzenesulfonyl]-amino}-N-hydroxy-4-methyl-valeramide | 471 |
| 48 | (R)-2-{[4-(3-fluoro-propoxy)-benzenesulfonyl]-(3-methoxy-benzyl)-amino}-N-hydroxy-4-methyl-valeramide | 483 |
| 49 | (R)-2-{[4-(3-fluoro-propoxy)-benzenesulfonyl]-(4-methoxy-benzyl)-amino}-N-hydroxy-4-methyl-valeramide | 483 |
| 50 | (R)-2-{(4-chloro-benzyl)-[4-(4-fluoro-butoxy)-benzenesulfonyl]-amino}-N-hydroxy-4-methyl-valeramide | 501 |
| 51 | (R)-2-{(4-fluoro-benzyl)-[4-(4-fluoro-butoxy)-benzenesulfonyl]-amino}-N-hydroxy-4-methyl-valeramide | 485 |
| 52 | (R)-2-{[4-(4-fluoro-butoxy)-benzenesulfonyl]-(3-methoxy-benzyl)-amino}-N-hydroxy-4-methyl-valeramide | 497 |
| 53 | (R)-2-{[4-(4-fluoro-butoxy)-benzenesulfonyl]-(4-methoxy-benzyl)-amino}-N-hydroxy-4-methyl-valeramide | 497 |
| 54 | (R)-2-[(4-but-3-enyloxy-benzenesulfonyl)-(4-chloro-benzyl)-amino]-N-hydroxy-4-methyl-valeramide | 481 |
| 55 | (R)-2-[(4-but-3-enyloxy-benzenesulfonyl)-(4-fluoro-benzyl)-amino]-N-hydroxy-4-methyl-valeramide | 465 |
| 56 | (R)-2-[(4-but-3-enyloxy-benzenesulfonyl)-(3-methoxy-benzyl)-amino]-N-hydroxy-4-methyl-valeramide | 477 |
| 57 | (R)-2-[(4-but-3-enyloxy-benzenesulfonyl)-(4-methoxy-benzyl)-amino]-N-hydroxy-4-methyl-valeramide | 477 |

EXAMPLE 58

The resin of stage 58.2 (70 mg, ~0.045 mmol) is treated under an argon atmosphere with dry dichloromethane (0.8 ml), triphenylphosphine (150 mg, 0.57 mmol) and 3-methoxy-benzyl alcohol (0.07 ml, 0.56 mmol). Finally, neat diethyl azodicarboxylate (0.088 ml, 0.56 mmol), is added at r.t. After stirring for 15 h at r.t. the slurry is filtered and the resin rinsed with dichloromethane (3x), alternating with 2-propanol and dichloromethane (3x) and dichloromethane (3x). The product is cleaved from the support by treating the resin with a solution of TFA (95%)/dichloromethane 5:95 (v/v). The residue obtained after filtration and removal of the solvent is purified by preparative HPLC to yield 2-([4-(4-fluoro-butoxy)-benzenesulfonyl]-(3-methoxy-benzyl)-amino)-N-hydroxy-acetamide; MS (ES+): 441 (M+H)+.

Stage 58.1: Polymer-bound 2-Amino-N-hydroxy-acetamide

To a suspension of aminooxy-2-chlorotrityl polystyrene resin (3.0 g, 3.15 mmol) in dry dichloromethane (30 ml) is added a mixture of N-(9-fluorenylmethoxycarbonyl)-glycine (3.40 g, 11.4 mmol), 1-hydroxybenzotriazole hydrate (1.27 g, ~8.33 mmol) and 1,3-diisopropylcarbodiimide (1.3 ml, 8.34 mmol) in dry dichloromethane (20 ml). The resulting mixture is treated with N-ethyldiisopropylamine (1.41 ml, 8.24 mmol) and stirred at r.t. for 15 h. After filtration, the resin is washed with DMF (2x), alternating with H$_2$O and DMF (3x), alternating with THF and 2-propanol (3x), THF (2x) and dichloromethane (3x). The coupling procedure is repeated with a fresh mixture of N-(9-fluorenylmethoxycarbonyl)-glycine (3.03 g, 10.2 mmol), 1-hydroxybenzotriazole (1.26 g, ~8.23 mmol), 1,3-diisopropylcarbodiimide (1.4 ml, 8.98 mmol) and N-ethyldiisopropylamine (1.41 ml, 8.24 mmol) in dry dichloromethane (30 ml). After stirring for 16 h the suspension is filtered and the polymer washed as described above. The resin thus obtained is treated with a freshly prepared solution of dichloromethane/piperidine 8:2 (100 ml), stirred at r.t. for 20 min. and separated via filtration. This process is repeated twice with fresh dichloromethane/piperidine solution. The resin is washed with dichloromethane (2x), alternating with 2-propanol and dichloromethane (2x), dichloromethane (2x), 2-propanol (2x) and dried in vacuo, thus providing polymer-bound 2-amino-N-hydroxy-acetamide.

Stage 58.2: Polymer-bound 2-[4-(4-Fluoro-butoxy)-benzenesulfonylamino]-N-hydroxy-acetamide To the resin from stage 58.1 (350 mg, ~0.3 mmol) are added successively 4-(4-fluorobutoxy)-benzenesulfonyl chloride (306 mg, 1.15 mmol) in dry dichloromethane (4 ml), and N-ethyldiisopropylamine (0.24 ml, 1.40 mmol) in dry dichloromethane (4 ml). After stirring for 15 h at r.t. the suspension is filtered and the resin washed with dichloromethane (2x), DMF (2x), alternating with H$_2$O and DMF (3x), alternating with THF and 2-propanol (3x), dichloromethane (3x). The resin is dried under reduced pressure to provide polymer-bound 2-[4-(4-fluoro-butoxy)-benzenesulfonylamino]-N-hydroxy-acetamide.

Analogously to Example 58 the following hydroxamic acids of Examples 59 to 67 are obtained.

| Example | Compound | MS (ES+) (M + H)+ |
|---|---|---|
| 59 | 2-{[4-(3-chloro-propoxy)-benzenesulfonyl]-(4-fluoro-benzyl)-amino}-N-hydroxy-acetamide | 431 |
| 60 | 2-{[4-(3-chloro-propoxy)-benzenesulfonyl]-(3-methoxy-benzyl)-amino}-N-hydroxy-acetamide | 443 |
| 61 | 2-{(4-chloro-benzyl)-[4-(3-chloro-propoxy)-benzenesulfonyl]-amino}-N-hydroxy-acetamide | 447 |
| 62 | 2-{(4-fluoro-benzyl)-[4-(3-fluoro-propoxy)-benzenesulfonyl]-amino}-N-hydroxy-acetamide | 415 |
| 63 | 2-{[4-(3-fluoro-propoxy)-benzenesulfonyl]-(3-methoxy-benzyl)-amino}-N-hydroxy-acetamide | 427 |
| 64 | 2-{(4-chloro-benzyl)-[4-(3-fluoro-propoxy)-benzenesulfonyl]-amino}-N-hydroxy-acetamide | 431 |
| 65 | 2-{(4-fluoro-benzyl)-[4-(4-fluoro-butoxy)-benzenesulfonyl]-amino}-N-hydroxy-acetamide | 429 |
| 66 | 2-{(4-chloro-benzyl)-[4-(4-fluoro-butoxy) | 445 |

-continued

| Example | Compound | MS (ES+) (M + H)+ |
|---|---|---|
|  | benzenesulfonyl]-amino}-N-hydroxy-acetamide |  |
| 67 | 2-[(4-but-3-enyloxy-benzenesulfonyl)-(4-chloro-benzyl)-amino]-N-hydroxy-acetamide | 425 |

EXAMPLE 68

To a solution of 48.81 g (0.114 mol) of {[4-(3-chloro-propoxy)-benzenesulfonyl]-(4-methoxybenzyl)-amino}-acetic acid in 500 ml of $CH_2Cl_2$, 19.56 ml (0.228 mol) of oxalyl chloride and 0.88 ml (0.011 mol) of DMF are added dropwise at 0–5° C. under $N_2$ atmosphere. The mixture is stirred for 1 h at 0–5° C. and 1 h at r.t. To a solution of 226 ml (3.42 mol) of) 50% hydroxylamine in $H_2O$ (Aldrich) in 1200 ml of THF, a solution of the freshly prepared above acid chloride in $CH_2Cl_2$ is added over 45 min. at −10 to −5° C. through a teflon tube using $N_2$ gas pressure. The reaction mixture is stirred for 30 min at −5 to 0° C. and filtered through paper filter to remove insoluble precipitates. The filtrate is diluted with $H_2O$ and extracted with $CH_2Cl_2$. The combined extracts are washed with brine, dried over $MgSO_4$ and concentrated under reduced pressure. The product is collected by filtration and washed with ether to give 43.03 g of 2-{[4-(3-chloro-propoxy)-benzenesulfonyl]-(4-methoxy-benzyl)-amino}-N-hydroxy-acetamide; NMR ($CDCl_3$): 2.2–2.35 (m, 2H), 3.69 (s, 2H), 3.76 (t, 2H, J=6 Hz), 3.79 (s, 3H), 4.21 (t, 2H, J=6 Hz), 4.26 (s, 2H), 6.77 (br s, 1H), 6.85 (d, 2H, J=9.04 Hz), 7.03 (d, 2H, J=9.04 Hz), 7.15 (d, 2H, J=9.04 Hz), 7.78 (d, 2H, J=8.56 Hz), 8.82 (br s, 1H).

Stage 68.1:

To a solution of 77.46 g (0.617 mol) of glycine methyl-ester hydrochloride in $CH_2Cl_2$, 92 ml (0.66 mol) of triethy-lamine, a solution of 60 g (0.44 mol) of p-anisaldehyde in 50 ml of $CH_2Cl_2$ and 40 g of $MgSO_4$ are successively added at 0–5° C. under $N_2$ atmosphere. After stirring for 18 h at r.t. the reaction mixture is filtered through celite and washed with $CH_2Cl_2$. The filtrate is concentrated under reduced pressure and then the crude mixture is diluted with AcOEt. The AcOEt solution is filtered again to remove triethylamine hydrochloride and the filtrate diluted with toluene and concentrated under reduced pressure (azeotropic removal of $H_2O$) to give 91.3 g of [(4-methoxy-benzylidene)-amino]-acetic acid methyl ester as light yellow crystals; NMR ($C_6D_6$): 3.18 (s, 3H), 3.34 (s, 3H), 4.13 (s, 3H), 6.69 (d, 2H, J=8.56 Hz), 7.70 (d, 2H, J=8.56 Hz), 7.79 (s, 1H).

Stage 68.2:

To a solution of 91.3 g (0.441 mol) of [(4-methoxy-benzylidene)-amino]-acetic acid methyl ester in 500 ml of THF and 1000 ml of MeOH, 20 g (0.529 mol) of sodium borohydride is added portionwise at −10 to 0° C. The reaction mixture is stirred for 30 min. at −10 to 0° C. and quenched with sat. $NH_4Cl$. After adding of ice-water, the mixture is concentrated to ¼ of whole volume and extracted with AcOEt. The combined extracts are washed with $H_2O$ and brine, dried over $MgSO_4$ and concentrated under reduced pressure to give (4-methoxybenzylamino)-acetic acid methyl ester; NMR ($CDCl_3$): 1.87 (br s, 1H), 3.41 (s, 2H), 3.73 (s, 3H), 3.74 (s, 2H), 3.8 (s, 3H), 6.86 (d, 2H, J=8.56 Hz), 7.24 (d, 2H, J=8.56 Hz).

Stage 68.3:

To a solution of 30.97 g (0.148 mol) of (4-methoxy-benzylamino)-acetic acid methyl ester in 200 ml of dioxane and 200 ml of $H_2O$, 25 ml (0.178 mol) of triethylamine a solution of 43.9 g (0.163 mol) of 4-(3-chloro-propoxy)-benzenesulfonyl chloride in 100 ml of dioxane is added at 0–5° C. The mixture is allowed to warm to r.t. and stirred for 3 h. The reaction mixture is neutralized with 1 N HCl and extracted with AcOEt. The combined extracts are dried over $MgSO_4$ and concentrated under reduced pressure to give {[4-(3-chloro-propoxy)-benzenesulfonyl]-(4-methoxy-ben-zyl)-amino}-acetic acid methyl ester; NMR ($CDCl_3$): 2.25–2.35 (m, 2H), 3.56 (s, 3H), 3.75 (t, 2H, J=6.04 Hz), 3.79 (s, 3H), 3.9 (s, 2H), 4.2 (t, 2H, J=6.04 Hz), 4.39 (s, 2H), 6.84 (d, 2H, J=8.56 Hz), 6.99 (d, 2H, J=9.08 Hz), 7.16 (d, 2H, J=9.08 Hz), 7.83 (d, 2H, J=8.56 Hz).

Stage 68.4:

To a solution of 59.7 g (0.135 mol) of {[4-(3-chloro-propoxy)-benzenesulfonyl]-(4-methoxybenzyl)-amino}-acetic acid methyl ester in 500 ml of MeOH, 500 ml of THF and 200 ml of $H_2O$, 11.3 g of $LiOH:H_2O$ (0.27 mol) is added at 0–5° C. The mixture is allowed to warm to r.t. and stirred for 4 h. The reaction mixture is concentrated under reduced pressure and diluted with $H_2O$ and AcOEt. After acidifying with 2N HCl at 0–5° C., the mixture is extracted with AcOEt. The combined extracts are washed with brine and concentrated under reduced pressure to give {[4-(3-chloro-propoxy)-benzenesulfonyl]-(4-methoxy-benzyl)-amino]-acetic acid; NMR ($CDCl_3$): 2.25–2.29 (m, 2H), 3.75 (t, 2H, J=6 Hz), 3.79 (s, 3H), 3.91 (s, 2H), 4.19 (t, 2H, J=6 Hz), 4.38 (s, 2H), 6.84 (d, 2H, J=8.56 Hz), 6.99 (d, 2H, J=8.56 Hz), 7.13 (d, 2H, J=9.04 Hz), 7.82 (d, 2H, J=9.04 Hz).

EXAMPLE 69

A solution of 0.22 g of 2-{[4-(4-fluorobutoxy)-benzene-sulfonyl](4-methoxy-benzyl)-amino}-N-(1-ethoxy-1-me-thyl-ethoxy) acetamide in 30 ml of AcOEt is treated with 7 ml of 5N aqueous HCl for 10 min. at r.t. and the mixture is extracted with AcOEt. The combined extracts are washed with sat. $NaHCO_3$ and brine, dried over $MgSO_4$ and con-centrated under reduced pressure to give solids which are washed with ether to afford 2-{[4-(4-fluorobutoxy)-benze-nesulfonyl]-(4-methoxy-benzyl)-amino]-N-hydroxy-aceta-mide; NMR ($CDCl_3$): 1.83–2.05 (m, 4H), 3.69 (s, 2H), 3.78 (s, 3H), 4.09 (t, 2H, J=5.56 Hz), 4.25 (s, 2H), 4.48 (t, 1H, J=5.52 Hz), 4.55–4.65 (m, 1H), 6.84 (d, 2H, J=8.56 Hz), 7.00 (d, 2H, J=9.04 Hz), 7.02 (br s, 1H), 7.15 (d, 2H, J=8.56 Hz), 7.77 (d, 2H, J=8.56 Hz), 8.85 (br s, 1H).

Stage 69.1:

A solution of 31.4 ml (430 mmol) of thionyl chloride and 0.2 ml (2.58 mmol) of DMF was quickly added to 10 g (43 mmol) of 4-hydroxybenzenesulfonic acid sodium salt under $N_2$ atmosphere. The resulting mixture is stirred at 65° C. for 6 h. At the end of this time, the mobile, nearly homogenous reaction mixture is poured on ice with vigorous stirring. An oily lower layer is produced and which is dissolved in 100 ml of $CH_2Cl_2$. The aqueous layer is extracted with $CH_2Cl_2$ and the combined organic solution is dried over $MgSO_4$ and concentrated under reduced pressure to give 8.19 g of 4-hydroxybenzenesulfonyl chloride; NMR ($CDCl_3$): 5.3 (br s, 1H), 7.01 (d, 2H, J=9.08 Hz), 7.94 (d, 2H, J=9.08 Hz).

Stage 69.2:

To a solution of 8.7 g (45.2 mmol) of 4-hydroxybenze-nesulfonyl chloride in 80 ml of $CH_2Cl_2$, a solution of 6.75 g (32.3 mmol) of (4-methoxy-benzylamino)-acetic acid methyl ester in 20 ml of $CH_2Cl_2$ and 12 ml (79.2 mmol) of triethylamine were added dropwise at 0° C. The resulting mixture is stirred for 4 h at r.t., neutralized with cold 1 N aqueous HCl and extracted with $CH_2Cl_2$. The combined extracts are washed with $H_2O$ and brine, dried over $MgSO_4$ and concentrated under reduced pressure. The residue is purified by column chromatography on silica gel (eluent; $AcOEt:CH_2Cl_2=50:1~5:1$) to give [(4-hydroxy-benzenesulfonyl)-(4-methoxy-benzyl)-amino]-acetic acid methyl ester; NMR ($CDCl_3$): 3.57 (s, 3H), 3.79 (s, 3H), 3.90 (s, 2H), 4.40 (s, 2H), 5.59 (s, 1H), 6.84 (d, 2H, J=8.6 Hz), 6.93 (d, 2H, J=10.64 Hz), 7.15 (d, 2H, J=8.6 Hz), 7.82 (d, 2H, J=10.64 Hz).

Stage 69.3:

To a suspension of 1 g (2.74 mmol) of [(4-hydroxy-benzenesulfonyl)-(4-methoxy-benzyl)-amino]-acetic acid methyl ester and 1.14 g (8.22 mmol) of $K_2CO_3$ in 8 ml of DMF, 0.59 ml (5.47 mmol) of 1-bromo-4-fluorobutane is added dropwise at r.t. After stirring for 18 h at r.t., the reaction mixture is diluted with $H_2O$ and extracted with AcOEt. The combined extracts are washed with brine, dried over $MgSO_4$ and concentrated under reduced pressure. The residue is purified by column chromatography on silica gel (AcOEt:n-hexane=3:1) to give {[4-(4-fluorobutoxy)-benzenesulfonyl](4-methoxy-benzyl)-amino}-acetic acid methyl ester; NMR ($CDCl_3$): 1.86–1.96 (m, 4H), 3.57 (s, 3H), 3.79 (s, 3H), 3.90 (s, 2H), 4.08 (t, 2H, J=6.04 Hz), 4.39 (s, 2H), 4.46 (t, 1H, J=6.04 Hz), 4.55–4.65 (m, 1H), 6.83 (d, 2H, J=8.56 Hz), 6.97 (d, 2H, J=9.08 Hz), 7.15 (d, 2H, J=8.56 Hz), 7.82 (d, 2H, J=9.08 Hz).

Stage 69.4:

To a solution of 1.04 g (2.37 mmol) of {[4-(4-fluorobutoxy)-benzenesulfonyl]-(4-methoxybenzyl)-amino}-acetic acid methyl ester in 15 ml of THF, 15 ml of MeOH and 7 ml of $H_2O$, 0.24 g (5.7 mmol) of LiOH mono-hydrate is added in portions and the mixture is stirred for 30 min at 0–5° C. After stirring for additional 3.5 h, the reaction mixture is acidified with 1 N aqueous HCl and extracted with AcOEt. The combined extracts are washed with brine, dried over $MgSO_4$ and concentrated under reduced pressure to give ([4-(4-fluoro-butoxy)-benzenesulfonyl]-(4-methoxy-benzyl)-amino)-acetic acid; NMR ($CDCl_3$): 1.86–1.96 (m, 4H), 3.79 (s, 3H), 3.90 (s, 2H), 4.08 (t, 2H, J=5.52 Hz), 4.38 (s, 2H), 4.48 (t, 1H, J=6.04 Hz), 4.55–4.65 (m, 1H), 6.84 (d, 2H, J=8.56 Hz), 6.98 (d, 2H, J=9.08 Hz), 7.14 (d, 2H, J=8.56 Hz), 7.81 (d, 2H, J=9.08 Hz).

Stage 69.5:

To a solution of 20 g (123 mmol) of N-hydroxyphthalimide in 360 ml of $CH_3CN$, 26.42 ml (276 mmol) of 2-methoxypropene and 42.36 mg (0.246 mmol) of anhydrous p-toluenesulfonic acid are added in portions at r.t. After stirring for 1 h, the mixture is diluted with 25 ml of sat. $NaHCO_3$ and concentrated under reduced pressure. The residue is extracted with EtOAc and the organic layer is washed with $H_2O$ and brine, dried over $MgSO_4$ and concentrated under reduced pressure to give 21.84 g of 2-(1-methoxy-1-methyl-ethoxy)isoindole-1,3-dione as a white solid; NMR ($CDCl_3$): 1.57 (s, 6H), 3.61 (s, 3H), 7.75 (dd, 2H, J=5.56 Hz, J=3.0 Hz), 7.83 (dd, 2H, J=5.56 Hz, J=3.0 Hz).

Stage 69.6:

To a solution of 21.8 g (92.8 mmol) of 2-(1-methoxy-1-methyl-ethoxy)-isoindole-1,3-dione in 200 ml of $CH_2Cl_2$ and 70 ml of MeOH, 191.2 ml (191.2 mmol) of 1 M Hydrazine in THF is added dropwise over 40 min at 0–5° C. After stirring for 2 h at r.t., the mixture is filtered to remove insoluble precipitates. The filtrate is concentrated under reduced pressure, extracted with ether. The combined extracts are washed with 10% NaOH, dried over $MgSO_4$ and concentrated under reduced pressure to give 0-(1-methoxy-1-methyl-ethyl)-hydroxylamine; NMR ($CDCl_3$): 1.36 (s, 6H), 3.25 (s, 3H), 4.95 (br s, 2H).

Stage 69.7:

To a solution of 0.425 g (1 mmol) of desired {[4-(4-fluorobutoxy)-benzenesulfonyl](4-methoxy-benzyl)-amino}-acetic acid and 0.27 g (2 mmol) of HOBT in 4 ml of DMF, a solution of 0.116 g of O-(1-methoxy-1-methyl-ethyl)-hydroxylamine in 1 ml of DMF and 0.23 g of WSCD were successively added at 0–5° C. and the mixture was stirred for 1 h. After stirring for additional 2 h at r.t., the mixture is diluted with $H_2O$ and extracted with AcOEt. The combined extracts are dried over $MgSO_4$ and concentrated under reduced pressure. The residue is purified by column chromatography on silica gel (eluent; AcOEt:n-hexane=1:1) to give 2-{[4-(4-fluorobutoxy)-benzenesulfonyl-4-methoxy-benzyl)-amino}-N-(1-ethoxy-1-methyl ethoxy) acetamide; NMR ($CDCl_3$): 1.35 (s, 6H), 1.83–2.0 (m, 4H), 3.29 (s, 3H), 3.70 (s, 2H), 3.78 (s, 3H), 4.08–4.11 (m, 2H), 4.32 (s, 2H), 4.47–4.49 (m, 1H), 4.60 (br s, 1H), 6.80–6.90 (m, 2H), 6.95–7.05 (m, 2H), 7.10–7.25 (m, 2H), 7.79 (d, 2H, J=9.06 Hz), 8.46 (br s, 1H).

Analogously to Example 69 the following hydroxamic acids of Examples 70 to 76 are obtained.

EXAMPLE 70

2-{[4-(4-chlorobutoxy)-benzenesulfonyl}(4-methoxy-benzyl)-amino]-N-hydroxy-acetamide; NMR ($CDCl_3$): 1.95–2.05 (m, 4H), 3.55–3.65 (m, 2H), 3.68 (s, 2H), 3.77 (s, 3H), 4.07 (br s, 2H), 4.25 (s, 2H), 6.84 (d, 2H, J=8.56 Hz), 6.99 (d, 2H, J=9.04 Hz), 7.00 (br s, 1H), 7.15 (d, 2H, J=8.56 Hz), 7.77 (d, 2H, J=9.04 Hz), 8.84 (br s, 1H).

EXAMPLE 71

{(4-methoxy-benzyl)-[4-(4,4,4-trifluorobutoxy)-benzenesulfonyl]-amino}-N-hydroxy-acetamide; NMR ($CDCl_3$): 2.01–2.15 (m, 2H), 2.25–2.40 (m, 2H), 3.70 (s, 2H), 3.79 (s, 3H), 4.10 (t, 2H, J=6.04 Hz), 4.26 (s, 2H), 6.73 (br s, 1H), 6.85 (d, 2H, J=8.56 Hz), 7.01 (d, 2H, J=9.08 Hz), 7.15 (d, 2H, J=8.56 Hz), 7.78 (d, 2H, J=9.08 Hz), 8.83 (br s, 1H).

EXAMPLE 72

{[4-(4-fluoropropoxy)-benzenesulfonyl]-(4-methoxy-benzyl)-amino}-N-hydroxy-acetamide; NMR ($CDCl_3$): 2.15–2.30 (m, 2H), 3.70 (s, 2H), 3.79 (s, 3H), 4.18–4.20 (t, 2H, J=6.04 Hz), 4.26 (s, 2H), 4.61 (t, 1H, J=5.56 Hz), 4.73 (t, 1H, J=5.52 Hz), 6.53 (br s, 1H), 6.85 (d, 2H, J=8.56 Hz), 7.03 (d, 2H, J=8.56 Hz), 7.15 (d, 2H, J=8.56 Hz), 7.78 (d, 2H, J=8.56 Hz), 8.82 (br s, 1H).

EXAMPLE 73

[(4-but-3-en-1-yloxy-benzenesulfonyl](4-methoxy-benzyl)-amino]-N-hydroxy-acetamide; NMR ($CDCl_3$): 2.50–2.65 (m, 2H), 3.70 (s, 2H), 3.79 (s, 3H), 4.09 (t, 2H, J=7.04 Hz), 4.26 (s, 2H), 5.13–5.22 (m, 2H), 5.75–5.95 (m, 1H), 6.56 (br s, 1H), 6.84 (d, 2H, J=8.56 Hz), 7.01 (d, 2H, J=9.04 Hz), 7.15 (d, 2H, J=8.56 Hz), 7.76 (d, 2H, J=9.04 Hz), 8.83 (brs, 1H).

EXAMPLE 74

2-{[4-(3-chloropropoxy)-benzenesulfonyl]-pyridine-3-ylmethyl-amino}-N-hydroxy-acetamide; NMR (DMSO-d6): 2.20–2.22 (m, 2H), 3.78 (s, 2H), 3.71–3.90 (m, 4H), 4.22 (s, 2H), 4.51 (s, 2H), 7.17 (d, 2H, J=8.08 Hz), 7.84 (d, 2H, J=8.56 Hz), 7.95 (br s, 1H), 8.47 (d, 2H, J=7.08 Hz), 8.80 (br s, 1H), 8.87 (s, 1H), 10.97 (br s, 1H).

EXAMPLE 75

[(4-methoxy-benzyl)-[4-prop-2-ynyloxy-benzenesulfonyl]-amino]-N-hydroxy-acetamide; NMR (CDCl$_3$): 3.61 (s, 2H), 3.75 (s, 3H), 4.31 (s, 2H), 4.90 (d, 2H, J=2.0 Hz), 6.90 (d, 2H, J=8.56 Hz), 7.10–7.20 (m, 4H), 7.85 (d, 2H, J=8.56 Hz), 8.89 (br s, 1H), 10.51 (br s, 1H).

EXAMPLE 76

[(4-methoxy-benzyl)-[4-but-2-ynyloxy-benzenesufonyl]-amino]-N-hydroxy-acetamide; NMR (CDCl$_3$): 1.85 (s, 3H), 3.59 (s, 2H), 3.74 (s, 3H), 4.29 (s, 2H), 6.88 (d, 2H, J=8.56 Hz), 7.11–7.20 (m, 4H), 7.82 (d, 2H, J=9.04 Hz), 8.87 (br s, 1H), 10.48 (br s, 1H).

EXAMPLE 77

To a solution of 0.697 g (0.719 mmol) of [4-(3-chloropropoxy)-benzenesulfonyl]-(2,2-dimethyl-propyl)-amino acetic acid ethyl ester and 0.248 g (3.57 mmol) of hydroxylamine hydrochloride salt in 6 ml of MeOH, freshly prepared NaOMe from 0.25 g (6.247 mmol) of NaH in MeOH is added at 0° C. After stirring for 18 h at r.t., the mixture is poured into ice-water and extracted with AcOEt. The combined extracts are washed with brine, dried over MgSO$_4$ and concentrated under reduced pressure. The residue is purified by column chromatography on silica gel (AcOEt:n-hexane=3:1) to 2-([4-(3-chloropropoxy)-benzenesulfonyl)-(2,2-dimethyl-propyl)-amino-N-hydroxy-acetamide; NMR (CDCl$_3$): 0.98 (s, 9H), 2.20–2.35 (m, 2H), 2.95 (s, 2H), 3.69 (s, 2H), 3.75 (t, 2H, J=6.12 Hz), 4.20 (t, 2H, J=5.76 Hz), 7.03 (d, 2H, J=8.92 Hz), 7.06 (br s, 1H), 7.76 (d, 2H, J=8.92 Hz), 9.54 (br s, 1H).

Stage 77.1:

To a solution of 3.5 g (13 mmol) of 4-(3-chloropropoxy)-benzenesulfonyl chloride in 100 ml of CH$_2$Cl$_2$, a solution of 1.62 g (18.56 mmol) of neopentyl amine in 15 ml of CH$_2$Cl$_2$ and 2.59 ml (18.56 mmol) of triethyl amine are added dropwise at 0–5° C. After stirring for 2.5 h at r.t., the reaction mixture is neutralized with 1 N aqueous HCl and extracted with AcOEt. The combined extracts are washed with brine, dried over MgSO$_4$ and concentrated under reduced pressure to give 4-(3-chloropropoxy)-N-(2,2-dimethyl-propyl)-benzenesulfonamide; NMR (CDCl$_3$): 0.879 (s, 9H), 2.20–2.35 (m, 2H), 2.66 (d, 2H, J=6.88 Hz), 3.76 (t, 2H, J=6.28 Hz), 4.20 (t, 2H, J=5.84 Hz), 4.35–4.465 (m, 1H), 6.98 (d, 2H, J=8.88 Hz), 7.77 (d, 2H, J=8.88 Hz).

Stage 77.2:

To a suspension of 0.197 g (4.93 mmol) of NaH in 10 ml of THF, a solution of 1 g (3.13 mmol) of 4-(3-chloropropoxy)-N-(2,2-dimethyl-propyl)-benzenesulfonamide in 10 ml of THF is added in portions at 0° C. and the resulting mixture is stirred for 30 min at r.t. To the solution, 0.55 ml (4.93 mmol) of bromo-ethylacetate is added and the reaction mixture is stirred for 40 min. at r.t., neutralized with 1 N aqueous Hcl and extracted with AcOEt. The combined extracts are washed with brine, dried over MgSO$_4$ and concentrated under reduced pressure. The residue is purified by column chromatography on silica gel (AcOEt:n-hexane=1:6) to give [4-(3-chloropropoxy)-benzenesulfonyl]-(2,2-dimethyl-propyl)-amino acetic acid ethyl ester; NMR (CDCl$_3$): 0.96 (s, 9H), 1.20 (t, 3H, J=7.0 Hz), 2.20–2.30 (m, 2H), 3.08 (s, 2H), 3.75 (t, 2H, J=6.24 Hz), 4.02 (s, 2H), 4.08 (q, 2H, J=7.0 Hz), 4.17 (t, 2H, J=5.82 Hz), 6.96 (d, 2H, J=8.92 Hz), 7.76 (d, 2H, J=8.92 Hz).

EXAMPLE 78

Further Intermediates

The compounds described herein are used as intermediates in various stages of the preparation of compounds of formula I.

78.1: Compounds of formula VII

The polymer-bound compounds (R)-2-amino-N-hydroxy-3-methyl-butyramide, (R)-2-amino-N-hydroxy-propionamide and (R)-2-amino-N-hydroxy-4-methyl-valeramide are synthesized from N-(9-fluorenylmethoxycarbonyl)-D-valine, N-(9-fluorenylmethoxycarbonyl)-D-alanine and N-(9-fluorenylmethoxycarbonyl)-D-leucine and aminooxy-2-chlorotrityl polystyrene resin in analogy with the preparation described in Example 1, stage 1.1.

78.2: Compounds of formula II

The polymer-bound compounds (R)-2-[4-(3-chloro-propoxy)-benzenesulfonylamino]-N-hydroxy-3-phenyl-propionamide, (R)-2-[4-(3-fluoro-propoxy)-benzenesulfonylamino]-N-hydroxy-3-phenyl-propionamide, (R)-2-[4-(4-fluoro-butoxy)-benzenesulfonylamino]-N-hydroxy-3-phenyl-propionamide, (R)-2-(4-but-3-en-1-yloxy-benzenesulfonylamino)-N-hydroxy-3-phenyl-propionamide, (R)-2-[4-(3-chloro-propoxy)-benzenesulfonylamino]-N-hydroxy-3-methyl-butyramide, (R)-2-[4-(3-fluoro-propoxy)-benzenesulfonylamino]-N-hydroxy-3-methyl-butyramide, (R)-2-[4-(4-fluoro-butoxy)-benzenesulfonylamino]-N-hydroxy-3-methyl-butyramide, (R)-2-(4-but-3-en-1-yloxy-benzenesulfonylamino)-N-hydroxy-3-methyl-butyramide, (R)-2-[4-(3-chloro-propoxy)-benzenesulfonylamino]-N-hydroxy-propionamide, (R)-2-[4-(3-fluoro-propoxy)-benzenesulfonylamino]-N-hydroxy-propionamide, (R)-2-[4-(4-fluoro-butoxy)-benzenesulfonylamino]-N-hydroxy-propionamide, (R)-2-(4-but-3-en-1-yloxy-benzenesulfonylamino)-N-hydroxy-propionamide, (R)-2-[4-(3-chloro-propoxy)-benzenesulfonylamino]-N-hydroxy-4-methyl-valeramide, (R)-2-[4-(3-fluoro-propoxy)-benzenesulfonylamino]-N-hydroxy-4-methyl-valeramide, (R)-2-[4-(4-fluoro-butoxy)-benzenesulfonylamino]-N-hydroxy-4-methyl-valeramide and (R)-2-(4-but-3-en-1-yloxy-benzenesulfonylamino)-N-hydroxy-4-methyl-valeramide, are prepared in analogy with the preparation described in Example 1, stage 1.2.

The polymer-bound compounds 2-[4-(3-chloro-propoxy)-benzenesulfonylamino]-N-hydroxy-acetamide, 2-[4-(3-fluoro-propoxy)-benzenesulfonylamino]-N-hydroxy-acetamide and 2-[4-(but-3-en-1-yloxy)-benzenesulfonylamino]-N-hydroxy-acetamide are prepared in analogy with the preparation described in Example 58, stage 58.2.

78.3: Compounds of formula VIII 78.3.1: 4-(3-Chloropropoxy) benzenesulfonyl chloride To a solution of 52.75 g (0.265 mol) of (3-chloropropoxy)-benzene in 100 ml of CH$_2$Cl$_2$, a solution of 19.4 ml (0.292 mol) of chlorosulfonic acid in 100 ml of CH$_2$Cl$_2$ is added dropwise at 0–5° C. under N$_2$ atmosphere. The mixture is allowed to warm to ambient temperature and stirred for 2 hours. To the mixture, 29.6 ml (0.345 mol) of oxalyl chloride and 4 ml (0.052 mol) of DMF are added dropwise at r.t. and the mixture is stirred for 18 h at r.t. The reaction mixture is poured into ice-water, extracted with CH$_2$Cl$_2$. The combined extracts are dried over MgSO$_4$ and concentrated under reduced pressure to give 58.5 g of 4-(3-chloropropoxy) benzenesulfonyl chloride; NMR (CDCl$_3$): 2.26–2.36 (m, 2H), 3.76 (t, 2H, J=6.04 Hz), 4.24 (t, 2H, J=6.04 Hz), 7.06 (d, 2H, J=9.08 Hz), 7.98 (d, 2H, J=9.08 Hz).

Stage 78.3.1.1 (3-Chloro-propoxy)-benzene

To a suspension of 44 g (0.318 mol) of K$_2$CO$_3$ in 300 ml of acetone, 15 g (0.159 mol) of phenol and 18.9 ml (0.191 mol) of 1-bromo-3-chloropropane are added successively at r.t. under N$_2$ atmosphere. The mixture is refluxed for 6 h and concentrated under reduced pressure. The crude mixture is diluted with cold 1 N aqueous NaOH and extracted with AcOEt. The combined extracts are washed with H$_2$O, dried over MgSO$_4$ and concentrated under reduced pressure to give 26.25 g of (3-chloro-propoxy)benzene (yield 83%); NMR (CDCl$_3$): 2.20–2.27 (m, 2H), 3.75 (t, 2H, J=6.04 Hz), 4.11 (t, 2H, J=6.04 Hz), 6.9–6.97 (m, 3H), 7.25–7.31 (m, 2H).

78.3.2: 4-(3-Fluoro-propoxy)-benzenesulfonyl chloride

A stirred mixtur of the sodium salt of 4-hydroxybenzenesulfonic acid dihydrate (3.49 g, 15 mmol) in ethanol (15 ml) is treated successively at r.t with 2N NaOH (7.5 ml, 15 mmol) and 1-bromo-3-fluoro-propane (1.37 ml, 15 mmol) and refluxed for 15 h. The crystalline residue obtained after removal of the solvent is triturated with ethanol/H 20 (2:1) and chilled to 0° C. The product is filtered off, washed with cold ethanol/H 20 (2:1) and dried in vacuo to yield the sodium salt of 4-(3-fluoro-propoxy)-benzenesulfonic acid. A mixture of this salt (2.89 g, 11.3 mmol) and dichloromethane (5 ml) is treated at r.t. with SOCl$_2$ (5 ml, 68.9 mmol) and DMF (0.2 ml). After stirring for 72 h at r.t., the residue is treated with ice-water and the aequous phase extracted twice with diethyl ether. The combined organic layers are dried with Na$_2$SO$_4$, evaporated and the residue dried in vacuo to yield the title compound; NMR (CDCl$_3$) d: 7.98 and 7.04 (AA'BB', 4H), 4.77 (t, 1H), 4.53 (t, 1H), 4.20 (t, 2H), 2.08–2.25 (m, 2H).

78.3.3: 4-(3-Fluoro-butoxy)-benzenesulfonyl chloride

The title compound is prepared by analogy with the synthesis of 4-(3-fluoro-propoxy)-benzenesulfonyl chloride described under Example 78.3.2; NMR (CDCl$_3$) d: 7.96 and 7.02 (AA'BB', 4H), 4.64 (t, 1H), 4.40 (t, 1H), 4.11 (t, 2H), 1,73–2.06 (m, 4H).

78.3.4: 4-(But-3-enyloxy)-benzenesulfonyl chloride

A stirred mixture of the sodium salt of 4-hydroxybenzenesulfonic acid dihydrate (4.65 g, 20 mmol) in ethanol (20 ml) is treated successively at r.t. with 2N NaOH (10 ml, 20 mmol) and 4-bromo-1-butene (2.03 ml, 20 mmol) and refluxed for 15 h. The solvent is partially distilled off and the residue chilled to 0° C. The crystalline product is filtered off and washed with cold H$_2$O. The filtrate is concentrated under vacuum until a precipitate appears. After addition of H$_2$O the suspension is chilled to 0° C. and filtered. The residue is rinsed with cold H$_2$O, combined with the first crop of crystals and dried in vacuo to yield the sodium salt of 4-(but-3-enyloxy)-benzenesulfonic acid. A mixture of this salt (2.67 g, 10.7 mmol) and dichloromethane (5 ml) is treated at r.t. with SOCl$_2$ (5 ml, 68.9 mmol) and DMF (0.2 ml). After stirring for 15 h at r.t., the residue is treated with ice-water and the aequous phase extracted twice with diethyl ether. The combined organic layers are dried with Na$_2$SO$_4$, evaporated and the residue dried in vacuo to yield the title compound; NMR (CDCl$_3$) d: 7.96 and 7.02 (AA'BB', 4H), 5.77–5.99 (m, 1H), 5.09–5.26 (m, 2H), 4.11 (t, 2H), 2.51–2.66 (m, 2H).

EXAMPLE 79

To a solution of 4.2 g (7.93 mmol) of 2-[(4-but-3-enyloxy-benzenesulfonyl)-(4-[1,2,4]triazol-1-yl-benzyl)-amino]-N-(1-methoxy-1-methyl-ethoxy)-acetamide (stage 79.6) in 100 ml of AcOEt, 28 ml of 5 N aqueous hydrochloride are added at r.t. After stirring for 5 min, precipitates are filtered off and dried in vacuo to give 2-[(4-but-3-enyloxy-benzenesulfonyl)-(4-[1,2,4]triazol-1-yl-benzyl)-amino]-N-hydroxy-acetamide-hydrochloride salt as colorless powder. $^1$H-NMR (400 MHz, DMSO-d6): 2.45–2.55 (m, 2H), 3.67 (s, 2H), 4.13 (t, 2H, J=6.56 Hz), 4.41 (s, 2H), 5.09–5.22 (m, 2H), 5.90 (m, 1H), 7.10 (d, 2H, J=9.04 Hz), 7.45 (d, 2H, J=8.56 Hz), 7.75–7.85 (m, 4H), 8.25 (s, 1H), 9.32 (s, 1H), 10.55 (brs, 1H).

Stage 79.1: 4-But-3-enyloxy-benezenesulfonic acid sodium salt

To a suspension of 25 g (108 mmol) of p-phenolsulfonic acid sodium salt-dihydrate in 100 ml of ethanol, 54 ml of 2 N aqueous sodium hydroxide (160 mmol) and 11 ml (108 mmol) of 4-bromo-1-butene are successively added at r.t. After refluxing for 15 h at 90° C., the mixture is cooled to 0° C. to afford precipitates which are filtered off, washed twice with cold water and dried in vacuo to give 4-but-3-enyloxy-benzenesulfonic acid sodium salt. $^1$H-NMR (400 MHz, DMSO-d6): 2.30–2.40 (m, 2H), 3.89 (t, 2H, J=6.6 Hz), 4.92–5.07 (m, 2H), 5.70–5.80 (m, 1H), 6.72 (d, J=11.4 Hz, 2H), 7.96 (d, J=11.4 Hz, 2H).

Stage 79.2: 4-But-3-enyloxy-benezenesulfonyl chloride

To a suspension of 13 g (62 mmol) of 4-but-3-enyloxy-benezenesulfonic acid sodium salt in 25 ml of CH$_2$Cl$_2$, 24.1 ml (333 mmol) of thionyl chloride and 0.9 ml of DMF are successively added at r.t. After stirring for 15 h at r.t., the reaction mixture is poured into ice water, extracted with ether, dried over MgSO$_4$ and concentrated under reduced pressure to give 4-but-3-enyloxy-benezenesulfonyl chloride. $^1$H-NMR (400 MHz, CDCl$_3$): 2.55–2.65 (m, 2H), 4.14 (t, 2H, J=6.6 Hz), 5.10–5.25 (m, 2H), 5.72–5.95 (m, 1H), 7.04 (d, 2H, J=9.04 Hz), 7.96 (d, 2H, J=9.04 Hz).

Stage 79.3: 4-(1,2,4] Triazol-1-yl-benzaldehyde

To a solution of 6.44 ml (60 mmol) of p-fluorobenzaldehyde in 40 ml of pyridine, 4.14 g (60 mmol) of 1,2,4-triazole, 0.286 g (2 mmol) of copper(I)oxide and 9.12 g (66 mmol) of potassium carbonate are succesively added at r.t. After stirring for 18 h at 125° C., the reaction mixture is concentrated under reduced pressure. The residue is diluted with CHCl$_3$ and filtered through celite. The filtrate is concetrated and purified by flash column chromatography on silica gel (eluent: n-Hexane:AcOEt=4:1~AcOEt only~AcOEt: MeOH=20:1) to give 4-[1,2,4] triazol-1-yl-benzaldehyde as major product and 4-[1,3,4] triazol-1-yl-benzaldehyde as minor product. $^1$H-NMR (400 MHz, CDCl$_3$): 7.61 (d, 2H, J=8.56 Hz), 8.09 (d, 2H, J=8.56 Hz), 8.59 (s, 1H), 10.10 (s, 1H) (minor product); 7.91 (d, 2H, J=7.07 Hz), 8.05 (d, 2H, J=7.07 Hz), 8.16 (s, 1H), 8.69 (s, 1H), 10.07 (s, 1H) (major product).

Stage 79.4: (4-[1,2,4] Triazol-1-yl-benzylamino)-acetic acid ethyl ester

To a solution of 3.5 g (20 mmol) of 4-[1,2,4] triazol-1-yl-benzaldehyde and 4.19 g (30 mmol) of glycine ethyl ester hydrochloride in 100 ml of $CH_2Cl_2$, 4.18 ml (30 mmol) of triethyl amine and excess of $MgSO_4$ (14 g) are successively added at r.t. After being stirred for 18 h at r.t., the reaction mixture is filtered through celite and concentrated under reduced pressure. The residue is diluted with AcOEt and filtered again. The filtrate is concentrated under reduced pressure to give the crude imine. To a solution of the crude imine in 12 ml of MeOH, 0.756 mg (20 mmol) of $NaBH_4$ is added at −10° C. After being stirred for 1 h, the reaction is quenched with sat. $NH_4Cl$ and the reaction mixture is extracted with AcOEt. The combined extracts are washed with brine, dried over $MgSO_4$ and concentrated under reduced pressure. The residue is purified by column chromatography on silica gel (eluent: n-Hexane: AcOEt=1:10) to give the title compound. $^1$H-NMR (400 MHz, $CDCl_3$): 1.29 (t, 3H, J=7.04 Hz), 1.90 (brs, 1H), 3.43 (s, 2H), 3.88 (s, 2H), 4.21 (q, 2H, J=7.04 Hz), 7.49 (d, 2H, J=8.56 Hz), 7.64 (d, 2H, J=8.56 Hz), 8.10 (s, 1H), 8.55 (s, 1H).

Stage 79.5: [(4-But-3-enyloxy-benzensulfonyl)-(4-[1,2,4]triazol-1-yl-benzyl)-amino]-acetic acid ethyl ester To a solution of 2 g (7.683 mmol) of (4-[1,2,4]triazol-1-yl-benzylamino)-acetic acid ethyl ester in 15 ml of dioxane and 15 ml of H 20, 2.3 g (9.22 mmol) of 4-but-3-enyloxy-benzenesulfonyl chloride and 1.3 ml (9.22 mmol) of triethyl amine are successively added at 0–5° C. After being stirred for 18 h at r.t., the reaction mixture is diluted with H 20 and extracted with AcOEt. The combined extracts are washed with brine, dried over $MgSO_4$ and concentrated under reduced pressure. The residue is purified by column chromatography on silica gel to give the title compound. $^1$H-NMR (400 MHz, $CDCl_3$): 1.17 (t, 3H, J=7.04 Hz), 2.55–2.65 (m, 2H), 3.95 (s, 2H), 4.07 (t, 2H, J=7.04 Hz), 4.09 (t, 2H, J=6.56 Hz), 4.53 (s, 2H), 5.10–5.25 (m, 2H), 5.85–5.95 (m, 1H), 6.99 (d, 2H, J=8.04 Hz), 7.44 (d, 2H, J=7.56 Hz), 7.64 (d, 2H, J=8.04 Hz), 7.82 (d, 2H, J=7.56 Hz), 8.11 (s, 1H), 8.55 (s, 1H).

Stage 79.6: 2-[(4-But-3-enyloxy-benzenesulfonyl)-(4-[1,2,4]triazol-1-yl-benzyl)-amino]-N-(1-methoxy-1-methyl-ethoxy)-acetamide To a solution of 3.61 g (7.67 mmol) of [(4-but-3-enyloxy-benzensulfonyl)-(4-[1,2,4] triazol-1-yl-benzyl)-amino]-acetic acid ethyl ester in 38 ml of THF and 38 ml of MeOH, 0.966 g (23 mmol) of lithium hydroxide monohydrate and 4 ml of H 20 are added at 0–5° C. After being stirred for 3.5 h, the reaction mixture is acidified with 2 N aqueous hydrochloride at 0–5° C. and concentrated under reduced pressure to give [(4-but-3-enyloxy-benzensulfonyl)-(4-[1,2,4]triazol-1-yl-benzyl)-amino]-acetic acid as a colorless powder. To a solution of 3.76 g of the above prepared acid and 1.87 g (13.81 mmol) of 1-hydroxybenztriazole (HOBT) in 35 ml of DMF, 1.61 g (15.34 mmol) of O-(1-methyoxy-1-methyl-ethyl)-hydroxylamine and 1.91 g (12.275 mmol) of 1-ethyl-3-(3-dimethylaminopropyl)-carbodiimide are added successively at 0° C. After being stirred for 3.5 h at r.t., the reaction mixture is poured into ice water and the mixture is extracted with AcOEt. The combined extracts are washed with brine, dried over $MgSO_4$ and concentrated under reduced pressure. The residue is purified by column chromatography on silica gel (eluent: n-Hexane: AcOEt=1:3~1:4) to give the title compound. $^1$H-NMR (400 MHz, $CDCl_3$): 1.34 (s, 6H), 2.55–2.65 (m, 2H), 3.29 (s, 3H), 3.73 (s, 2H), 4.09 (t, J=6.60 Hz, 2H), 4.44 (s, 2H), 5.10–5.25 (m, 2H), 5.85–5.95 (m, 1H), 7.01 (d, 2H, J=8.52 Hz), 7.44 (d, 2H, J=8.0 Hz), 7.64 (d, 2H, J=8.52 Hz), 7.81 (d, 2H, J=8.0 Hz), 8.10 (s, 1H), 8.54 (s, 1H), 8.62 (brs, 1H).

EXAMPLE 80

2-[(4-But-3-enyloxy-benzenesulfonyl)-(4-imidazol-1-yl-benzyl)-amino]-N-hydroxy-acetamide-hydrochloride To a solution of 0.39 g (0.74 mmol) of 2-[(4-but-3-enyloxy-benzenesulfonyl)-(4-imidazol-1-yl-benzyl)-amino]-N-(1-methoxy-1-methyl-ethoxy)-acetamide (stage 80.4), 2.46 ml of 6 N aqueous hydrochloride is added at r.t. After being stirred for 15 min, the reaction mixture is neutralized with sat. $NaHCO_3$ and extracted with AcOEt. The combined extracts are washed with brine, dried over $MgSO_4$ and concentrated under reduced pressure to give 2-[(4-but-3-enyloxy-benzenesulfonyl)-(4-imidazol-1-yl-benzyl)-amino]-N-hydroxy-acetamide as a colorless powder. To a solution of 0.17 g (0.37 mmol) of the above prepared hydroxy acetamide in 3 ml of dioxane, 0.447 ml of 1 N aqueous hydrochloride is added and stirred for 10 min. The reaction mixture is concentrated under reduced pressure and dried in vacuo to give ther title compound. $^1$H-NMR (400 MHz, DMSO-d6): 2.40–2.50 (m, 2H), 3.61 (s, 2H), 4.07 (t, 2H, J=6.52 Hz), 4.37 (s, 2H), 5.00–5.15 (m, 2H), 5.75–5.90 (m, 1H), 7.04 (d, 2H, J=8.56 Hz), 7.48 (d, 2H, J=8.56 Hz), 7.65–7.75 (m, 5H), 7.81 (s, 1H), 8.19 (s, 1H), 9.57 (s, 1H), 10.54 (brs, 1H).

Stage 80.1: 4-Imidazol-1-yl-benzaldehyde

To a solution of 20 g (161.1 mmol) of p-fluorobenzaldehyde in 300 ml of DMF, 19.8 g (290.8 mmol) of imidazole and 44.5 g (322.24 mmol) of potassium carbonate are step by step added at r.t. After being stirred for 5.5 h at 100° C., the reaction mixture is cooled to r.t., diluted with ice water and then the mixture is extracted with AcOEt and $CH_2Cl_2$. The combined extracts are concentrated under reduced pressure to give 4-imidazol-1-yl-benzaldehyde as a pale yellow powder. $^1$H-NMR (400 MHz, $CDCl_3$): 7.26 (s, 1H), 7.38 (2, 1H), 7.59 (d, 2H, J=8.56 Hz), 7.98 (s, 1H), 8.02 (d, 2H, J=8.56 Hz), 10.05 (s, 1H).

Stage 80.2: (4-Imidazol-1-yl-benzylamino)-acetic acid methyl ester

The title compound is prepared in the same manner as (4-[1,2,4] Triazol-1-yl-benzyl-amino)-acetic acid ethyl ester (stage 79.4). $^1$H-NMR (400 MHz, $CDCl_3$): 1.92 (brs, 1H), 3.45 (s, 2H), 3.75 (s, 3H), 3.86 (s, 2H), 7.20 (s, 1H), 7.27 (s, 1H), 7.35 (d, 2H, J=8.56 Hz), 7.45 (d, 2H, J=8.56 Hz), 7.84 (s, 1H).

Stage 80.3: [(4-But-3-enyloxy-benzensulfonyl)-(4-imidazol-1-yl-benzyl)-amino]-acetic acid methyl ester The title compound is prepared in the same manner as [(4-but-3-enyloxy-benzensulfonyl)-(4-[1,2,4]triazol-1-yl-benzyl)-amino]-acetic acid ethyl ester (stage 79.5). $^1$H-NMR (400 MHz, $CDCl_3$): 2.55–2.65 (m, 2H), 3.59 (s, 3H), 3.95 (s, 3H), 4.05–4.10 (m, 2H), 4.51 (s, 2H), 5.10–5.25 (m, 2H), 5.85–6.00 (m, 1H), 6.99 (d, 2H, J=7.04 Hz), 7.20 (s, 1H), 7.27 (s, 1H), 7.35 (d, 2H, J=8.56 Hz), 7.40 (d, 2H, J=8.56 Hz), 7.83 (d, 2H, J=7.04 Hz), 7.84 (s, 1H).

Stage 80.4: 2-[(4-But-3-enyloxy-benzenesulfonyl)-(4-imidazol-1-yl-benzyl)-amino]-.N(1-methoxy-1-methyl-ethoxy)-acetoamide The title compound is prepared in the same manner as 2-[(4-but-3-enyloxy-benzenesulfonyl)-(4-[1,2,4]triazol-1- yl-benzyl)-amino]-N-(1-methoxy-1-methyl-ethoxy)-acetamide (stage 79.6). $^{1}$H-NMR (400 MHz, CDC): 1.35 (s, 6H), 2.55–2.65 (m, 2H), 3.28 (s, 3H), 3.73 (s, 2H), 4.05–4.15 (m, 2H), 4.42 (s, 2H), 5.10–5.25 (m, 2H), 5.82–5.95 (m, 1H), 7.01 (d, 2H, J=8.52 Hz), 7.20 (s, 1H), 7.24 (s, 1H), 7.34 (d, 2H, J=8.56 Hz), 7.44 (d, 2H, J=8.52 Hz), 7.81 (d, 2H, J=8.56 Hz), 7.83 (s, 1H), 8.72 (br s, 1H).

EXAMPLE 81

2-[(4-But-3-enyloxy-benzenesulfonyl)-(4-morpholin-4-yl-benzyl)-amino]-N-hydroxy-acetamide-hydrochloride The title compound was prepared in the same manner as the title compound of Example 80. $^{1}$H-NMR (400 MHz, DMSO-d6): 2.40–2.55 (m, 2H), 3.00–3.10 (m, 4H), 3.65–3.75 (m, 4H), 4.05 (t, 2H, J=6.52 Hz), 4.20 (s, 2H), 5.00–5.18 (m, 2H), 5.75–5.90 (m, 1H), 6.89 (d, 2H, J=8.56 Hz), 7.00–7.10 (m, 4H), 7.70 (d, 2H, J=8.56 Hz), 10.41 (brs, 1H).

Stage 81.1: 4-Morpholin-4-yl-benzaldehyde

To a solution of 15 g (120.86 mmol) of p-fluorobenzaldehyde in 200 ml of DMF, 16.8 g (193.4 mmol) of morpholine and 33.36 g (241.7 mmol) of potassium carbonate are added successively at r.t. After being stirred for 8 h at 100° C., the reaction mixture is cooled to r.t., diluted with ice water and then the mixture is extracted with AcOEt and CH$_2$Cl$_2$. The combined extracts are concentrated under reduced pressure and purified by silica gel column chlomatography (eluent: n-Hexane:AcOEt=5:1~3:1) to give 4-morpholin-4-yl-benzaldehyde. $^{1}$H-NMR (400 MHz, CDCl$_3$): 3.35–3.40 (m, 4H), 3.85–3.90 (m, 4H), 6.92 (d, 2H, J=8.56 Hz), 7.77 (d, 2H, J=8.56 Hz), 9.80 (s, 1H).

Stage 81.2: (4-Morpholin-4-yl-benzylamino) acetic acid methyl ester

The title compound was prepared in the same manner as (4-[1,2,4]triazol-1-yl-benzylamino)-acetic acid ethyl ester (stage 80.2). $^{1}$H-NMR (400 MHz, CDCl$_3$): 1.82 (brs, 1H), 3.10–3.18 (m, 4H), 3.41 (s, 2H), 3.85–3.90 (m, 4H), 6.87 (d, 2H, J=8.56 Hz), 7.23 (d, 2H, J=8.56 Hz).

Stage 81.3: [(4-But-3-enyloxy-benzensulfonyl)-(4-morpholin-4-yl-benzyl)-amino]-acetic acid methyl ester The title compound is prepared in the same manner as [(4-but-3-enyloxy-benzensulfonyl)-(4-[1,2,4] triazol-1-yl-benzyl)-amino]-acetic acid ethyl ester (stage 80.3). $^{1}$H-NMR (400 MHz, CDCl$_3$): 2.50–2.62 (m, 2H), 3.10–3.20 (m, 4H), 3.56 (s, 3H), 3.82–3.88 (m, 4H), 3.89 (s, 2H), 4.05–4.10 (m, 2H), 4.38 (s, 2H), 5.10–5.25 (m, 2H), 5.80–6.00 (m, 1H), 6.83 (d, 2H, J=8.56 Hz), 6.97 (d, 2H, J=9.04 Hz), 7.13 (d, 2H, J=8.56 Hz), 7.81 (d, 2H, J=9.04 Hz).

Stage 81.4: 2-[(4-But-3-enyloxy-benzenesulfonyl)-(4-morpholin-4-yl-benzyl)-amino]-N-(1-methoxy-1-methylethoxy)-acetamide The title compound is prepared in the same manner as 2-[(4-but-3-enyloxy-benzenesulfonyl)-(4-[1,2,4] triazol-1-yl-benzyl)-amino]-N-(1-methoxy-1-methyl-ethoxy)-acetamide (stage 80.3). $^{1}$H-NMR(400 MHz, CDCl$_3$): 1.35 (s, 6H), 2.55–2.62 (m, 2H), 3.10–3.20 (m, 4H), 3.29 (s, 3H), 3.66 (s, 2H), 3.80–3.88 (m, 4H), 4.05–4.15 (m, 2H), 4.26 (s, 2H), 5.10–5.22 (m, 2H), 5.83–5.95 (m, 1H), 6.83 (d, 2H, J=9.04 Hz), 7.00 (d, 2H, J=8.56 Hz), 7.15 (d, 2H, J=9.04 Hz), 7.79 (d, 2H, J=8.56 Hz), 8.47 (brs, 1H).

EXAMPLE 82

In analogy to Example 79 the following compounds can be prepared:

a) 2-[(2-Cyclopropylethoxy-benzenesulfonyl)-(4-[1,2,4] triazol-1-yl-benzyl)-amino]-N-hydroxy-acetamide-hydrochloride salt b) 2-[(Cyclopropylmethoxy-benzenesulfonyl)-(4-[1,2,4] triazol-1-yl-benzyl)-amino]-N-hydroxy-acetamide-hydrochloride salt c) 2-[(3-Furylmethoxy-benzenesulfonyl)-(4-[1,2,4]triazol-1-yl-benzyl)-amino]-N-hydroxy-acetamide-hydrochloride salt d) 2-[2-(3-Furyl)ethoxy-benzenesulfonyl)-(4-[1,2,4]triazol-1-yl-benzyl)-amino]-N-hydroxy-acetamide-hydrochloride salt

EXAMPLE 83

In analogy to Example 69 the following compounds can be prepared:

a) 2-[([4-But-3-enyloxy-benzenesulfonyl]-(6-fluoro-pyridine-2-yl)methyl-amino]-N-hydroxy-acetamide b) 2-[([4-But-3-enyloxy-benzenesulfonyl]-(2-fluoro-pyridine-4-yl)methyl-amino]-N-hydroxy-acetamide c) 2-[([4-But-3-enyloxy-benzenesulfonyl]-(6-fluoro-pyridine-3-yl)methyl-amino]-N-hydroxy-acetamide d) 2-[(4-But-3-enyloxy-benzenesulfonyl)-(piperidin-4-yl-methyl)-amino]-N-hydroxy-acetamide-hydrochloride e) 2-[(4-But-3-enyloxy-benzenesulfonyl)-(piperidin-1-yl-methyl)-amino]-N-hydroxy-acetamide-hydrochloride f) 2-[(4-But-3-enyloxy-benzenesulfonyl)-(morpholin-4-yl-methyl)-amino]-N-hydroxy-acetamide-hydrochloride

EXAMPLE 84

In analogy to Example 80 the following compounds can be prepared:

a) 2-[(4-But-3-enyloxy-benzenesulfonyl)-(4-(pyrrolidin-1-yl)-benzyl)-amino]-N-hydroxy-acetamide-hydrochloride b) 2-[(4-But-3-enyloxy-benzenesulfonyl)-(4-(piperidin-1-yl)-benzyl)-amino]-N-hydroxy-acetamide-hydrochloride c) 2-[(4-But-3-enyloxy-benzenesulfonyl)-(4-(1,2,3-triazol-2-yl)-benzyl)-amino]-N-hydroxy-acetamide-hydrochloride d) 2-[(4-But-3-enyloxy-benzenesulfonyl)-(4-(tetrazol-1-yl)-benzyl)-amino]-N-hydroxy-acetamide-hydrochloride e) 2-[(4-But-3-enyloxy-benzenesulfonyl)-(4-(1,3,4-triazol-1-yl)-benzyl)-amino]-N-hydroxy-acetamide-hydrochloride f) 2-[(4-But-3-enyloxy-benzenesulfonyl)-(4-(1,2,3-triazol-1-yl)-benzyl)-amino]-N-hydroxy-acetamide-hydrochloride g) 2-[(4-But-3-enyloxy-benzenesulfonyl)-(4-(pyrrol-1-yl)-benzyl)-amino]-N-hydroxy-acetamide h) 2-[(4-But-3-enyloxy-benzenesulfonyl)-(4-dimethylaminobenzyl)-amino]-N-hydroxy-acetamide-hydrochloride i) 2-[(4-But-3-enyloxy-benzenesulfonyl)-(4-(3-furyl)-benzyl)-amino]-N-hydroxy-acetamide k) 2-[(4-But-3-enyloxy-benzenesulfonyl)-(4-(thien-5-yl)-benzyl)-amino]-N-hydroxy-acetamide l) 2-[(4-But-3-enyloxy-benzenesulfonyl)-(4-morpholin-4-ylmethyl-benzyl)-amino]-N-hydroxy-acetamide-hydrochloride

EXAMPLE 85

In analogy to Example 68 the following compounds can be prepared:

a) 2-[([4-(3-chloro-propoxy)-benzenesulfonyl]-(4-(morpholin-4-ylmethyl)-benzyl)-amino]-N-hydroxy-acetamide b) 2-[([4-(3-chloro-propoxy)-benzenesulfonyl]-(quinolin-4-ylmethyl)-amino N-hydroxy-acetamide c) 2-[([4-(3-chloro-propoxy)-benzenesulfonyl]-(imidazol-4-ylmethyl)-amino}-N-hydroxy-acetamide d) 2-([4-(3-chloro-propoxy)benzenesulfonyl]-(1,2,4-triazol-3-ylmethyl)-amino}-N-hydroxy-acetamide

EXAMPLE 86

Dry capsules 3000 capsules, each of which contain 0.25 g of one of the compounds of the formula I mentioned in the preceding Examples as active ingredient, are prepared as follows:

| Composition | |
|---|---|
| Active ingredient | 75.00 g |
| Lactose | 750.00 g |
| Avicel PH 102 (microcrystalline cellulose) | 300.00 g |
| Polyplasdone XL (polyvinylpyrrolidone) | 30.00 g |
| Magnesium stearate | 9.00 g |

Preparation process: The active ingredient is passed through a No. 30 hand screen. The active ingredient, lactose, Avicel PH 102 and Polyplasdone XL are blended for 15 minutes in a mixer. The blend is granulated with sufficient water (about 500 mL), dried in an oven at 35° C. overnight, and passed through a No. 20 screen.

Magnesium stearate is passed through a No. 20 screen, added to the granulation mixture, and the mixture is blended for 5 minutes in a mixer. The blend is encapsulated in No. 0 hard gelatin capsules each containing an amount of the blend equivalent to 25 mg of the active ingredient.

EXAMPLE 87

In Vitro Activity on MT1-MMP. MMP1. MMP2 and MMP9

The inhibitory activities of compounds of formula I on MT1-MMP, MMP1, MMP2 and MMP9 as determined in the in vitro tests described in the present application are given in Tabel I.

TABLE I

| Example | MT1-MMP $IC_{50}$ [μmol/liter] | MMP1 $IC_{50}$ [μmol/liter] | MMP2 $IC_{50}$ [μmol/liter] | MMP9 $IC_{50}$ [μmol/liter] |
|---|---|---|---|---|
| 13 | 0.0055 | | | |
| 15 | 0.0037 | | | |
| 30 | 0.0127 | | | |
| 53 | 0.0092 | | | |
| 68 | 0.0052 | 0.622 | 0.0007 | 0.0012 |
| 75 | 0.0014 | 0.069 | 0.0010 | |
| 79 | 0.0007 | 5.850 | 0.0002 | 0.0002 |
| 80 | 0.0012 | 2.610 | 0.0080 | 0.0037 |
| 81 | 0.0046 | 4.290 | 0.0104 | 0.0063 |
| 82a | 0.0018 | 4.215 | 0.0402 | 0.0170 |
| 82b | 0.0006 | 0.965 | 0.0104 | 0.0106 |
| 82c | 0.0107 | 5.103 | 0.0053 | 0.0074 |
| 83a | 0.0003 | 3.694 | 0.0021 | 0.0056 |
| 84a | 0.0204 | 5.528 | 0.0147 | 0.0198 |

What is claimed is:

1. An α-amino hydroxamic acid derivative of the formula I,

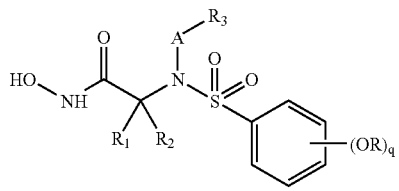

wherein
R$^1$ is hydrogen, substituted or unsubstituted aryl, lower alkyl, substituted or unsubstituted carbocyclic aryl-lower alkyl, substituted or unsubstituted $C_3$–$C_7$-cycloalkyl, substituted or unsubstituted $C_3$–$C_7$-cycloalkyl-lower alkyl, hydroxy-lower alkyl, lower alkoxy-lower alkyl, lower alkyl-(thio, sulfinyl or sulfonyl)-lower alkyl, amino-lower alkyl or mono- or di-lower alkylamino-lower alkyl;

R$^2$ is hydrogen or lower alkyl;

R$^3$ is substituted or unsubstituted $C_3$–$C_7$-cycloalkyl, substituted or unsubstituted carbocyclic aryl; or lower alkyl;

A is $C_1$–$C_3$ alkylene unsubstituted or substituted by lower alkyl;

q is 1–5;

R is $C_2$–$C_7$-alkyl, which is mono-, di- or trisubstituted by halogen, nitro, lower acyloxy, trifluoromethoxy, cyano, or $C_3$–$C_5$-cycloalkyl; or $C_3$–$C_7$-alkenyl or $C_3$–$C_7$-alkynyl, which in each case is unsubstituted or mono-, di- or trisubstituted by halogen, nitro, lower acyloxy, trifluoromethoxy, cyano, or $C_3$–$C_5$-cycloalkyl;

and pharmaceutically acceptable prodrug acyl derivatives; and pharmaceutically acceptable salts thereof.

2. A compound of formula I according to claim 1, wherein R$^1$ is hydrogen, lower alkyl;

monocyclic or bicyclic carbocyclic aryl which is unsubstituted or mono-, di- or trisubstituted by lower alkyl, lower alkoxy, hydroxy, halogen, cyano, trifluoromethyl, phenoxy or phenyl which is unsubstituted or substituted by lower alkoxy, lower alkyl, halogen, cyano, nitro, trifluoromethyl or lower-alkylenedioxy;

carbocyclic aryl-lower alkyl which is unsubstituted or mono-, di- or trisubstituted by lower alkyl, lower alkoxy, hydroxy, halogen, cyano, trifluoromethyl, phenoxy or phenyl which is unsubstituted or substituted by lower alkoxy, lower alkyl, halogen, cyano, nitro, trifluoromethyl or lower-alkylenedioxy in the carbocyclic moiety;

$C_3$–$C_7$-cycloalkyl, which is unsubstituted or substituted by lower alkyl;

$C_3$–$C_7$-cycloalkyl-lower alkyl, which is unsubstituted or substituted by lower alkyl; hydroxy-lower alkyl, lower alkoxy-lower alkyl, lower alkyl-(thio, sulfinyl or sulfonyl)-lower alkyl, amino-lower alkyl or mono- or di-lower alkylamino-lower alkyl;

R$^2$ is hydrogen or lower alkyl;

R$^3$ is $C_3$–$C_7$-cycloalkyl, which is unsubstituted or substituted by lower alkyl; carbocyclic aryl, which is unsubstituted or mono-, di- or trisubstituted by lower alkyl, lower alkoxy, hydroxy, halogen, cyano, trifluoromethyl, phenoxy or phenyl which is unsubstituted or substituted by lower alkoxy, lower alkyl, halogen, cyano, nitro, trifluoromethyl or lower-alkylenedioxy; or lower alkyl;

A is $C_1$–$C_3$ alkylene unsubstituted or substituted by lower alkyl;

q is 1–5;

R is $C_2$–$C_7$-alkyl, which is mono-, di- or trisubstituted by halogen, nitro, lower acyloxy, trifluoromethoxy, cyano, or $C_3$–$C_5$-cycloalkyl which is unsubstituted or substituted by lower alkyl; or $C_3$–$C_7$-alkenyl or $C_3$–$C_7$-alkynyl, which in each case is unsubstituted or mono-, di- or trisubstituted by halogen, nitro, lower acyloxy, trifluoromethoxy, cyano, or $C_3$–$C_5$-cycloalkyl, which is unsubstituted or substituted by lower alkyl;

and pharmaceutically acceptable prodrug acyl derivatives; and pharmaceutically acceptable salts thereof.

3. A compound of formula I according to claim 1, wherein R$_1$ is hydrogen, substituted or unsubstituted aryl, lower alkyl, substituted or unsubstituted carbocyclic aryl-lower alkyl, substituted or unsubstituted $C_3$–$C_7$-cycloalkyl, substituted or unsubstituted $C_3$–$C_7$-cycloalkyl-lower alkyl, hydroxy-lower alkyl, lower alkoxy-lower alkyl, lower alkyl-(thio, sulfinyl or sulfonyl)-lower alkyl, amino-lower alkyl or mono- or di-lower alkylamino-lower alkyl;

R$_2$ is hydrogen or lower alkyl;

R$_3$ is substituted or unsubstituted $C_3$–$C_7$-cycloalkyl, substituted or unsubstituted carbocyclic aryl, or lower alkyl;

A is $C_1$–$C_3$ alkylene unsubstituted or substituted by lower alkyl;

q is 1–5;

R is $C_2$–$C_7$-alkyl, which is mono-, di- or trisubstituted by halogen, nitro, lower acyloxy, trifluoromethoxy or cyano; $C_3$–$C_7$-alkenyl or $C_3$–$C_7$-alkynyl, which in each case is unsubstituted or mono-, di- or trisubstituted by halogen, nitro lower acyloxy, trifluoromethoxy or cyano; and pharmaceutically acceptable prodrug acyl derivatives; and pharmaceutically acceptable salts thereof.

4. A compound of formula I according to claim 1, wherein R$_1$ is hydrogen, lower alkyl, or carbocyclic aryl-lower alkyl which is unsubstituted or mono-, di- or trisubstituted by lower alkyl, lower alkoxy, hydroxy, halogen, cyano, trifluoromethyl, phenoxy or phenyl which is unsubstituted or substituted by lower alkoxy, lower alkyl, halogen, cyano, nitro, trifluoromethyl or lower-alkylenedioxy in the carbocyclic moiety;

R$_2$ is hydrogen or lower alkyl;

$R_3$ is $C_3$–$C_7$-cycloalkyl, which is unsubstituted or substituted by lower alkyl, carbocyclic aryl, which is unsubstituted or mono-, di- or trisubstituted by lower alkyl, lower alkoxy, hydroxy, di-lower alkyl amino, halogen, cyano, trifluoromethyl, phenoxy or phenyl which is unsubstituted or substituted by lower alkoxy, lower alkyl, halogen, cyano, nitro, trifluoromethyl or lower-alkylenedioxy; or lower alkyl;

A is $C_1$–$C_3$ alkylene unsubstituted or substituted by lower alkyl;

q is 1 or 2;

R is $C_2$–$C_7$-alkyl, which is mono-, di- or trisubstituted by halogen, nitro, lower acyloxy, trifluoromethoxy, cyano, or $C_3$–$C_5$-cycloalkyl, which is unsubstituted or substituted by lower alkyl; or $C_3$–$C_7$-alkenyl or $C_3$–$C_7$-alkynyl, which in each case is unsubstituted or mono-, di- or trisubstituted by halogen, nitro, lower acyloxy, trifluoromethoxy, cyano, or $C_3$–$C_5$-cycloalkyl, which is unsubstituted or substituted by lower alkyl;

and pharmaceutically acceptable prodrug acyl derivatives; and pharmaceutically acceptable salts thereof.

5. A compound of formula I according to claim 1, wherein $R_1$ is hydrogen, lower alkyl, or substituted or unsubstituted carbocyclic aryl-lower alkyl;

$R_2$ is hydrogen or lower alkyl;

$R_3$ is substituted or unsubstituted $C_3$–$C_7$-cycloalkyl, substituted or unsubstituted carbocyclic aryl, or lower alkyl;

A is $C_1$–$C_3$ alkylene unsubstituted or substituted by lower alkyl;

q is 1 or 2;

R is $C_2$–$C_7$-alkyl, which is mono-, di- or trisubstituted by halogen, nitro, lower acyloxy, trifluoromethoxy or cyano; $C_3$–$C_7$-alkenyl or $C_3$–$C_7$-alkynyl, which in each case is unsubstituted or mono-, di- or trisubstituted by halogen, nitro, lower acyloxy, trifluoromethoxy or cyano;

and pharmaceutically acceptable prodrug acyl derivatives; and pharmaceutically acceptable salts thereof.

6. A compound of formula I according to claim 1, wherein $R_1$ is hydrogen, lower alkyl, or substituted or unsubstituted carbocyclic aryl-lower alkyl;

$R_2$ is hydrogen or lower alkyl;

$R_3$ is substituted or unsubstituted $C_3$–$C_7$-cycloalkyl; phenyl which is unsubstituted or mono- or disubstituted by lower alkyl, lower alkoxy, hydroxy, nitro, amino, lower-alkyl amino, carbamoyl, trifluoromethyl, trifluoromethoxy, lower alkylthio, lower acyloxy or halogen; or lower alkyl;

A is $C_1$–$C_3$ alkylene unsubstituted or substituted by lower alkyl;

q is 1 or 2;

R is $C_2$–$C_7$-alkyl, which is mono-, di- or trisubstituted by halogen, nitro, lower acyloxy, trifluoromethoxy or cyano; $C_3$–$C_7$-alkenyl or $C_3$–$C_7$-alkynyl, which in each case is unsubstituted or mono-, di- or trisubstituted by halogen, nitro, lower acyloxy, trifluoromethoxy or cyano;

and pharmaceutically acceptable prodrug acyl derivatives; and pharmaceutically acceptable salts thereof.

7. A compound of formula I according to claim 1, wherein $R_1$ is hydrogen, lower alkyl, or phenyl lower alkyl;

$R_2$ is hydrogen;

$R_3$ is phenyl monosubstituted by lower alkoxy or halogen; or lower alkyl;

A is $C_1$–$C_3$ alkylene;

q is 1;

R is $C_2$–$C_7$-alkyl, which is mono- or trisubstituted by halogen; unsubstituted $C_3$–$C_7$-alkenyl or unsubstituted $C_3$–$C_7$-alkynyl;

and pharmaceutically acceptable prodrug acyl derivatives; and pharmaceutically acceptable salts thereof.

8. A compound of formula I according to claim 1, wherein $R_1$ is hydrogen;

$R_2$ is hydrogen;

$R_3$ is phenyl monosubstituted by lower alkoxy or halogen;

A is $C_1$–$C_3$ alkylene;

q is 1;

R is unsubstituted $C_3$–$C_5$-alkenyl, in which the double bond is terminally located; or unsubstituted $C_3$–$C_5$-alkynyl, in which the triple bond is terminally located;

and pharmaceutically acceptable prodrug acyl derivatives; and pharmaceutically acceptable salts thereof.

9. A compound of formula I according to claim 1, wherein $R_1$ is hydrogen;

$R_2$ is hydrogen;

$R_3$ is phenyl monosubstituted by lower alkoxy or halogen;

A is methylene or ethylene;

q is 1; and

R is unbranched $C_3$–$C_5$-alkyl, which is terminally monosubstituted by halogen;

and pharmaceutically acceptable prodrug acyl derivatives; and pharmaceutically acceptable salts thereof.

10. A compound of formula I according to claim 1, wherein $R_1$ is hydrogen, lower alkyl, or phenyl lower alkyl;

$R_2$ is hydrogen;

$R_3$ is $C_3$–$C_7$-cycloalkyl, which is unsubstituted or substituted by lower alkyl;

phenyl which is unsubstituted or mono- or disubstituted by lower alkyl, lower alkoxy, hydroxy, nitro, amino, lower alkyl amino, di-lower alkyl amino, carbamoyl, trifluoromethyl, trifluoromethoxy, lower alkylthio, lower acyloxy, halogen;

A is methylene or ethylene;

q is 1;

R is $C_2$–$C_7$-alkyl, which is mono-, di- or trisubstituted by halogen, nitro, lower acyloxy, trifluoromethoxy, cyano, or $C_3$–$C_5$-cycloalkyl which is unsubstituted or substituted by lower alkyl; $C_3$–$C_7$-alkenyl or $C_3$–$C_7$-alkynyl, which in each case is unsubstituted or mono-, di- or trisubstituted by halogen, nitro, lower acyloxy, trifluoromethoxy, cyano or $C_3$–$C_5$-cycloalkyl which is unsubstituted or substituted by lower alkyl and pharmaceutically acceptable prodrug acyl derivatives; and pharmaceutically acceptable salts thereof.

11. A compound of formula I according to claim 1, wherein $R_1$ is hydrogen, lower alkyl, or phenyl lower alkyl;

$R_2$ is hydrogen;

$R_3$ is phenyl which is unsubstituted or mono- or disubstituted by lower alkyl, lower alkoxy, di-lower alkyl amino, halogen;

A is methylene;

q is 1;

R is unsubstituted $C_3$–$C_5$-alkenyl, in which the double bond is terminally located;

unsubstituted $C_3$–$C_5$-alkynyl, in which the triple bond is terminally located; or unbranched $C_3$–$C_5$-alkyl, which is terminally monosubstituted or trisubstituted by halogen, or terminally monosubstituted by cyclopropyl;

and pharmaceutically acceptable prodrug acyl derivatives; and pharmaceutically acceptable salts thereof.

12. A compound of the formula I according to claim 1 selected from the group consisting of (R)-2-{[4-(3-Chloro-propoxy)-benzenesulfonyl]-(4-fluoro-benzyl)-amino}-N-hydroxy-3-methyl-butyramide, (R)-2-{[4-(3-Chloro-propoxy)-benzenesulfonyl]-(3-methoxy-benzyl)-amino}-N-hydroxy-3-methyl-butyramide, (R)-2-{[4-(3-Chloro-propoxy)-benzenesulfonyl]-(4-methoxy-benzyl)-amino}-N-hydroxy-3-methyl-butyramide, (R)-2-{(4-Chloro-benzyl)-[4-(3-fluoro-propoxy)-benzenesulfonyl]-amino}-N-hydroxy-3-methyl-butyramide, (R)-2-[((4-Fluoro-benzyl)-[4-(3-fluoro-propoxy)-benzenesulfonyl]-amino]-N-hydroxy-3-methyl-butyramide, (R)-2-{(4-Fluoro-benzyl)-[4-(3-fluoro-propoxy)-benzenesulfonyl]-amino}-N-hydroxy-3-methyl-butyramide, (R)-2-{(4-Chloro-benzyl)-[4-(4-fluoro-butoxy)-benzenesulfonyl]-amino}-N-hydroxy-3-methyl-butyramide, (R)-2-{(4-Fluoro-benzyl)-[4-(4-fluoro-butoxy)-benzenesulfonyl]-amino}-N-hydroxy-3-methyl-butyramide, (R)-2-{[4-(4-Fluoro-butoxy)-benzenesulfonyl]-(3-methoxy-benzyl)-amino}-N-hydroxy-3-methyl-butyramide, (R)-2-[(4-But-3-enyloxy-benzenesulfonyl)-(4-chloro-benzyl)-amino]-N-hydroxy-3-methyl-butyramide, (R)-2-[(4-But-3-enyloxy-benzenesulfonyl)-(4-fluoro-benzyl)-amino]-N-hydroxy-3-methyl-butyramide, (R)-2-[(4-But-3-enyloxy-benzenesulfonyl)-(3-methoxy-benzyl)-amino]-N-hydroxy-3-methyl-butyramide, (R)-2-[(4-But-3-enyloxy-benzenesulfonyl)-(4-methoxy-benzyl)-amino]-N-hydroxy-3-methyl-butyramide, (R)-2-{[4-(3-Chloro-propoxy)-benzenesulfonyl]-(3-methoxy-benzyl)-amino}-N-hydroxy-propionamide, (R)-2-{[4-(3-Chloro-propoxy)-benzenesulfonyl]-(4-methoxy-benzyl)-amino}-N-hydroxy-propionamide, (R)-2-{(4-Chloro-benzyl)-[4-(3-fluoro-propoxy)-benzenesulfonyl]-amino}-N-hydroxy-propionamide, (R)-2-{(4-Fluoro-benzyl)-[4-(3-fluoro-propoxy)-benzenesulfonyl]-amino}-N-hydroxy-propionamide, (R)-2-{[4-(3-Fluoro-propoxy)-benzenesulfonyl]-(3-methoxy-benzyl)-amino}-N-hydroxy-propionamide, (R)-2-[(4-Fluoro-butoxy)-benzenesulfonyl]-amino]-N-hydroxy-propionamide, (R)-2-{[4-(4-Fluoro-butoxy)-benzenesulfonyl]-(4-methoxy-benzyl)-amino}-N-hydroxy-propionamide, (R)-2-[(4-But-3-enyloxy-benzenesulfonyl)-(4-chloro-benzyl)-amino]-N-hydroxy-propionamide, (R)-2-[(4-But-3-enyloxy-benzenesulfonyl)-(3-methoxy-benzyl)-amino]-N-hydroxy-propionamide, (R)-2-[(4-But-3-enyloxy-benzenesulfonyl)-(4-methoxy-benzyl)-amino]-N-hydroxy-propionamide, (R)-2-{(4-Chloro-benzyl)-[4-(3-chloro-propoxy)-benzenesulfonyl]-amino}-N-hydroxy-3-phenyl-propionamide, (R)-2-{[4-(3-Chloro-propoxy)-benzenesulfonyl]-(4-fluoro-benzyl)-amino]-N-hydroxy-3-phenyl-propionamide, (R)-2-{[4-(3-Chloro-propoxy)-benzenesulfonyl]-(3-methoxy-benzyl)-amino}-N-hydroxy-3-phenyl-propionamide, (R)-2-{[4-(3-Chloro-propoxy)-benzenesulfonyl]-(4-methoxy-benzyl)-amino}-N-hydroxy-3-phenyl-propionamide, (R)-2-{(4-Chloro-benzyl)-[4-(3-fluoro-propoxy)-benzenesulfonyl]-amino}-N-hydroxy-3-phenyl-propionamide, (R)-2-{(4-Fluoro-benzyl)-[4-(3-fluoro-propoxy)-benzenesulfonyl]-amino}-N-hydroxy-3-phenyl-propionamide, (R)-2-{[4-(3-Fluoro-propoxy)-benzenesulfonyl]-(3-methoxy-benzyl)-amino}-N-hydroxy-3-phenyl-propionamide, (R)-2-{[4-(3-Fluoro-propoxy)-benzenesulfonyl]-(4-methoxy-benzyl)-amino]-N-hydroxy-3-phenyl-propionamide, (R)-2-{(4-Chloro-benzyl)-[4-(4-fluoro-butoxy)-benzenesulfonyl]-amino}-N-hydroxy-3-phenyl-propionamide, (R)-2-{(4-Fluoro-benzyl)-[4-(4-fluoro-butoxy)-benzenesulfonyl]-amino}-N-hydroxy-3-phenyl-propionamide, (R)-2-{[4-(4-Fluoro-butoxy)-benzenesulfonyl]-(3-methoxy-benzyl)-amino}-N-hydroxy-3-phenyl-propionamide, (R)-2-{[4-(4-Fluoro-butoxy)-benzenesulfonyl]-(4-methoxy-benzyl)-amino}-N-hydroxy-3-phenyl-propionamide, (R)-2-[(4-But-3-enyloxy-benzenesulfonyl)-(4-chloro-benzyl)-amino]-N-hydroxy-3-phenyl-propionamide, (R)-2-[(4-But-3-enyloxy-benzenesulfonyl)-(4-fluoro-benzyl)-amino]-N-hydroxy-3-phenyl-propionamide, (R)-2-[(4-But-3-enyloxy-benzenesulfonyl)-(3-methoxy-benzyl)-amino]-N-hydroxy-3-phenyl-propionamide, (R)-2-[(4-But-3-enyloxy-benzenesulfonyl)-(4-methoxy-benzyl)-amino]-N-hydroxy-3-phenyl-propionamide, (R)-2-{(4-Chloro-benzyl)-[4-(3-chloro-propoxy)-benzenesulfonyl]-amino}-N-hydroxy-4-methyl-valeramide, (R)-2-{[4-(3-Chloro-propoxy)-benzenesulfonyl]-(4-fluoro-benzyl)-amino}-N-hydroxy-4-methyl-valeramide, (R)-2-{[4-(3-Chloro-propoxy)-benzenesulfonyl]-(3-methoxy-benzyl)-amino}-N-hydroxy-4-methyl-valeramide, (R)-2-{[4-(3-Chloro-propoxy)-benzenesulfonyl]-(4-methoxy-benzyl)-amino}-N-hydroxy-4-methyl-valeramide, (R)-2-{(4-Chloro-benzyl)-[4-(3-fluoro-propoxy)-benzenesulfonyl]-amino}-N-hydroxy-4-methyl-valeramide, (R)-2-{(4-Fluoro-benzyl)-[4-(3-fluoro-propoxy)-benzenesulfonyl]-amino}-N-hydroxy-4-methyl-valeramide, (R)-2-[([4-(3-Fluoro-propoxy)-benzenesulfonyl]-(3-methoxy-benzyl)-amino}-N-hydroxy-4-methyl-valeramide, (R)-2-{[4-(3-Fluoro-propoxy)-benzenesulfonyl]-(4-methoxy-benzyl)-amino}-N-hydroxy-4-methyl-valeramide, (R)-2-{(4-Chloro-benzyl)-[4-(4-fluoro-butoxy)-benzenesulfonyl]-amino}-N-hydroxy-4-methyl-valeramide, (R)-2-{(4-Fluoro-benzyl)-[4-(4-fluoro-butoxy)-benzenesulfonyl]-amino}-N-hydroxy-4-methyl-valeramide, (R)-2-{[4-(4-Fluoro-butoxy)-benzenesulfonyl]-(3-methoxy-benzyl)-amino}-N-hydroxy-4-methyl-valeramide, (R)-2-{[4-(4-Fluoro-butoxy)-benzenesulfonyl]-(4-methoxy-benzyl)-amino}-N-hydroxy-4-methyl-valeramide, (R)-2-[(4-But-3-enyloxy-benzenesulfonyl)-(4-chloro-benzyl)-amino]-N-hydroxy-4-methyl-valeramide, (R)-2-[(4-But-3-enyloxy-benzenesulfonyl)-(4-fluoro-benzyl)-amino]-N-hydroxy-4-methyl-valeramide, (R)-2-[(4-But-3-enyloxy-benzenesulfonyl)-(3-methoxy-benzyl)-amino]-N-hydroxy-4-methyl-valeramide, (R)-2-[(4-But-3-enyloxy-benzenesulfonyl)-(4-methoxy-benzyl)-amino]-N-hydroxy-4-methyl-valeramide, 2-{[4-(4-Fluoro-butoxy)-benzenesulfonyl]-(3-methoxy-benzyl)-amino}-N-hydroxy-acetamide, 2-{[4-(3-Chloro-propoxy)-benzenesulfonyl]-(4-fluoro-benzyl)-amino}-N-hydroxy-acetamide, 2-{[4-(3-Chloro-propoxy)-benzenesulfonyl]-(3-methoxy-benzyl)-amino}-N-hydroxy-acetamide, 2-{(4-Chloro-benzyl)-[4-(3-chloro-propoxy)-benzene-sulfonyl]-amino}-N-hydroxy-acetamide, 2-{(4-Fluoro-benzyl)-[4-(3-fluoro-propoxy)-benzene-sulfonyl]-amino}-N-hydroxy-acetamide, 2-{[4-(3-Fluoro-propoxy)-benzenesulfonyl]-(3-methoxy-benzyl)-amino}-N-hydroxy-acetamide, 2-{(4-Chloro-benzyl)-[4-(3-fluoro-propoxy)-benzene-sulfonyl]-amino}-N-hydroxy-acetamide, 2-{(4-Fluoro-benzyl)-[4-(4-fluoro-butoxy)-benzenesulfo-nyl]-amino}-N-hydroxy-acetamide, 2-{(4-Chloro-benzyl)-[4-(4-fluoro-butoxy)-benzene-sulfonyl]-amino}-N-hydroxy-acetamide, 2-[(4-But-3-enyloxy-benzenesulfonyl)-(4-chloro-ben-zyl)-amino]-N-hydroxy-acetamide, 2-{[4-(3-Chloro-propoxy)-benzenesulfonyl]-(4-methoxy-benzyl)-amino}-N-hydroxy-acetamide, 2-{[4-(4-Fluorobutoxy)-benzenesulfonyl]-(4-methoxy-benzyl)-amino]-N-hydroxy-acetamide, 2-{[4-(4-Chlorobutoxy)-benzenesulfonyl]-(4-methoxy-benzyl)-amino}-N-hydroxy-acetamide, {(4-Methoxy-benzyl)-[4-(4,4,4-trifluorobutoxy)-benze-nesulfonyl]-amino}-N-hydroxy-acetamide,

[(4-(4-Fluoropropoxy)-benzenesulfonyl]-(4-methoxy-benzyl)-amino}-N-hydroxy-acetamide,

[(4-But-3-en-1-yloxy-benzenesulfonyl)-(4-methoxy-ben-zyl)-amino]-N-hydroxy-acetamide,

[(4-Methoxy-benzyl)-[4-prop-2-ynyloxy-benzenesulfo-nyl]-amino]-N-hydroxy-acetamide,

[(4-Methoxy-benzyl)-[4-but-2-ynyloxy-benzenesulfo-nyl]-amino]-N-hydroxy-acetamide, 2-{[4-(3-Chloropropoxy)-benzenesulfonyl}-(2,2-dim-ethyl-propyl)-amino-N-hydroxy-acetamide, and 2-[(4-But-3-enyloxy-benzenesulfonyl)-(4-dimethylami-nobenzyl)-amino]-N-hydroxy-acetamide-hydrochlo-ride, or a pharmaceutical acceptable salt thereof.

13. A pharmaceutical composition comprising a compound of formula I according to claim 1 or a pharmaceutically acceptable salt or a pharmaceutically acceptable prodrug derivative of such a compound together with a pharmaceutical carrier.

14. A pharmaceutical composition for use for the treatment of tumors, wherein the tumors are selected from the group consisting of lung adenocarcinoma, melanoma, breast carcinoma, bladder carcinoma, colon carcinoma and ovarian carcinoma, in warm-blooded animals comprising an antitumourally effective dose of a compound of the formula I according to claim 1 or a pharmaceutically acceptable salt or a pharmaceutically acceptable prodrug acyl derivative of such a compound together with a pharmaceutical carrier.

15. A process for the preparation of an α-amino hydroxamic acid derivative of the formula I,

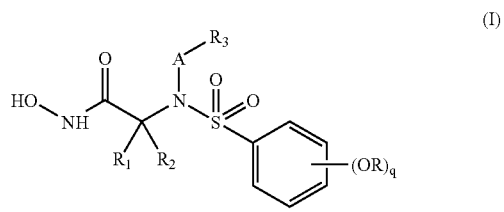

wherein $R^1$ is hydrogen, substituted or unsubstituted aryl, lower alkyl, substituted or unsubstituted carbocyclic aryl-lower alkyl, substituted or unsubstituted $C_3$–$C_7$-cycloalkyl, substituted or unsubstituted $C_3$–$C_7$-cycloalkyl-lower alkyl, hydroxy-lower alkyl, lower alkoxy-lower alkyl, lower alkyl-(thio, sulfinyl or sulfonyl)-lower alkyl, amino-lower alkyl or mono- or di-lower alkylamino-lower alkyl;

$R^2$ is hydrogen or lower alkyl;

$R^3$ is substituted or unsubstituted $C_3$–$C_7$-cycloalkyl, substituted or unsubstituted carbocyclic aryl, or lower alkyl;

A is $C_1$–$C_3$ alkylene unsubstituted or substituted by lower alkyl;

q is 1–5;

R is $C_2$–$C_7$-alkyl, which is mono-, di- or trisubstituted by halogen, nitro, lower acyloxy, trifluoromethoxy, cyano, or $C_3$–$C_5$-cycloalkyl; or $C_3$–$C_7$-alkenyl or $C_3$–$C_7$-alkynyl, which in each case is unsubstituted or mono-, di- or trisubstituted by halogen, nitro, lower acyloxy, trifluoromethoxy, cyano, or $C_3$–$C_5$-cycloalkyl;

or a salt or a pharmaceutically acceptable acyl prodrug thereof, which comprises a) reacting a compound of the formula II

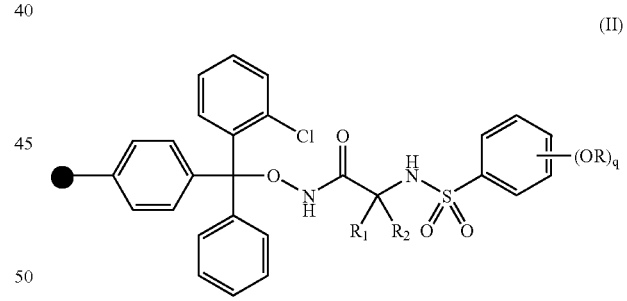

in which R, q, $R_1$ and $R_2$ are as defined above for compounds of the formula I and the black circular plane indicates that the compound is bound to a polymer resin, if necessary free functional group of formula (II), being protected by easily detachable protective groups, in a suitable solvent, first with triphenylphosphine, an alcohol of the structure III, HO—A—R₃ (III) 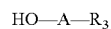

in which A and $R_3$ are as defined above for compounds of formula I, and diethyl azodicarboxylate, if necessary free functional group of formula (III), being protected by easily detachable protective groups b) cleaving the product of the reaction from the polymer resin and c) optionally converting a resulting free compound of the formula I into a salt if necessary for the preparation of a salt or, d) optionally converting a resulting salt of a compound of the formula I into the free compound of formula (I) if necessary for the preparation of a free compound of formula (I).

16. A method of treating tumors, wherein the tumors are selected from the group consisting of lung adenocarcinoma, melanoma, breast carcinoma, bladder carcinoma, colon carcinoma and ovarian carcinoma, comprising administering to a warm-blooded animal in need of said treating a therapeutically effective amount of a compound according to claim 1 or of a pharmaceutically acceptable salt or a pharmaceutically acceptable prodrug acyl derivative of said compound.

17. A method for treating chronic obstructive pulmonary disease comprising administering to a warm-blooded animal in need of said treating a therapeutically effective amount of a compound according to claim 1 or of a pharmaceutically acceptable salt or a pharmaceutically acceptable prodrug acyl derivative of said compound.

18. A method according to claim 14 wherein said warm-blooded animal is a human.

19. A method according to claim 16 wherein said warm-blooded animal is a human.

20. A method according to claim 17 wherein said warm-blooded animal is a human.

* * * * *

UNITED STATES PATENT AND TRADEMARK OFFICE
CERTIFICATE OF CORRECTION

| | |
|---|---|
| PATENT NO. | : 7,138,432 B1 |
| APPLICATION NO. | : 10/048932 |
| DATED | : November 21, 2006 |
| INVENTOR(S) | : Breitenstein et al. |

Page 1 of 1

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (262) days Delete the phrase "by 262" and insert -- by 123 days --

Signed and Sealed this

Sixth Day of January, 2009

JON W. DUDAS
*Director of the United States Patent and Trademark Office*